(12) United States Patent
Rigo et al.

(10) Patent No.: US 11,236,330 B2
(45) Date of Patent: Feb. 1, 2022

(54) ANTISENSE COMPOUNDS AND USES THEREOF

(71) Applicants: Ionis Pharmaceuticals, Inc., Carlsbad, CA (US); Cold Spring Harbor Laboratory, Cold Spring Harbor, NY (US)

(72) Inventors: Frank Rigo, Carlsbad, CA (US); C. Frank Bennett, Carlsbad, CA (US); Adrian R. Krainer, Huntington Station, NY (US); Zhenxun Wang, Singapore (SG)

(73) Assignees: Ionis Pharmaceuticals, Inc., Carlsbad, CA (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 16/149,941

(22) Filed: Oct. 2, 2018

(65) Prior Publication Data

US 2019/0249175 A1 Aug. 15, 2019

Related U.S. Application Data

(63) Continuation of application No. 14/440,018, filed as application No. PCT/US2013/067881 on Oct. 31, 2013, now abandoned.

(60) Provisional application No. 61/720,910, filed on Oct. 31, 2012.

(51) Int. Cl.
*C07H 21/04* (2006.01)
*C12N 15/113* (2010.01)

(52) U.S. Cl.
CPC ........ *C12N 15/113* (2013.01); *C12N 15/1137* (2013.01); *C12Y 207/0104* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| 2013/0018086 A1* | 1/2013 | Goldberg | A61P 35/04 514/44 A |
| 2015/0105444 A1* | 4/2015 | Freier | C07H 21/00 514/44 A |

FOREIGN PATENT DOCUMENTS

WO WO-2011115810 A2 * 9/2011 ............. A61P 35/00

OTHER PUBLICATIONS

Prakash, Thazha P. "An overview of sugar-modified oligonucleotides for antisense therapeutics." Chemistry & biodiversity 8.9 (2011): 1616-1641.*
Luo et al. Trends Endocrinol Metab. Nov. 2012; 23(11): 560-566. Published online Jul. 21, 2012).*
Kefas, et al. (2010, Neuro-Oncology, v.12:1102-1112, first published on-line Jul. 28, 2010).*

* cited by examiner

*Primary Examiner* — Kimberly Chong
(74) *Attorney, Agent, or Firm* — Michael Best & Friedrich LLP

(57) ABSTRACT

The present invention provides compounds comprising oligonucleotides complementary to a pyruvate kinase M transcript. Certain such compounds are useful for hybridizing to a pyruvate kinase M transcript, including but not limited to a pyruvate kinase M transcript in a cell. In certain embodiments, such hybridization results in modulation of splicing of the pyruvate kinase M transcript. In certain embodiments, such compounds are used to treat one or more symptoms associated with cancer.

20 Claims, 18 Drawing Sheets

Specification includes a Sequence Listing.

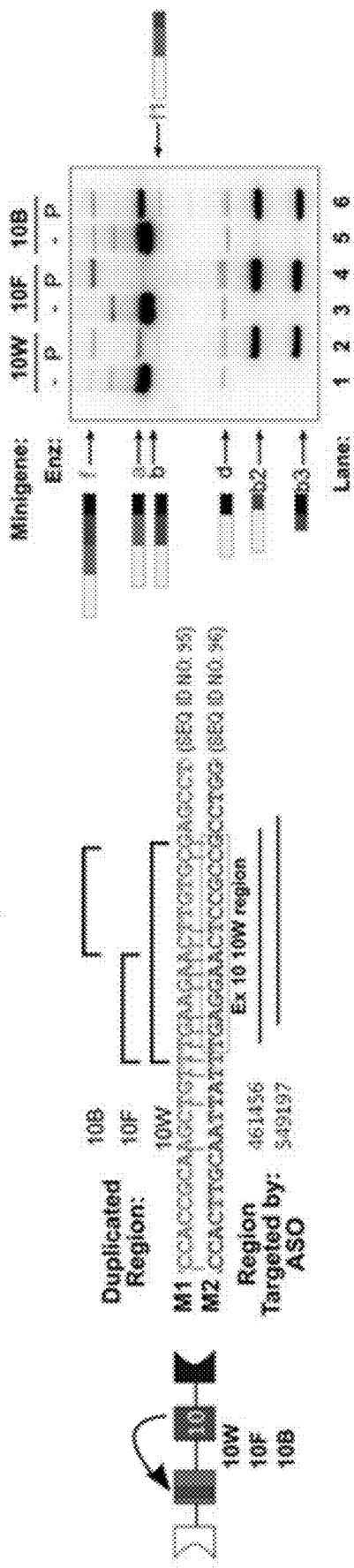

SEQUENCE LISTING

<160> NUMBER OF SEQ ID NOS: 99

<210> SEQ ID NO 1
<211> LENGTH: 33115
<212> TYPE: DNA
<213> ORGANISM: Homo sapines

<400> SEQUENCE: 1

```
acgcacaagt ctgcagctct ccccaacttt ccgttcagct cagtctccga gggtgcgcca      60
gagcagacac ccggaggagt ggggagtggc agggcgggc cgggagaatg ctgccccgga     120
acccataaat ctgggccctg cccaggtagg ccggacagc tggggtggcc tgggccgaga     180
gccaagaaaa gacaccccat ctggcagccc aacttggcgg caacaggtgg cccggcgccc     240
gggggtctgg gaggaaagtc gctccggggg cgggccccgt tgccccgccg cgtcccatt     300
ggtcatcagg tttcttaaaa tgtgactctg aatctgtgtc cttccgccgc agaatttagt     360
cccaccgaaa gggcaacctg cccgcgcgtt ccgccgccgc cgccgcgctt cctcctgaag     420
gtgactgcgc ccgcggggac gcaggggcg gggcccgggt cgcccggagc cgggattggg     480
cagagggcgg ggcggcggag ggattgcggc ggcccgcagc gggataacct tgaggctgag     540
gcagtggctc cttgcacagc agctgcacgc gccgtggctc cggatctctt cgtctttgca     600
gcgtagcccg agtcggtcag cgccggaggt gagcggtgca ggaggctacg ccatcagtcc     660
ccaccaaggg ccagtcgccc ggctagtgcg gaatcccgc gcgccggccg gccccgggca     720
cgcaggcagg gcggcgcagg atccagggcg tctgggatgc agtggagctc agagagagga     780
gaacggctcc tcacgcctgg ggcctgctct tcagaagtcc ccagcgccgt tccttccaga     840
```

```
tcaggcgggt ccgccggctc ctttcccgcc ccagccctac ccctcattc tggtcccatc      900
ctcttcctcc tgccccaatc ctcaatgcgc ctccatcctc gcctgccttc tctcggtccc      960
tcgtgattga ttccacccct gcttcccctt tctccgcgcc gcctgttccg tgctcgtttt     1020
cccctcttcc tccttaagtc tggtccttcc accccctcct cttcaagctg tgcgtgtccc     1080
ctgattctaa tgctttctgt gtaactcatt gaaactgcgt tctggttccc ctcccgcgtc     1140
cattctccat tcatgcgcga ccgcccttcc cgcgcccag ttccctctcg ccgccctcc      1200
ccctgcttgc tggtcacgtc cgctcccccg catcccttc ctcgcctggc gtgtccgctc     1260
cctccctccc tctctgctct ggtcgcgccc gcccacttgc tccggtctcc gagcgcggtc     1320
ccacccccct tttccatcac cgcctcccag ctcccagcag gctcgggcgg tgctgaggcc     1380
ccgtgtccgg ggcgggcggg cggagggctg ggctgggtgc cccgcgcggc gggcgggatg     1440
cggcggcccg ggggcagctg gagacttacg taacgttggc ctgccccgct gccgggaggc     1500
agggcggttg cccctgcggc gcggtgccgt ccctgtggc cggattaga tgggcggcct      1560
gcgagggcct gggaatggct cggggcccga gagctcgacc ggcccttgcc gggtggccgc     1620
cagggaccac gctccatctc gccgcggccg ggctgcacgt agcggccgcg cccagggccc     1680
accccgcttc accgggcgat ggccttgggc ctcgtaacgg gcgggataaa cctctgcagg     1740
ctttgctggg gcctcctggc cctcgcccgt tccgcgcctc tccggcacgt ttctttcttt     1800
tcctttcttt tttctttctt tttttttttt ttaattatcc ggcacatttt ttaacaaatg     1860
cgtcctgatt gtggaacgcg gaggccgcgg ggtggggtgg ggatctggtt acggaggggg     1920
caggaaatct gtcgcgttca ctgaacgcaa acggtgtggg tcaagggctg tttgggggtc     1980
agagttagag accaggatga ctagacgagt catagcccac cgagctcaca atcttaaaat     2040
gtatctcctg taatgctggg agtggggtac gagcttcctg ctgtgggagg gaggggaca      2100
ggaagcctcg taaggtctca ccaggtggca agcacactgg attagaagat gcaggaaagc     2160
accttccagt ctgaagatca tttaaagact cagtcatgta agggcatccc ttggcttctt     2220
aatctacgta ctccagaccc agggcttgga cctttgctgg tacgggttaa agtgaggccg     2280
acagtgaagg tccacgtgga gagagacatt gggaagttgt caaaaaggcg tttagaatca     2340
ggtttgactc attaatttcc tgagactctg aaggagttca gcctctacac ctcagtttcc     2400
cctgggaaaa ctgggagtaa cattttcctc atgatggttg aaaggattca tgcttacgtg     2460
gatgtggcac actcagtaag tgtctaatct ctggcgaaat acccagaaga aaagcctgtg     2520
actgaatata ttatttttga gcacaattac ttagtccaca attgagcata agggccttga     2580
tccattgtct tcctactgtc cccaaacgcc tacagctaat cgtgaggaat caggctctct     2640
gaataaccac gtgtctcctg gaaaccagtt ccccaaggga tctggtttaa tattgacaaa     2700
gtaactgata atgtaacttt ccaactctct gcttggagca gatgcttttt ggtcatctga     2760
gattgggacc tgtagacaaa ggcaggcaag gagggctga gttaagcctt tggtgttccg      2820
ctgtaagtag aatactacct accagaggaa cattccagcc cttgacttgc tctgcctgct     2880
ggtgagatta ggattggagc cagggtcagt agccccagt tggccgtctt gagggtgtgg      2940
ccactcccta ggtcacagag gagatggagg tcaggactcc cctgctgcag cgttgttagc     3000
aaataatttg ccctttggtg gcctgaggtg ctgtggggc aggagtgggc tgtcttgtgg      3060
ggaagggaaa tgtaacgtat caccaaatct gtggggagt ggggctctgt ggggaagatg      3120
actcaacctt tcaattattc tgcttttgag agaattatct tcgctgggtg agtggggaaa     3180
```

```
ctacattgtg gttcttgcag gcttaaaaag tcccttctcc cctttcagtg agtcagataa    3240
tgaagcatgc atttccccta attaaaaatg cctcaactac ggagcttgca gtgagccgag    3300
atcgcgccac tgcactccag cctgggcgac agagcgagac tccttctcaa aaaaaaaaa    3360 aaaaaaagcc acaactaatt aaaaaatgat tggtccgggt cacctggttc tctgtactgc    3420
cttaagagct taagtgtaga ctggcagagc ccggtgccca gctaatgccg tctgtgcagc    3480
ttcattcctg gcccttttgt agcgggcaca gccgcctctc ctgggacttg attaatgatg    3540
acttaaagaa ggttcttgaa ctcatttctc agttactgac ttgagccaaa atgtatggat    3600
gttggtctcc tgtctagcac aactgctttc attttaagca ttgcattaga aataatgttg    3660
tattcatatt ttagcaaaga gcatcattag ctctttaaga accgtacccc cagtgactta    3720
gcaaatttgg tggcggtgac tctaaacagc tagcacttta tgggagttgc ttctgtgcct    3780
tgaatgttgt gacactgatg tggggtcaca ggaaaaacca ttttatttcc taaagctgtt    3840
tatttcttaa tattgaggca atggaagaaa tgaggaaacg gccgtgggca ggaaggtaga    3900
agaaaatgca gcacttacat tacaaactca ctttacttgg gttttagttt attttgcttc    3960
agttttttgt tttttttttt ttttttttt tttttttttg agatagtttt gctcttgttg    4020
cccagtctgg agtgcaatgg tgtgatctcg gctcactgca acctccacct cctgggttca    4080
agcaattctc ctgcctcagc ctcccgaagt agctggaatt acaggcactt gcaccacgcc    4140
cagctaatat ttttgtattt ttagtagaga tggggtttca ccatgttggc caggctggtc    4200
ttgaactcct gacttaggtg atccaccggc ctcggcctcc caaagtgccg ggattacggg    4260
cgtgagccac tgcacctggc ctgcttcagc ttttatgaag gcaagtcagg atgtgttatc    4320
ttggccaaga gctaagactg agaccggagt agaggaaaat gactcatttg acattaccct    4380
tctttctgaa tcactccaaa agtccacagt caaatctcaa ttagctggta taacacaaga    4440
atgcgttgac cctgtgagca gagttttatt gcatcttcaa gggtcttcgt gagattggtt    4500
tatttggtat gaggtcttaa ggattttaag ttgtcccttt aagcatcagt tctgatacag    4560
atgggaatag agctaaacaa ccagatatat gaagaccatt tttgatacca ccatacttgc    4620
ggggagcttg cattttttta ccaaggggca gactggataa ttgagtaatt taaatacttg    4680
ggactttgtt aaagaagctg ttgggggaag gtgagcctgg gtgagtggtg gagggtgatg    4740
tgcagcatct gctgggcctt cctgcctctt ggtatgactg ctcagctcag gagttgggtg    4800
ctttagggcc cctaccatgc agtgcggtga agccccgccc ctgcagtggt tgtgcttgt    4860 ctgcacgtag gagggaacaa gccggctgca gtaccttcgg tggcctctga gactcacctc    4920
ccccacttct gtccatagac aaagctcctg gggagcccta agcctctttc ctcatgccag    4980
caagcagtct tggaagcagg ctgggctgc agtgggagag atgccaagac cagttattca    5040
agggcagtga ggttgccagt cctagcattt cacactgtgg accagcacag ctgctggctg    5100
aatactgcag tcaagattct ctgaagggag tcctatccct tccaaacatc ttcagtttac    5160
ttgcagataa tgtttcttca ttttttattt tattttattt tattttattt ttttgagacg    5220
gagtctcgca ccatgaccca ggctggagtg cagtggtgca atctcagctc actgcaagct    5280
ccgcctcccg ggttcatgcc attctcctgc ctcagcctcc tgagtagctg ggactacagg    5340
caaccgcaac cacgcctggc tgattttttt tgtatttttt agtagagacg gggtttcact    5400
gtgttagcca ggatggtctc agtctgctga cctcgtgatc cacctgtctt ggcctcccaa    5460
agtgctggga ttacaggcat cagccaccgc gcctggccat gtttcttcaa ttttaaacaa    5520
ctgatatctc ccttggccat gaacgaaaaa gaactgccca tcagtggagt cagtcagggc    5580
```

```
acataagaca cactgtgtcc accatgccat ttcagaggag atttgattga gttaagcagg    5640
gaaatagaga tgttgtaaac gttgaaacta tctgggtatc cctctttggt tattaacatt    5700
agatgagcag aaaaacaaat gtcaccgatg ggcaaacatt taaaaagtct ggcagtacca    5760
agtgtggaaa aaggtgtgga aggcagcaac tcagcgttca ttgatatagc cactttggag    5820
agcaattcag ccttatttag taaaaataga aataaacata ctccatgacc taagacttca    5880
atttctggat atatagaaac tcacacagta caggagacca tgtactacaa gagtattgat    5940
taatagaaga aacttagttt aacggggagg gagagtggcc accagtaaga cagtccataa    6000
ataaaatggt ctgttgtaca gtggactagt gtaacagctt aaatgaatta gctagatcca    6060
tatcccact ggatggatct taaatgtgct gctgagtgaa aaacaagtta ctcagtgata    6120
tatacagtat accacttagg gcattaagaa aaccacaata ttatagggtt cagtatagac    6180
atagatacac tgtacataga cttcagtgaa ctggaaggat atagagttca tgacagtgat    6240
tgggtgtcaa aatgcatgat gtggctggga gcagtggctc acacctgtaa tcccagcact    6300
ttgagaggct gatgcaggag gatcacttga ggccaggagg tcgagaccag cctgggcaac    6360
atcgcaagat tccatctct atttaaataa ataaaataga aaaaaagtt taagatggag    6420
gtggaagggg ttggaggagc ttggggatgg agaaaaaatg aactgtataa aattaaaatt    6480
cttgtttttg tttttagaaa gtaaagaggg ccgggcacag tggctcatgc ctgtaatccc    6540
agcactttgg gaagctgagg tgggcggatc acgaggtcag gagattgaga ccatcctggc    6600
taacacggtg aaaccccgtc tgtactaaaa atacaaaaaa aaaaaaaaa aaaaattagc    6660
cgggcctggt ggcgggcgcc tgtagtccca gctactcagg aggctgaggc aggagaatgg    6720
cctgaacctg ggaggtggag cttgcagtga gctgagatcg cgccagtgca ctccagcctg    6780
ggcaacagag cgagactcca tctcaaaaaa aaaaaaaaaa agaaaaaaga aattaaagaa    6840
aatacagctc agcctttatt tgtgtttttt tttttttcct tttttttctga dacagagttt    6900
ttcactctgt tgcccgggct ggagggcagt ggtgcgatct ccgttcactg cagcctccac    6960
ttcctggatt caagcaattc tgtgtctcag ccacccaagt agctgggatt acaggtgcgc    7020
gcctggctaa tttttgtatg tttagtagtg atggtgtttc accatattag ccaggctggt    7080
ctcgaactct tagcctcaag tgatctgccc gcctcagcct ttcaaactgt tgggattaca    7140
ggcgtgagcc aacacagcca gccatggctc agtgttaatg gtcagttctg ggtggtagag    7200
aggcagatgt taaaactttt ttttctttaa ttcgtaacat agaagcaaac ctataaaggc    7260
tgccgtagga agaccagtca tagtaactag ttcagtgctc ttggagagtt ggcactgcct    7320
ttcctccttt atcccccga ctagaatgca gggcagccct tccagtaaat gttgagccag    7380
tgcctcactt tgctgaggcc atcacccacc ttagttgcac ttaagaggac cctaaatcag    7440
ggtcccaggt cccttgctga ttttagagtg tggatatcat acccagaaac accgccctac    7500
ttttaatcct agtaaggagg caccatgtcc caggacaact aatgcttccc ccaaaccacc    7560
tccttcaggc tgaaaccagt tctctgcact gagcagctgg gatggaacca ggaaatcctc    7620
ggcatctgag gacattgagg ggtctctgac ttagggcttc ttcacctgaa gttgagtggt    7680
ctttgaggga agtaggccca tttagcatca gctgctcttc cctattccac actctagttg    7740
gaaataggac cttaggttcc tgttgacaag tcatttactt tcagccccga agaaataaaa    7800
gagccaagat ttttttttttt tttttaaagc cagggaattt tactagaacc tacaagtggg    7860
ctcattttgt tctgtgtagc ctggtaacac catactgctt tctgctgtgg ggcctcctgg    7920
```

```
ggttaaagtg tgggcttaag acccaggtct cttagctaga agatatctta tcctctgtat   7980
cctgcaccca tatgcaaata cattattgtc attaccctta actatagatg aagatgaaca   8040
gtgcctattc cagaccttac taggttctgc tggcccgtca cccatttga tcatgttgct    8100 ggcctagttt gattagggca aatcttagaa actccatttc cattgttgag gaagagaact   8160
agagagcagg ctgacctgaa tgccagcgta tcatgatgca gactttctaa cggatgcagg   8220
tgttcggaag agttgtggat cgaaacgcct tcatgatggc ttggaggtgt aggtagcaaa   8280
ctgacgtcac aggaaggaac acaatcttgg gtacctactg gcaacgttgg agggagaaag   8340
tgagcatcag gtgccatcat tttatagttg atctatgtga tgaggttggt atcggagcat   8400
aattggtaca aaggaaaaat gacttaggca gatgcagact cacgggccag gctattttat   8460
tagggcagaa tgatttggtc cttgtggaa gaattggtgg agtgaagcgt gaatctttcc     8520
cagcacaacc caacaacagt cctggcccta agaagtggag catgggagtt gggtgtggtt   8580
cgtgcctgta gtcccagcta cttgggatgc tgaggctgga ggatcgtttg agggtgcagt   8640
gagctataat ataatataat cacaccactg cactccagcc tgggtgacag agtgaaaccc   8700
tgtctgaaaa aaaaaaaaaa gaaaaaaaaa aagttggagg gaggagtgtt gggtattttt   8760
tatgattttt gtctcctggt ttctgaagaa tggccaaaaa attgtgtctg acacaaagga   8820
aactaatata aaaagccagg agctgtctga gatgagaaag gaaagggaga ataggcact    8880 tggagctgag ctgtgattgt gcctgttcca acctgtcact ccagactaag gcctcttaga   8940
gatggtgtct cctttctcac agaggagaca tggctctgag gaagatctta ctgcaggggc   9000
tcgggctcaa gaataaggct cctggacctg ggcatggtgt gtgctgctat cagtggatac   9060
gccaggcttc cactgctggc tggaggttgg ctctgcatgt ctgtgccttc ctaggaggag   9120
gatgcaatag tgagtcagac tggcatgggt ggggccacat gtcctggcag gcactgtcca   9180
ggcagctggc atgagggaga ggagtctttc ccagaagtcc gccctgagaa accaaggctg   9240
ggctgctctc ctggagccag gggagtccag tgagtgtttt acatacaact ctaggtacgt   9300
ggttggtggg atgggcagtt tgtgctggga agaggcttgt ggaggatttt ggagaaggca   9360
ggagagctct ggccctccct gcaagggagg cttcaggtca gagcctgagg aaagacctgg   9420
gcatgagata tgaggtctct ggctgggtag agagcatgaa ggacacatga gatctggagt   9480
ctggatgaac ttgctgacaa gcaagctttt tttgactgct aatgcgtaaa tccactatag   9540
aaattttcat ttgtcatttt tgtacttatt ggcaaaaaat tagagcttat aggcatcaga   9600
tttaatttga gatagttgaa atagggtttg tgtttgaggc caatataatt ttatctgcta   9660
atggcatctc gtggacttgg aggcagccct tctgtaccag aacattgtca aaagctttta   9720
ctgtaaagct tgagaacaaa ctagtttgct ggatttgggc atgtaactaa caggtttgag   9780
gcatgggatt atcctgtgga ctttttttt ttttttttg ctttgaggtt ctgaatgtat    9840
taaggttgac cttcttaagc cgttgaaact gttctgcagt acatttgtga tgtagggcct   9900
aagacttgta tcgttttttt ttttaatca caacccagtg tacagaactt gagacatgcg    9960 tctttttctct gccaccttt aaaagcagat tattcttgaa gtgcatagag cagcaattga   10020
ttaatggaat tggtgtcttc acatttcatt tacttcctcc caacaatttt ataggatgca   10080
tataaatatt tccaaaagag gtacacataa tttcttacta taaaagtatt tttatattta   10140
tatcagtaaa tttgttaata aagaggattt ttttttttct gtaatcctac cacccccaatg  10200 acgtcctatt aaaatttcag tatatatcct cccaggtctt ttaggtatgt ttaatttggt   10260 gtccctccc cgctcccaaa aggggaggga ccaggttctt gtatagaata gtggaatgtt    10320
```

```
agtaaatcac aggtttaaag agacataaca gtggaatctc tagagcagct gtcacctgga   10380
tacctggtta ttaaggtaat ttttccatta ccccaaagag ctttagttac actcagcttt   10440
ttccttaatc cttgtgcagc tctccagggc acaccgtatt cagctctgag cggtctttgc   10500
tagtgaggcc aaggagccac cctgagccaa aaggggagca ttatgtcacc ggaagcccaa   10560
ccccagagaa ccaaaggtat gacctgatat tcagtggccc cagccaggtc tttacaggaa   10620
gaccctcata tctcaggtct aagaagagcc agctgatggt ttttaaaaag agtggaatta   10680
gttactccaa cccacttatt cagatcttat tttgttcaca atacagtccc tagattgtag   10740
gcccattgga ggccacagca aagcctttgt gttccagttg gcctgatgtg ccatctctca   10800
gtaatgttcc cttaacagcc agacttccct aagcccagct gggagctctg aaggtatgcg   10860
agccctccct caaccatgag tgtagggaaa gggaccaggg gccccaggct ttcctgtcag   10920
taatgcagaa gttcctcaga tttagggaag ggggagcaga ggcataactt tgattctgac   10980
aaagaggcat tcagagagac tgaaaggtca tttaacaaac actggaatgc ttccacatac   11040
taggtgctag gagatacaaa accatatagg tcctggaagg gaggattgat ttttcatt    11100
tggtacgtag tagatattag gggcttagga aatacacatc gaaatgaaga gtgcatttgc   11160
catgttgaac cgttagccgg tatcttattt ccccatttta aaagttttag aatctgtggt   11220
tgaggacttg tggccatcag ttttccatag ccaacagact gttcactact gccttcagag   11280
ctccttggac ctcagcgggc cttctttgga gatggcagag atggatttag atgtatactc   11340
tactcgagcc acccagagag cccacaaagt cagagatgga acagggtaaa ggagtaaggg   11400
tcatatgtgt gagatgcctt gatttggaac tttgagattt aggatgaggt ggggaagggc   11460
taaagaggag cttgttcctg agccttgctt ggccgaagca tttaggctca agcgttttag   11520
aaagagtagc ccttggtctg agaactcaag gaaacagctt tctgatgaga cgtgtagcaa   11580
gcttctggtt cacatcctta cctgatagtt cttcaaacac tgcctggtct ggttcacatc   11640
cttacctgat agttattcaa acactgcctg gaagcttctc ctgagttttt gtctctaatc   11700
agctaactaa caggctgagt gagtttagtt gtaagtcatt aatgaagaaa gcaaaggttg   11760
gggccattgt cagggttgtg acctgggcta gttaattacc tggaactgat ggtctgtgtt   11820
acagagtggt ggtatacttg tcaggcttag aaaagaaatc aggatgtgta tcaaaaatca   11880
tttggggaaa agatttgacc agcaacttta atttctctat gtttgcaact atcctgttaa   11940
tgtagttgtg ataatttcag aattatacca gtgcccttat gttatccttg ctttgcaaat   12000
tgcaaattgc tttgcgtgtc ctgacatcct tctggccaac agtagatgtg gttttaggtt   12060
tagactcctg ggatggaagc ttttgcattc aggggaatga ctttgggttt gggtgaggat   12120
tgtaaagagg caatatgggt gccccacgac aaagcagcta tttgtagctt tgtgacagct   12180
tgacatgcag agatctaggc ttatcaaggc actaagctag gagtcagttg tttgtatcac   12240
tggaagattg gttacaactt ccttcattgg aagctccttc agtgcatgtt aaatgatgtt   12300
atttatagat agggtggtga gaaagctgtc taggtagatg tcagtcagcc cagtgtaaga   12360
gagacctgct tactgtgggt gcttgggact atgtggagtg ggtgggaggt tttaacttgt   12420
tcagtaaggt cctttccatt gttcacaatc tggtgaaccc ttttctaac atgaggagca    12480
cccacataac cagatcatgt ctggcttccc tgtggcttgt gtacaaagcg tgcttattga   12540
gttaatgtgt aagcaggaga cagccttctg tgctaaatgg tatattaacc acttctcagt   12600
cttaccactc tctttcaatt tgtctcgacc caggacctca gcagccatgt cgaagcccca   12660
```

```
tagtgaagcc gggactgcct tcattcagac ccagcagctg cacgcagcca tggctgacac    12720
attcctggag cacatgtgcc gcctggacat tgattcacca cccatcacag cccggaacac    12780
tggcatcatc tgtaccattg gtgagtgggt gtgcccttc ccccaaaaaa gggcttcatg     12840
ggcagtgacc tttctctcct gaaaagagta actaaatgtc ctaacaaacc taggtgctac    12900
atgggatact acacagattc ttatgaaagg actcaggtca taggaagttg cagtaaagaa    12960
ttagtatgtg cataggatgg caaatacagt taataagaga gtattagaca tttcaaaatt    13020
gctaagatgg cgaggtatgg tggctcccag cactttggga ggccaacgtg gaggattgc    13080 ctgagcctcg aaatttgaga ccagcctgag caacttagac cctgtctctc caaaaagtga    13140 aaaaaaaaa aaaaaaatta gctgggcatg gtggcatgca cctgtagttc tggctacatg     13200
ggaggctgag acaagatca cttgagtcca ggagattgaa gttgcagtga gccatgatca     13260
caccactgca ctccagtcta ggcaacagag cgagatcctg tcttaagaaa aaaaaattgt    13320
ccgggcgcag tggcacatgc ctgtaatcca gcacttcggg aggctgaggc aggtggatca    13380
cctgaggtca ggagttcgag accagcctgg ccaacatggt gaaatcccat ctctactaaa    13440
aatacaaaaa aattagccgg gggtggtggc gggtacctat aatcccagct acttgggagg    13500
ctgaggcagg agaattgctt gaacctggga ggcggaggtt gcagtgagct gagatctgac    13560
cattgcactc cagccttggc aacaagaacg aaactctgcc tcaaaaaaaa aaggaagaaa    13620
aaagaaaaaa acatcgctaa gagtaaattt caaatgttct caccacaaaa atgttaagta    13680
tttgaagtca tggatatgtt aactaacctg atttaattat tccacattgt atccaaactg    13740
tatgtattgg attacataac tttgtaaccc aaattataaa ttaccagttt ataataaaaa    13800
ataatttgtt gcaaaagaa tccatatggt ttaggtttta tgctataggc aaaatttaga     13860
agatgttttc cttagcaggt cttttgtagga gcaacttaaa gacctaggaa agatctttct    13920
aacatgttct gtgctaccaa gattctgtgg ttggacatct ggctgggttt cagtgagggt    13980
ggagaaggct ggccaagtct taacctaggc ttttctgata cagtgggagc ctgcagaact    14040
tgaaggaaat ggtcgaagtg tcccagtaga tcaagaaagt aagctggcac ggtagtagcc    14100
ttccatgcac ttttttaaaga cttttgagct attgggagaa ggaaaagttt tcagggaaaa    14160 aaattccttta aacttaagca aacttaaatg ttttttcctttc tttgaataat taatacttgt   14220
ggctttaaaa cttttcctaa taggcccagc ttcccgatca gtggagacgt tgaaggagat    14280
gattaagtct ggaatgaatg tggctcgtct gaacttctct catggaactc atgaggtgag    14340
ctgtggctgg accctatggc cattgtgatg gcctgtagga acagggagg gggtgcagtg     14400 ttcgtttagc cacagtggac tagacaagga tgagtctgag tttcacagtc agtgtgaagt    14460
ttgtctttac tagcccatcc ctactctcct tccctcttgt cctgacaaag caactggctg    14520
agtctctttt agcaaaaagg accccctttg ttgctggctg tggttctccc acacacctct    14580 cctacccttta gcttttacaa aggaagatat ggaaaggttc tactgaaaaa ccctctaagc    14640
cttaggtgtc ctggccacag cgcttgactc tcctgtccca gggtttctgc ttcaccttgt    14700
gttgccatgg taaaccatct agcagattga ttctagctta gaaccaaaat aactgggcag    14760
gtccatgaga acgtttcca ctattctaag ttttgaggga ctgagcctaa tgcataagca     14820
ctatctgggg tgtaataccc cacttcctca gcactgtatt ctcagcctgt gccttcccag    14880
gggttctggt acattaaaat aacaccagtt agcactcttc cccaggagcc tagtaggact    14940
gtatttgtgc tgggctcttt attagctggc tttacctatg gacagaggcc ttgcccagga    15000
gccaggtagc agctgttggg atggctccat tcctgcctcc attgccagat ttagaattaa    15060
```

```
cccattctga ggagcttggg gttccctgag gtaccatgac ttatttattt ttttatttta   15120
taaaacaaaa ttttgctctg tcatccaggc tggactgcag tggtatgatt atggctaact   15180
ggatccttga cctcccaggt tcaagtgatc ctcttgcctc agcctcccga gtagctggga   15240
atacaggcat gcaccaccac acctggctaa tttaaaaatt ttttgggggg aaatgaggtc   15300
tcactatatt gccttggctg gtctcaaact cctgggctca agtgattctc tcaaatgttg   15360
ggattacagg aatgagctac catgctcagc ctgggattgt gccttttaa aaccttcaga    15420 cttaaccata ggtttcccat agatcatggg atttcgtaat ggcattgata agaggaatta   15480
cagaagaggc aaactttgca cctgtcttgg cttctgtatt tcctgttgag agtaaagaaa   15540
atgctatcct gtaaggccaa ttgccttaca gaggttgccc tctggcattt ggaagttggt   15600
attaagtttg gactaaaaat aaagcctcag gaaatgcaat ccaagagtga attcctcctt   15660
ttgggaaaca caagactctt catcatagat tccctaacct gtgttcataa acagcctatg   15720
gcctggctag tggctggccc ttaaatgtca tggggacctg accaagtcca gcagacatac   15780
catgtaggtt aagacatgtc cctgtacctt ttggaaaatt ctgtagtttt ccaaaagcaa   15840
ggggtcctta gcaggagtca ccgagaatta cttgttagag aattaagtgt tagcttagct   15900
tagagagagc tgaagacaat gctggaggtc tgttcgctgt tgatccctgc tgctgtagtc   15960
tgccatgggc tcctgcattc aggggaagga gcagaaatag attttaaga agttgacctt    16020 taagtaggct ttatggttcc ttcatccagt aaaataacac cacatagctc taacatggca   16080
agggcgagtg atacctgcca cacctgctgg atgagagctg gctccgattt tggtattta    16140 aactttaaga ggcttttgga gattatctct actttcactc ctattcccag attataatta   16200
agatttattt tttatttttt atctatttat tttttaaaga tgtccctctt gtgtgttcat   16260
tttgaagttt tagaccaaga tgaggttgtg tgtgggctca gcttggaaac tgatctgaaa   16320
ttattctaat ttatataatg taatgtaaac agtttcagcc ttaccatacg tcagggctat   16380
cgtttcatgt gcacctttga ctaggggctg gggcgtactt ttccagtttc tgactatttt   16440
aaatgctctt ctgagcagaa cgttgagatt actgtcttcc ctctcactct gacagaggga   16500
catcaaatgt ctgcatctga tcttttaaca gcttttttt tttgagacag aatcttgctc    16560
tgttgcccag gctggagtgc actggcacaa tctctgctca ccacaacctc tgcctcccag   16620
gttcaagcaa ttctcatacc tcagcctcct gagtagctgg gattacagac ctgtgccacc   16680
acgcccagct aattttttta tattttagt agagacgggg tttcgccatg ttggccaggc    16740
tggtcttgaa cttgtgacct caggtgatcc gactgcctcg gcctcctaaa ggcgtgagcc   16800
accacgccca gcctcttttt aacagctttg gcaactagtc ttcagccctc acttttggca   16860
gttcacatgg gcaagatgca ttcttgctga acatgtggtt ccatatgcca tgttttccag   16920
atttatttat ttatttattt atttatttag agagggagtc tcgctctgtc atccaggctg   16980
gagtgcagtg gcacgatctt ggctcactgc aacctctgcc tctgggttc aagagattct    17040 tctgcctcag cctcctaagt atctgagatt acaggcacct gccaccacac ccgactaatt   17100
tttgtatttt agtagagact tggtttcacc ttgttggcca ggctgatctc gaattcctga   17160
cctcaagtga tccatccgcc ttggcctccc aaattgctgg gattacaggc gtgagccacc   17220
acacctggcc tagaaataat gacttttaaa caacctaaat gtagagcctt ccacaggaca   17280
gcattgatgg atgctttacc acataacatc ccaataaagc cacagctgaa gtggaagact   17340
cagtacacct cccagagatg ctctaagaga ttatgatata tgacatagat ttgaataata   17400
```

```
tacctaataa ttggtatgtt tataatatat ggttttacat ccccaagacc aaaaatgcat   17460
gtttgcatga aacactcatg gttacaaaaa tatattaggc caccaaaaaa accccacgt    17520 ttcataaagt agaaattata cagacacatt ctctgataaa attttttagt ggaaattaag   17580
aacaaagtca agaaaactga agtgtgctta ctttagaaag caaagatctc aaggtagatg   17640
aaataaatat ttaactcaga acactagggg aggaaaaccc taaaaagggt gaagaaaata   17700
attttgtaag attatagctc aatgaaatga aaataaattt gacagattaa gctaagagct   17760
gattctttgt ggggaaaaaa tagtaaaata gaaagttctg agaagccagg tgaagaatgc   17820
gaggatgtgc aaataagagt atgaataaaa aagagaatat ttcctacaca ttggagattt   17880
taaaagtcaa gaaagactta taacttaatt cctatataga gagatgactc tggctatttt   17940
caaagaaaag ataaatatcc aaaagataga aaatatgaat agaccagtgg ccataagaag   18000
ttgaaaaagt gggctgggcg tgcggtggct cacacctgca atcccagcac tttgggaggc   18060
caaggcggag ggatcacttg aggtcaggag ttcgagacca gcctggccaa catggtgaaa   18120
ccctgtctct actaaaaata caaaaattgg ctgggcatgg tggcacatgc ctgcagtccc   18180
agctactcgg gagcctgagg caggagaatc gcttgaacct gagaggtgga ggctacagtg   18240
agccaagatc gcgccactgc actccagcca aaaagttgaa aaagtgatta agatctggtt   18300
cacctcagaa cacttaagtc caaatgattt tagtggctga attgtctccc cttcaaagtt   18360
cagttacatt gttaaactgt tccagagcct agagaaatat agaaatcttc ccactgtgtt   18420
ctttgaaacc aatatacgct gatactgaga tcaaacaagg acagtaccaa aaccaggcag   18480
gtactaacag ttagtgtgct agaccagtct cacttagatg cagaaaacaa ataaaattta   18540
ataatccaaa tccagtagtg attgaaagga atgtcttgat ccatgaccaa gtagatttta   18600
ttctaggaga acaaaattct acatcgggat taagtagagt taaggttgac attttttttt   18660
ttttcttctg agacggagtc tcgctctgtc acccaggctg aatgcagtg gcacgatctc   18720 ggctcactgc aacctctgcc ttccgggttc acaccattct cttgcctcag cctcccgagt    18780
agctgggact acaggcgcct gctaccacgc ccggctaatt ttgttttgt acttttagta    18840 gagacggggt ttcaccatgt tagccaggat ggtctcgatc tcctgacctt gtgatccccc    18900
ctcctcggcc tcccaaagtg ctgggattac aggcgtgagc cactgcgcct ggcctgagtt    18960
aaggttgact tttaaacaac ctaaatatag ctaaatatag agccttccgc aggacagcat    19020
tgatgtgtgg aactcttatc cacgtgataa catcccaaca aagccacagc tgtagtggaa    19080
ctcagtacac ctgagtctta tcattataag atgataatag gtaacattta ttagataatt    19140
accatgtact ttgtcctaat acttcatgta ttctttact cctcacgtca actctgaagg    19200
aaaggcacca cctatcccct taaaagaaaa caactattac tattcttttt ttttttttc    19260 ttttagagac ggaatctcac tctgtctgtc gcccaggctg gagtgcagtg gcacgatctc    19320
ggctcactgc aacttctgcc tcctaggttc aagtggttct cttgcctcag cctcctgaat    19380
agctgggact acaggtgcac gccaccacgc ccagctaatt tttgtatttt aagttgagac    19440
gaggtttcac catgttggcc tggttgttgt caatctcttg atctcatgat ccacccgcct    19500
tggccttcca agtgtttag atgacaggtg tgagccaccg cgcccagcct ctattctatt    19560
ctattttgtt ctatttctat tacaagccag taagcaagaa aatatcataa tttataagga    19620
accctataaa aaacagacaa gccaagggtc tgtcattagg aagtatgcct gaataagaag    19680
ctgaagattt ttagacacag gtttcaggca acactgtctt tagaggctag gctctggctc    19740
cagctccctc cagcctcctg tgaataacag gcaggcttac ttgcaggtgc cactttcctg    19800
```

```
gacagtggtg gttaaaggac aaggcccaga aagtgctgaa ttaggtgccc ttgttaccgc   19860
taatgtctta ttgatgacac tatcttagag ctcttttgac atcttggctc tgcgtctttt   19920
tttttttttt ttcttgagat agggtgttgc tttgttatcc aggccggagt gcagtggtgt   19980
gatcatggct cactgtagcc ttgacctcct agacataacc cacctcagcc tcacaagtag   20040
ctgggacccc aggcacgcac catcatgcac agttaatttt tgtgtttttt gtagagacga   20100
ggtttcgcca tgttgcccag gctcatctca aactcctggc ccaaactgtc ctcccacctt   20160
agcctcccaa agtgtttggt ttataggcat gagccactgt gcttagcctg agtccctctt   20220
ttaaacaaac aaaatggtaa atggaaagga ggaaaggctt aagaaaaaag attgaagcca   20280
ggatttgttg taagcaagga gtaataaagg gcagttcatt tagagaaagg catatgacca   20340
cctttccccc tccaatcaga atctagaaag tgattgaggc cgggcgcagt ggctcacgcc   20400
tgtaatccca gcactttggg aggccgaggt gggcggatca cgagatcagg agatcgagac   20460
catcctggct aacatggtga acccccgtct ctactaaaaa tcgaagaagt tagccaggcg   20520
tggtggtggg cgcctgcagt cccagctact cgggaggctg agaggcagga gaatggcgtg   20580
aacctgggag gtggagcttg cagtgagcct agatagtgcc actgcactcc agcctgggcg   20640
acagagcaag actctgtctc aaaaaaaaaa aaaacaaagc gattgagaaa atcaggtctg   20700 tgtgaccttta gcaatgagtt atttagcttg ggccactgtt agcttaagtc aataacttca   20760
agtttgcgtt gtagttggaa tcaatagagg aaaagctctc agcattacca catatatcag   20820
aatgtgacat tgattgccag accagcctta tccaaacaca agtcctaggc tttttgccct   20880
gtttatgagc tttatatgct gagggtattt gatgagtctt agggaaaaaa gaacagccct   20940
ggggacacag ctgctttttat gatgagacat gtttgcaccc ataccttaat gggttttggt   21000
ggcaatattc tgaaatttgc cacctacatt tcaaagattt gcccttgggt gaattagtg    21060 ctgtagtaga agtgggtgga ggctgaggag gttggattaa gcaggtagag gatttctcag   21120
tgcatggatc gtgctgagga tggagataga gctctaagac atccacgggc cttttcctgag  21180 tgatcagctt tggctcctgg gcaggggaat tggagctgga ttctagtgtg ggagcacgct   21240
tgtcatcttc cttcttttcc cccagtacca tgcggagacc atcaagaatg tgcgcacagc   21300
cacggaaagc tttgcttctg accccatcct ctaccggccc gttgctgtgg ctctagacac   21360
taaaggacct gagatccgaa ctgggctcat caagggcgtg agtattctgc ggagagcgag   21420
gggaaggctc agtaggcaat atgccccaga gacatgtcct ccaaagcgct gggttgccat   21480
gtttcttccc agtactatga aggactgcag aggagttgag gtctacaaat gaggatttat   21540
tcatcactgt aaacaatgtt gatttgatct actttgctag gaaatggtac cacaaaggaa   21600 ccttttttttt ttaccctaaa aacctaaact ttaggctttc taacttggag aaccatctct   21660 ttgtatctttt ttccccatca ttaagtagca taactgaaac atattctttt cttggattat   21720
ttccgtgaag tatacagagt tagagaataa gagcaaaaaa ctgtattact tttagcagtg   21780
acttgagcat tgttcccggg aggaaagagc ttttccattc cttctgaggt gatgctgcta   21840
ctggtgtctc cagtttggac tcttgcttac tctcttgtcc ctagagcggc actgcagagg   21900
tggagctgaa gaagggagcc actctcaaaa tcacgctgga taacgcctac atggaaaagt   21960
gtgacgagaa catcctgtgg ctggactaca agaacatctg caaggtggtg gaagtgggca   22020
gcaagatcta cgtggatgat gggcttattt ctctccaggt gaagcagaaa ggtacgtatg   22080
ggagctggag tccagttgtc taaaacagtc ttttgtctct aaacttcctt gacacaagga   22140
```

```
agatgggaag gttggttgcc tggcagtgag attgagtctg tgtgttctca ggaatccctt   22200
ttataactca tttatcctca aagataggct ttaatccagc atagttacat tcttctggtt   22260
ctggagaaca caggaacata catacatata tatatatata tacatatata tatatatata   22320
tatatatata tatatatata tatatatttg tttcgctgtg ttttgttttg ttttcaagac   22380
agagtctcgc tctgttgccc aggctggagt gcagtggcat gatcttggct cactgcaacc   22440
tctgcctcca gagttctagc tattctccta cctcagcctc ctgagtagct gggattacag   22500
gcacccgcca ccacacccgg ctaatttttt tgtatttta gtagagatgg cgttttgcca   22560
tgttggccag gctggtctca aactcctgac ctcaggtgat ctgcctgcct ggcctccca   22620 aagtcagaac agtcttaatt atccttattt atgggtgagg aaagtgaggt acagagaggt   22680
taaatggctt gcccaggatt acacagtgta gtaggttttc aactctggta aaacagctcc   22740
agcacccata atgcaccact tcccagctca ctgtccttgc gggaaaggtg cctgcttcct   22800
gttgacctgt gccctcgtgc tctgcctccc ctacttaccc ttttttcatac aggtgccgac   22860 ttcctggtga cggaggtgga aaatggtggc tccttgggca gcaagaaggg tgtgaaccttt  22920 cctggggctg ctgtggactt gcctgctgtg tcggagaagg acatccagga tctgaagttt   22980
ggggtcgagc aggatgttga tatggtgttt gcgtcattca tccgcaaggc atctgatgtc   23040
catgaagtta ggaaggtcct gggagagaag ggaaagaaca tcaagattat cagcaaaatc   23100
gagaatcatg gggggttcg gaggcaagtc cccgttgtcc ctgctccagt cccagcgcag   23160
ctctccgaag ggcatggtcc atcctgtgaa tgtctgattc ccagcccta gcccatcaga   23220 atgtagactc ccaagccagt tccaaacctg ctgaatcaga atatcttagg agagtagaag   23280
gcattatgtt ttttgtttt tgtttttttg ttttttttaa aaaaagctt cccaggtaat   23340 tgagatgctg gcagcttgac attgttccct gggcctgggg accaacattt gagagaacag   23400
ggtcactgct cacaggacca ggggccatga tgttctgttc ctgatcagaa acactaccag   23460
tgtttgctgg aatgggggga ccaggggaa agatgacagc agacacttaa gaaagggctc   23520
tttttggccc ttcctgggga gccatgtgga atttcagggc ctggtgtcca tgttaaagct   23580 tatgcctcc tggtcttcac ttagaatgca gctggctcag tgatcatgct aactctggta   23640
tggtccattc cactctcaga ggaagatgtg tggttcttct ccagtttcag attgccccaa   23700
cttagcttac cccctcccca atgctcacaa agtagagccc agtgggcatg ccaccatttt   23760
ttggcatcct gctaggaata caactcagca caactaagat gctagacaca ctcttgtgga   23820
ttagaagtgt gtttgggag ggtgggggag caaccctgtg cacccactgt agtggcctta   23880
ctgtctgagc tttgtgtaga tatcctctgt accaggcaat ttgggtcct ccccttttgcc   23940 atcctgataa gccataggct agctgaactt ggccctaggc caggcaaagc cacattccct   24000
cttgccttca gcaggttgga gtgggccacc tcaaagggca gtcctcaagt gtccttgact   24060
agatgaggcc atgggtcttt gtggtggaag cagtcatcag gcctcaggtt ccctgtcttg   24120
aagtgctgat tggaaaatgg aggccctaga gagacccta acatgcatgg gatttggaga   24180
ggagaccttg ggaatgagcc catttggatt tgccctctcc cctttcttcc gtcaatgaag   24240
catccatatt ggtgttgaag cccagcaggc agaattgttg gccccactctg ggggcctaag   24300 gtagctggac tgccttgcca tctgtgtgca cccatgatga tatcatggat gtctgtcctg   24360
gtacaaggac atctaagtta gggaatccca gggaaacttc ttgtctactg ccatacttgt   24420
ggcctctgtt ctatataacc tctctccccc caactttgtc catcaggttt gatgaaatcc   24480
tggaggccag tgatgggatc atggtggctc gtggtgatct aggcattgag attcctgcag   24540
```

```
agaaggtctt ccttgctcag aagatgatga ttggacggtg caaccgagct gggaagcctg   24600
tcatctgtgc tactcaggca tgtgcccacc cttccccaca ttctcatgtg cacactcgca   24660
tgtttgtatg ggaaagctct ggaggctgtc tgatctcttc ccatggaatt gtcgcacgta   24720
acacacagat aatcccctt ccccatgtac ctacacaaag ccatactctg tgtacctact   24780
cactatccag aggatcagct tgctgtcatt tgtctctgaa acagctcaa gctacatctc   24840 actaatgctc tgtcccctcc cagatgctgg agagcatgat caagaagccc cgccccactc   24900
gggctgaagg cagtgatgtg gccaatgcag tcctggatgg agccgactgc atcatgctgt   24960
ctggagaaac agccaaaggg gactatcctc tggaggctgt gcgcatgcag cacctggtga   25020
gttctggggc ctgccccatc ccccagggct tcggactggg cctgggatgg atgcaagctc   25080
tggtgcagag cttttaggt ttctccatcc tcttatgcac agcctttcat tatcctccaa   25140
gttacagcag caagagggtg ggggtggaag tggaggtggc ttttttttt ctcctgttct   25200 gcattcctgc ccacacccc accctccat ttccttctgc tctggaggca tcctccttca   25260
ttggacacca cacagtttat ttcacttctg acttcaaggt tgtgaattct tcccatggct   25320
taagtcctgg gatacttctg cagtgaaagg aggtcttgta cctcttcctc agagtcagaa   25380
gttctgagta ccttttgccct attctgaaaa gggctagggg ctcctgctcc cagctgccct   25440
cttcctttgg cttccaattc agttccctct gccccgcatc ctgcagacag gcgctcccgc   25500 aggggggccct tgtggacctg cactggagtc tgttgccttc actgagctgc ctgtgctggc   25560
cttgcatggt gcctgtaggg ggatttgctt tgctgtgcca ttggggtaca gctgctgctc   25620
ttactctaga ccaaaaagtc gggttgagtg actggtggca gggccacaga tagagacagc   25680 ggggaggtg gctgaccctg gcggccctgg actgagcgtc tggaggagtc gtggaggctc   25740
tttcccttct ttctcctctg agagctcgtt cttcaggctc ttccagcttg tcatgtcgag   25800
tgcctggcca ctgctcaggg ttggaggctc agtccctttg ccctgtctgt tccagctctg   25860
gagctaactc agggatccct gatcagggtt acataggttt ggtaaaatga gtgctggaaa   25920
ttaactttct cccagtagtc ttaggtcatg ctcagtgaac ttaaacttta tccagatatg   25980
gttttccttc agccttctta ttccctttct agccagtgaa agacccgctg ccctttgacc   26040
tcagcccctc caagccccca agtttaaaac gccaccccct gccaccagaa aaaacagaaa   26100 aaaaaaaaa aaaaaaaac taaacaccc atctggtctg ggcatcttcc tttccttttt   26160
cactatgtat cctgttactg ggcttaaaca gctttcagag aagagatgtc atttctatta   26220
aatgctcttt cagtagcgaa ctgagttcac acttgactaa ggatatttc cggactgtct   26280 gtcatcagca tccttagtgg gtttccccat atttaaattg gtagaggcca gggatggtgg   26340
ctcacacctg taatctcagt actttgggag gccaaggtag gtggattgct tgagctcaga   26400
agaccagcct gggcaacctg gtgaaaccct gtctctacta aaaattcaag ttagctagct   26460
gggcatggta atgcacttct gtagtcccag ctacttggag aggggtgat gctggggcag   26520 caggatcgct tgaacccagg aggttgaggt tgcagtgagc caagatggta ccagcctagg   26580
tgacaaagtg acaccctgtc tcaaaaaaga aaccaaacaa acataaaaa aaaaacaaaa   26640 aaatcggtag agagtgattt ctctcccagg cccacttaat gtagactggg cctggctgac   26700
acctcaccat tcgtgtgatg tgattgctgt tctgatgctt agatactctt ggcgcagtct   26760
cacaattgcc accatggtag gaaggtgtcc caggagacgg tgcaccttga accagtcacc   26820
actaaagtgg ctgcctttct gggtctctcc acacatcccc tctctctaat ttccctactt   26880
```

```
aatcgtgtga cttcatggtc tcaaaggagg aacagaggct gatcttgact tagatatact   26940
gaaccatgaa atcactgcat agaatgtggg gacttgaatg tgtctttggg caagtcattt   27000
aacctcttaa gacctcatct gtaaaatgga ttagatatgt ttaattatag ccttagcatt   27060
aaatattcat tgctgttatt attaagtgtc tgataagtct ctgtgtacat ggatgtaatc   27120
ttcctaactc ccattacctc catttataga tgagggttat atggccaata aagcctgggt   27180
ttgaatctag gtctactgcc tccaaagcca gtcttctctc ctgcaacatc atgctctgtc   27240
tagcaggaga tgagaacagg tctccatttg gagcctgtca gtggggtcag agactaagat   27300
tcaggctcag ggtctaaatt ccatatcctt tcttccatac cctggtgttt cctatgaaca   27360
gatagatact ttagggctgc aaggtttgga ttgcatggca ctgctcagaa gataagttac   27420
aggtctgggc taggctgtag ctgcccctcc aggtggctag accttttcctt tctgtgtcac   27480
cagttaacac tggccaacag ttccttccat taactgttca ctgctttctc ctgtgtctaa   27540
ctgatgcagt ttatgaccca taactaagag cagtaccagg tatggctctg tttcctgttc   27600
atgtcccctg tcctctgggc tgcatgcatt ccgttcttac agaaagaata cctttaacct   27660
agtacatcct gccacacatc tgcttctact gtgaaattga tgagggggta ttaccgattc   27720
ttccctcacc catcatttac tgagatgctg gtgattgcat tataatcctc taaagcttac   27780
attgtctttc tgattcttgg tcttatctga gcaagtgatc tataaataac tcagtggctt   27840
tctcatgact gttttaatta ttagatttta atcaagtgtc ttattaaata tatctgcatg   27900
cttccacagg catctgtctc ttcacatggc tgttcagtgt gcctctcaca agttagccca   27960
cgttttctgt tctcctgctt caaactcagt tgagctgcct tgctttggct ttgatcccag   28020
ctttccagcg ctgctcaatc tgttgccatg gcaggccatt ggaaaggctc agtgcatccc   28080
cgtgcctgaa gccaagtgag cgctcactcc atgcatgcat ggaggctggg caggagcctg   28140
cctaatcaac cagccatgtg aggagggagg gcctgttcct tcctgtaagc tatgtcatga   28200
ggcagcgtgg tcaagtcctc tgccagggag tggcctgggc ccagcctggg catgttttca   28260
tgccagggtg ctagagccta ctgccagatt gtctccctcc accccaatg aaaaaatcct   28320
tccagaaggg aagagccaat ttcccctgta ttggagggga agtggcagca cctcctgaag   28380
cagttggact ttcatcaccc tacctctgca tctgcctgaa ggacagattt agccaattaa   28440
cctaaggtta ccttcctctc tgataaaattc cccattctgt cttcccatgt gttgtgtctc   28500
gtttttttcc tcctccttcc ctcttccttg cccctctcc cctaaacct tacagatagc   28560
tcgtgaggct gaggcagcca tgttccaccg caagctgttt gaagaacttg tgcgagcctc   28620
aagtcactcc acagacctca tggaagccat ggccatgggc agcgtggagg cttcttataa   28680
gtgtttagca gcagctttga tagttctgac ggagtctggc aggtagggcc ctaagggcag   28740
gtaacactgt taggataacc agcctcttgc tccacctgct ctaggagaag acagccaggc   28800
ccaacctggc atctgggcac agagcctctt ctcgtctgta ggaacaccgc cagggaggtc   28860
atggcagggc aggaccaaag ggtcctgtgg ctcagtaggc acagtagatg tcacaggcac   28920
ttggtgaagg actggtttct gtggagtctt gatcttggct cagctcagaa tctccagtga   28980
ttgggctcct cttggccttt gttcccagga acatgttcct caccagctgt ccggtgactc   29040
ttcccctccc tctccttttg tgacaaagct ctgacaaagc tctgtccccc tctcgtccct   29100
ctggacggat gttgctcccc tagattgccc gtgaggcaga ggctgccatc taccacttgc   29160
aattatttga ggaactccgc cgcctggcgc ccattaccag cgaccccaca gaagccaccg   29220
ccgtgggtgc cgtggaggcc tccttcaagt gctgcagtgg ggccataatc gtcctcacca   29280
```

```
agtctggcag gtaggaggcg gcagcggctc cctggaatgc cctgctcagt ggtacctcac    29340
cttggggtc  ctgggagcag tccattgaac aatgctcagg tggcactgag ccaaggtaag    29400
acccctctgc ctgccaccttt gggcctgcag ggaaggattg agcagagccc cttccctggg   29460
cccaaaggac tctaggtagc actcataagg aatgtcagaa catttggatc aaaagcaaat    29520
ttatgctgga gatttattac ataacagtgc acaggctgac tacaaatggt tatttgatat    29580
tgaaaattta gtcctctaaa attgtaaaag ataaccactt ttgcttattc cagttactat    29640
gtgctcttta aaaatttcag ttgggaaatg aatttattta aatgctgttt actgtgcctc    29700
catttggcac actagtccct gctgttttttg agccctaaag acaaattggg ttccagctca   29760
ggagaggttg ctgtgctatc ttggctgaca ttctgtgggg cctggcagcc aggctgagga    29820
ctgtgtggcc tatgctgggc ctccaacttg ggatcccttc cttggcccag gacattgagt    29880
taatgtcctt cactctccta gttagggagt atgctccttg tccctgtcca cagggcagca    29940
agggtttcct ggaagagggg agcaaacagg cagtgcccat gcactgagga gcagcagatg    30000
ggcgtgggca gcccagagaa ccaggacaca agctctgtgc agatgccctc agcagagggc    30060
tccagcctcc cactcttggc tgaacagctc caacccgtag ggttgacctt tcttaaaagg    30120
tccagttctt gctgtttggc tattttaagc tctagtcttc tggggtttca ctcagctggt    30180
cctggcttca gcaattgctt ccctctgaag gccttgcata gaggccaagc gtgaagtgca    30240
gggacttctc tgctgtgatg tggcttaagt ttccctgaca cctgttgagt gtcctcataa    30300
cttcccttct ggtgcccctc cccagctcct gagacacagc tgcagctaca agtgtgcagt    30360
gtcagtgttc aagaaagtgc ctggcagagg ggctttagaa gggtcccctg ccttccaaag    30420
gagctttggc aggcagagct gctcctgcag caacactccc atttcctgtt cttgcctgct    30480
gagtagcacc tagatttcta agcctcatct agatactcag atttgattct gggcctttat    30540
agcccagttg ctgggactgt ttcaggagct aggggccatg tggggcaggg agagggcaca    30600
aaagtagaga agcctgatgt tgattcccag ggggctggtc agctctgcta ctgctccttg    30660
cagatgtcaa gagtcaggtg ctagtcacgt gctgcttggc ttgtcactgt cattggcagc    30720
gagaggaatg ggtgctggtg acattgggcc agggctgcct ctctgtgtca gagttcaggg    30780
tgtaggaggg gttctgccaa ccatgggctg tgtggggtaa gtgggtgagg ctgatcttgc    30840
tgggtcaagg tgatcctgag ccccttggcct gtggaatggg ggtagagggc aaatggtaac    30900
ctagcatgct gtgggggata taggatgagg ggctgcccga gcctcgggag gggtcctagg    30960
gagcagatgt tgaagaggcc agagccctca gtgagctgga tgagagggtg agctgtttga    31020
acgccctgag ggtacttcct ggggcctcgt gtaatggtct cttctgtatg tcccccatcc    31080
catctcaggt ctgctcacca ggtggccaga taccgcccac gtgcccccat cattgctgtg    31140
acccggaatc cccagacagc tcgtcaggcc cacctgtacc gtggcatctt ccctgtgctg    31200
tgcaaggacc cagtccagga ggcctgggct gaggacgtgg acctccgggt gaactttgcc    31260
atgaatgttg gtacgtggct ggagcagggg ctagagccta gaggagcttg gggatgcttg    31320
agcattggct tctgtgggac cccgaaagtt tggggaatag aaagggaac acacagacct    31380
tagtgggca aaaggcccag cgactgttcc tctcccttat tgggaatgtt cattctgaat    31440
ctctcattct ccgaagtcct aagctgagcc aggagggaaa agggtccttt gagttgtagg    31500
gctgagcaat tcagttcctc ttctcttcta gtctggggct caaagcaaaa ttgtccattt    31560
tttggcatct gctcattact gagagttttt tttgtttttt gttttttttt taaataaat    31620
```

```
tggccacagc tcctgtgctg tggggtggca tacacagatt acgtactgat gtggccattg    31680
tccctgtata aggtagggta tcatcagatg acaggaagca gctagctctg accctgggca    31740
aggctttgca ccctctccag gatagtgaat gatgtccaaa ggtccctgcc aaccctgcca    31800
tctgagtgat aaggacattt cagggccttc ctcctgtttg cctgggctgt gagtttggtg    31860
ccaccttgtg gtgtgaggaa gtagtggtca gccagcctag ttcagtactc aggctatggg    31920
gcagctgccc aggtgcaaac ctgcctggct tggcttttac tcaccaacct cccttctctt    31980
cctccaggca aggcccgagg cttcttcaag aagggagatg tggtcattgt gctgaccgga    32040
tggcgccctg ctccggctt caccaacacc atgcgtgttg ttcctgtgcc gtgatggacc     32100
ccagagcccc tcctccagcc cctgtcccac cccttcccc cagcccatcc attaggccag      32160
caacgcttgt agaactcact ctgggctgta acgtggcact ggtaggttgg gacaccaggg    32220
aagaagatca acgcctcact gaaacatggc tgtgtttgca gcctgctcta gtgggacagc    32280
ccagagcctg gctgcccatc atgtggcccc acccaatcaa gggaagaagg aggaatgctg    32340
gactggaggc cctggagcc agatggcaag agggtgacag cttcctttcc tgtgtgtact      32400
ctgtccagtt cctttagaaa aaatggatgc ccagaggact cccaaccctg gcttggggtc    32460
aagaaacagc cagcaagagt taggggcctt agggcactgg gctgttgttc cattgaagcc    32520
gactctggcc ctggccctta cttgcttctc tagctctcta ggcctctcca gtttgcacct    32580
gtccccaccc tccactcagc tgtcctgcag caaacactcc accctccacc ttccattttc    32640
ccccactact gcagcacctc caggcctgtt gctatagagc ctacctgtat gtcaataaac    32700
aacagctgaa gcacctgttt cctctctttt ctgctgggga gggggaggtg gttgaaccct    32760
gccctctgag caggctggga atggctgcag cctcgtgccc cgcagtggga gctatggtgg    32820
tgtcacctgc catcctgccc acctcctggt gcagaggcgc tgggaaagca gtagcttact    32880
atcttagggt tacaggttgc ccccttcagt gctgcgggga gactttaatg gcttacgtga    32940
accgaagatg ggaaagagca gggacaaggc ctccctccca ctctggtaga taaacccaaa    33000
ttgcaaagtg gccttggcca tggttcttcc actttggtct tcctgcatta gcgtatccct    33060 tatggggct gtaggaggag tcagctctgg gcgcctgaga ctgggtttgg ctccc          33115
```

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agaaacagcc aagggggact                                                 20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cattcatggc aaagttcacc                                                 20

<210> SEQ ID NO 4
<211> LENGTH: 15
<212> TYPE: DNA
<213> ORGANISM: Artificial Sequence

```
<220> FEATURE:
<223> OTHER INFORMATION: Synthetic oligonucleotide

<400> SEQUENCE: 4
aataattgca agtgg                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
cctcaaataa ttgca                                                    15

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
gagttcctca aataa                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 7
cggcggagtt cctca                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
ccaggcggcg gagtt                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 9
gggcgccagg cggcg                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 10
gtaatgggcg ccagg                                                    15
```

```
<210> SEQ ID NO 11
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 11
cgctggtaat gggcg                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 12
ccccactgca gcact                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 13
tatggcccca ctgca                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 14
acgattatgg cccca                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 15
tgaggacgat tatgg                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 16
cttggtgagg acgat                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide
```

```
<400> SEQUENCE: 17
ccagacttgg tgagg                                                      15

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 18
gttcctcaaa taatt                                                      15

<210> SEQ ID NO 19
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 19
agttcctcaa ataat                                                      15

<210> SEQ ID NO 20
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 20
ggagttcctc aaata                                                      15

<210> SEQ ID NO 21
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 21
cggagttcct caaat                                                      15

<210> SEQ ID NO 22
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 22
gcggagttcc tcaaa                                                      15

<210> SEQ ID NO 23
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 23
ggcggagttc ctcaa                                                      15

<210> SEQ ID NO 24
```

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 24
gcggcggagt tcctc                                                    15

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 25
ggcggcggag ttcct                                                    15

<210> SEQ ID NO 26
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 26
aggcggcgga gttcc                                                    15

<210> SEQ ID NO 27
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 27
caggcggcgg agttc                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 28
gccaggcggc ggagt                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 29
gacgattatg gcccc                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 30
```

```
ggacgattat ggccc                                            15

<210> SEQ ID NO 31
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 31
aggacgatta tggcc                                            15

<210> SEQ ID NO 32
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 32
gaggacgatt atggc                                            15

<210> SEQ ID NO 33
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 33
gtgaggacga ttatg                                            15

<210> SEQ ID NO 34
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 34
ggtgaggacg attat                                            15

<210> SEQ ID NO 35
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 35
tggtgaggac gatta                                            15

<210> SEQ ID NO 36
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 36
ttggtgagga cgatt                                            15

<210> SEQ ID NO 37
<211> LENGTH: 37
<212> TYPE: DNA
```

```
<213> ORGANISM: Artificial Sequence
<220> FEATURE:
<223> OTHER INFORMATION: Primer

<400> SEQUENCE: 37
ggggaagata tcaattcccc attctgtctt cccatgt                                    37

<210> SEQ ID NO 38
<211> LENGTH: 37
<212> TYPE: DNA
<213> ORGANISM: Artificial Sequence
<220> FEATURE:
<223> OTHER INFORMATION: Primer

<400> SEQUENCE: 38
ggggaactcg agctagacat tcatggcaaa gttcacc                                    37

<210> SEQ ID NO 39
<211> LENGTH: 110
<212> TYPE: DNA
<213> ORGANISM: Artificial Sequence
<220> FEATURE:
<223> OTHER INFORMATION: Synthetic oligonucleotide

<400> SEQUENCE: 39
ccctaaacct tacagatagc tcgtgaggct gaggcagcca tgttccaccg caagctgttt           60
gaggaactcc gccgagcctc aagtcactcc acagacctca tggaagccat                    110

<210> SEQ ID NO 40
<211> LENGTH: 110
<212> TYPE: DNA
<213> ORGANISM: Artificial Sequence
<220> FEATURE:
<223> OTHER INFORMATION: Synthetic oligonucleotide

<400> SEQUENCE: 40
ccctaaacct tacagatagc tcgtgaggct gaggcagcca tgttccaccg caagctgttt           60
gaggaacttg tgcgagcctc aagtcactcc acagacctca tggaagccat                    110

<210> SEQ ID NO 41
<211> LENGTH: 110
<212> TYPE: DNA
<213> ORGANISM: Artificial Sequence
<220> FEATURE:
<223> OTHER INFORMATION: Synthetic oligonucleotide

<400> SEQUENCE: 41
ccctaaacct tacagatagc tcgtgaggct gaggcagcca tgttccaccg caagctgttt           60
gaagaactcc gccgagcctc aagtcactcc acagacctca tggaagccat                    110

<210> SEQ ID NO 42
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 42
cccttagggc cctacctgcc agactccgtc agaactatca aagctgctgc taaacactta           60
taagaagcct ccacgctgcc catggccatg gcttccatga ggtctg                        106

<210> SEQ ID NO 43
<211> LENGTH: 88
```

<210> SEQ ID NO 43
<211> LENGTH: (not shown)
<212> TYPE: DNA
<213> ORGANISM: Artificial Sequence
<220> FEATURE:
<223> OTHER INFORMATION: Synthetic oligonucleotide

<400> SEQUENCE: 43
ttccccattc tgtcttccca tgtgttgtgt ctcgtttttt tcctcctcct tccctcttcc    60 ttgcccctc ttcccctaaa ccttacag    88

<210> SEQ ID NO 44
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 44
agtgttacct gcccttaggg ccctac    26

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
gtagggccct aagggcaggt aacac    25

<210> SEQ ID NO 46
<211> LENGTH: 27
<212> TYPE: DNA
<213> ORGANISM: Artificial Sequence
<220> FEATURE:
<223> OTHER INFORMATION: Primer

<400> SEQUENCE: 46
ggggaaggta ccactgagca gggcatt    27

<210> SEQ ID NO 47
<211> LENGTH: 37
<212> TYPE: DNA
<213> ORGANISM: Artificial Sequence
<220> FEATURE:
<223> OTHER INFORMATION: Primer

<400> SEQUENCE: 47
ggggaagata tcaattcccc attctgtctt cccatgt    37

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
ggggaggtac cactgagcag ggcatt    26

<210> SEQ ID NO 49
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 49
tcatttgctt catacagg                                                    18

<210> SEQ ID NO 50
<211> LENGTH: 110
<212> TYPE: DNA
<213> ORGANISM: Artificial Sequence
<220> FEATURE:
<223> OTHER INFORMATION: Synthetic oligonucleotide

<400> SEQUENCE: 50
atgttgctcc cctagattgc ccgtgaggca gaggctgcca tctaccactt gcaattattt     60
gaagaacttg tgcgcctggc gcccattacc agcgacccca cagaagccac              110

<210> SEQ ID NO 51
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 51
cgctgccgcc tcctacctgc cagacttggt gaggacgatt atggcccac tgcagcactt      60 gaaggaggcc tccacggcac ccacggcggt ggcttctgtg gggtcgct                108

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 52
tggacggatg ttgctcccct ag                                               22

<210> SEQ ID NO 53
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 53
ggtaccactg agcagggcat tccagggagc cgctgccgcc tcctac                    46

<210> SEQ ID NO 54
<211> LENGTH: 25
<212> TYPE: DNA
<213> ORGANISM: Artificial Sequence
<220> FEATURE:
<223> OTHER INFORMATION: Primer

<400> SEQUENCE: 54
gtagggccct aagggcaggt aacac                                            25

<210> SEQ ID NO 55
<211> LENGTH: 44
<212> TYPE: DNA
<213> ORGANISM: Artificial Sequence
<220> FEATURE:
<223> OTHER INFORMATION: Primer

<400> SEQUENCE: 55
tgccctgcca tgacctccca gacgagaaga ggctctgtgc ccag                      44

<210> SEQ ID NO 56
<211> LENGTH: 39
<212> TYPE: DNA
<213> ORGANISM: Artificial Sequence
<220> FEATURE:
<223> OTHER INFORMATION: Primer

<400> SEQUENCE: 56
acagagcctc ttctcgtctg ggaggtcatg gcagggcag                    39

<210> SEQ ID NO 57
<211> LENGTH: 82
<212> TYPE: DNA
<213> ORGANISM: Artificial Sequence
<220> FEATURE:
<223> OTHER INFORMATION: Primer

<400> SEQUENCE: 57
ggggaactcg agatggcttc taggatggca tcgatgacag gtggccaaca gatgggcatg    60
tcgaagcccc atagtgaagc cg                                      82

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
ggggaagaat tctcacggca caggaacaac acgcatg                      37

<210> SEQ ID NO 59
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 59
ccauaaucgu ccgcaccaa                                          19

<210> SEQ ID NO 60
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 60
caucuaccac uugcaauua                                          19

<210> SEQ ID NO 61
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 61
ccguggaggc cuccuucaa                                          19

<210> SEQ ID NO 62
<211> LENGTH: 19
<212> TYPE: RNA

<213> ORGANISM: Artificial Sequence
<220> FEATURE:
<223> OTHER INFORMATION: Synthetic oligonucleotide

<400> SEQUENCE: 62
cuugcaauua uuugaggaa                                                    19

<210> SEQ ID NO 63
<211> LENGTH: 26001
<212> TYPE: DNA
<213> ORGANISM: Mus musculus

<400> SEQUENCE: 63

```
gtacatgtta aattataggt atagtctata gggctagtga ttaaactaga acaaagataa          60
gatacaacct aactatgtac tcctctatac catgccgatt tctcagcaga agcaagatag         120
taggaagtta ctgtgacaca ttctgtcatc taatgagaac acttcccata gaccccattt         180
gtgtaactgt cagatcattg aagcctgcag atgaagagca attcttggct agcaccaatt         240
ctccagttta atggatattc atgtcagtct gggtccatat ccagattggc ctggagttct         300
gcctcagtcc ctaagtgtca aggtcacaga cttaagatca ccaagctttg tatctagatt         360
tgtggtgatg gtagagttca ttaatgcatg tgtgcgtgca ttcctctgtg tgtgtgtaaa         420
agaggagagg agagagaggg agggagaaaa agaatgaata tgaatctata accgaaaccc         480
tgacctgcgt gggcctagat ctgtgtggct cagactgact ttggcctctt gagcgttgga         540
attacaggtg tgagctactc tgcttgacgc acagtatgca cagtggacct caacatgagt         600
agatagataa ctgtcaccct gttgaacact atggttcttt tgtgtgtgtg tgtccaaggc         660
acaaagaggt catttcttct accccttct cttgcagaaa ggaatgattt cctccacaga         720
tataacctcc ccctccccaa cttcatgttc tttccaccat aataaccaag catttacttc         780
cctaaactaa ggggaccaag gggacttata gaagaaacta aaaaacttta tttcactaca         840
aattgcattt atgttaccct tccctctaat caaaactgac cgaaaatggg atgaaggcct         900
gtgattcaac tacaaagaag tgtctgcttg aaatggtcac acccatcttt taccaagaaa         960
aacaaaagaa caaacaaaa ccaaaaaaaa tccaaaacct aaggtacagt cttcccattt        1020
agaatgtggc aacattgtat ctgctttcaa aactctgcgg aatgaagact agtgttaaca        1080
gttgggaaat tagaaaatac tttgtaggga aaaaattgtt aatgcctcca atactacaaa        1140
tttaaataca tacacgcctg agtcaaaaac cagtgttgac tcctgcatag ataatggcta        1200
cacgtaggtc cagttctgca ctaattacct tggattggtt tgctgcgtcc aggtccaggc        1260
attttaaaag tgcaggattc gagactcaaa gtattaacat gggtccaatc tagccctcct        1320
tattaggagg tcgcgctcac gttccaaaga gagacttaag ttcttcctac ccagcctcta        1380
agtctggaac cctctaggag gcagcccaga ccttccacca ctctcttgct cccatcaccc        1440
cagcttcccg ttccgctcag cctcagaggg tgtactgggg cgggcgccgg gagggtggag        1500
agtctccggg cggggctgga ggaatgtccg tggacctata aatctgggca ccgccctggt        1560
aggccagggc agatggggag acctgggcaa aaggccaaaa agggaacatt ttgtagccga        1620
tctaaagcaa caggtggcgg tggcgcccgg gaacctaggg gtggtggtgg cggcggcggc        1680
gctggcccgg tgggcgggcc ttgctccctc accacttccc cattggtcaa caggataacc        1740
cttgagcaaa tttggtctac gatgtccttc cgccacggaa ggtagtcctc ctcaaaaggg        1800
caacctgctt gtcccgccta ccctgagctt ctctcaggag gtgcgggcgc ccgttgaga         1860
ggcggggcgc cgccggccgc agcccggatt gggcgagggg cggggctgcg gagggattgc        1920
```

```
ggcggcccgc agctgtgata accttgaggc ccagtcggcg cagccccgca cagcagcgac    1980
tcgtcttcac ttgactgacg tccgctctag gtatcgcagc aggaaccgaa gtacgcccga    2040
ggtgagcggg gagaacctaa gccatctgtc cccagagccg atgcccactg gtgtgtaacg    2100
caggcctgcc tgcccacgcg ggactcaggc gccaggcatc gagcatccca ctccggggttg   2160 gggaggagcc acacttgagt ccaagtctta atcctccaaa ttgagggtgg ccggctagct    2220
cctttcccac ggtctcattc tgctctctct tccatctcaa tctggttcca gcctcttatc    2280
ttactattgc tatcctcgcc accctgttct cgccctgctc cgatgctcgt cctcctacat    2340
ccactacgac ttacgacctt cctcttagct ctgtgccctc ataattcggt gccctcctct    2400
taatctctac ttgaaataat tccctactc acccacccc cacccccat tcagcctccg       2460 cgttcatcct cctttcaggt cagcgttctc ttcccgcgcc agtgttcgca gctcttcgtc    2520
gcccctcccc cctccgatcc ggtcacgtcc gcgccgcagc atcctttcaa cctccatatc    2580
ctcgcccctc cccctcgcag cttttcccct cccccgcat tctagtcacg tccgcggact     2640
cctcgtggtc cggtgcatgg aggtaggatg cagtcactag cggtccttgg taatgcagct    2700
acaagttacg taacttttgt attcccggtg gcctggcaag aaaggttggc cgctattgct    2760
gcctgttttg tgtgcccgca gattttggt ggtgggcacg ggccctcatt gctctcgcgc     2820
tccatcctgc ggcggagggg cggcacgtac tgcgatgcgt ctgattaatc ggtcatgctg    2880
ctcccacgtg ctggcgaggg ggagggtggg cgatcaaccc ataccgttc ccgacagaaa     2940 ctggagcccg acgctaccag aacacacata gcccacagag ctcggtctaa ttagggaagc    3000
agattttgtc aagtcagtgc tatgaggaag atggggctgc atgcacaagg tggccggcat    3060
actggttttg aaaaagccgg gcatcttcta gtctgaaggc tataaagacc cagtaaatac    3120
ccagtcatag taagataaga gctcgaccac ttttccaaa tccaggacac tggtagtttg     3180
gaaaaagtga accttatagt gaaaatccag tcgtgcatgg aggcagctag gttttggaat    3240
ccggtgtgat ctattaatat tcttaggttt ggcctctggt cctgtgtcac tccaggctgc    3300
taaattactg gtctccttgt aagtacgggc catcctcgat gtagtgacta acctcgggtg    3360
aaatatccag aagggcatgc attatatcct tttggtcaat gaatgaagta gttaccttga    3420
aggctaccaa cttgattctg tctccttact attttatgc acattagggg taagcttggg     3480
gaggcaggta ggctctgaat acccagtatg cccatggaaa caaattctct ctggaatccc    3540
gtcagtgttt acaaagtaat taatgttaca ttgcagctct cctgagaaag agctatctaa    3600
agggagaaat ctgtgcagcc tttgtctttg gctgtgaggg tagaaacaaa gaaacaggta    3660
cccagataga agccttccgg tcctcttgt tcaagtaagc ctttatgcc ttctggcttg      3720 taggaagttt ggtactgttg ccccaacagt ggggtggggg ggctcagatc aagactcaag    3780
gaagcattgt tagcaaataa tttgccctct gatggcctga ttatgctgta ggaaaggcag    3840
tgagggtgtt ctttgggaaa gtagtgtaaa ccatcaccgg gtctgggcaa gatgactcaa    3900
cctttcaact ttgcggcttt tgagaaaatt ttcttccttg ggtgagtgag gggaccacac    3960
ttgttctctg aagtgttgta aggttccctc ttttttagtg agtcaaatag cgtgcatttt    4020
ccctgaatta aacatgtctc actcagactg agtgtggtgg ttcagcttta atcccagtac    4080
ttgggaggaa ggcctgtgag cttgagaaca tggagcgggt gataccctgt tccagaggt     4140 ggcgggtatc acctaaatga aggtgaccat aagagtggaa atgtgagtg gctgcttcta     4200 gacggcatat tttcattctt gaatgattgg cacagcagct tttcatagaa caaccagtat    4260
```

-continued

```
ccagattggc agtttctctc gaggcatttc tgaattattg cttaagccaa actatatgaa    4320
tactaatcac ttatttagta catagctatt ttcattttaa gcattatatt ttaaattatt    4380
taatttgtag ggaaatttgt taagaactgt ttgccagcac tcaggaggca gaggcatgca    4440
gatctgagtt tgaggccagc ctactctaca aagtaccaag acatccagag ctacacagaa    4500
accctatttt gggagtgggc tttggtggaa atgtatctca accaggtata atggcccttg    4560 atcccttat tcccggtgtt ctggaggcaa actggcaaat gactttgagt ttagtccagc     4620
cagtgagtga cttggcacat ttcatagctg actccaaaca gatttatggg ggctgggtat    4680
gccatctgtg ttatatgaac gtgttggtca caggaaacgc tattttattt cttaaagctg    4740
ttaattgctt aatattgagt ggaagggatg aggaagcggc tatggacaga aaggtagaaa    4800
aagcgtttct tgccttaaac tcacattggg tttttagcat ctttagcttt tttgcagcaa    4860
gtcgacacga gttgggcaag aactaagctg agattgagg tagaggaaaa tgactcattt     4920
gtctttcagt ttctcaatca tctcaaatac ccacaggcaa gttaactggt gagttttttt    4980 ttttttttt ttttttactg cttctggtaa aggaccgagt catctctgta aactgcactc     5040
atggagacta taataggagt agatgactgt atgacgaaga acattcttcc tgccctggaa    5100
ctttcgtgcg tcttgaaatt tttaaccaag agccagactt actttggcta tgtagtaatc    5160
aggagaggtg agccccacgt gcatcgtggc ctgcaaaact gctggatctt aaggcctagt    5220
gtagctactc aggtttggag gtggtcccag ggcaccacca gctgtgctgt gaggccacac    5280
ccctactgtg gtttgtgcct gtctgcacgt aggagagagg tctgggctgc agtaccttaa    5340
gtggcctcta gggagctctg agcatctcct gaggcctgcc tccaaaggaa gctgtattcc    5400
ttctaaatgt gtgaataacc tttaggccat attttggcct taaagtactg gtgtctccag    5460
tgtaaaagac tttacccttt gccatgccca ctttggagga gtcaaaggtt tgatttgatg    5520
tagagaaggg ctgggtgtgg tggaatgtat ttttaatctc agagagacag gacagtcagg    5580
atttgtagag tccttgtctc aaaaaaacaa agtagggaag gggctggcaa tgtagatctg    5640
atacaaagcc atggtccatc cctactacta cataaaatgc acatagtagc acgtgtctgt    5700
aatcatactg agcaaaggac agtgggattg agaagttgt gagttggaaa aaacaaaatg     5760
gactatgaac tgaataaagt cagaatgcta tttaattaag ttttggaaac tataaagata    5820
aaaagtcagt gttgatgcta agttctgggt gggagaaatg gagtctttag atcccactcc    5880
ttggggaaaa ggcggtcgtg caagcctgcg ggcagaagta gtaagtaggt cagtgctctt    5940
ggacagctgg tgctgccttc cttccgactt taatcaccct gccccaact gtggctccgg     6000 gctgagccgg tgcctcctgt tgctgagacc attgtgcatt ctgcttacac ctggttctct    6060
gggcttctga gccagggtcc agagcatggg cagcattccc ggaaacactg gccttgctaa    6120
ggaagaccgc atgtgccaac cggacagaaa cttctgcaaa gtcacctcct tcctgctctg    6180
gctagttctc cgctctgcac agctgagcta aagccagga aatcccttgc tttgaggaaa     6240
gtaagacctt gtcttaaaaa tcaaataagc tgggccgtga ggcaggcaga tctctcagtt    6300
tgaggccagc ctggtctatt gagttccagg acagccaggg ctacacagag aaaccctgtc    6360
tggaatctga ctctcaaccc ccaaaatctc tgctcaagtg atctgtaccc ttgataccgc    6420
acatttaatt ttgttgtatg ctgggtactg tgctccaggc cttaccactt tctggggata    6480
gaactgtcac ctgctttgac cctggtgttg gcttctcatt agggtcactg atagctggac    6540
agcagccttt ctgatggatg aagtgagatg atccttggta ctggggaaag taggcttggg    6600
gtgacatcag agaaaggttg ctacaaagcc ctgttcctag gccaggctgc tttattaggg    6660
```

```
cagcaatgat ttggacctac gtgacgatgt cattggtggg gtgaggcatg accttccaag    6720
agtgttggct ctaagaagca gggtggcacc aggcattttt ggtttgggga ttttttttt     6780 ttaatgacct ttgttcctga cacgagggag atgaatgtga agggccgagg agaactgcct    6840
gagacaggaa agggcagaac caggtaatca gagccaagct gggcctgtgc atgctccaac    6900
ctacagccca actgaggcct gggctggtgt ctcctttctc acagaggggc aatggctctg    6960
aagaacatcc tgcttcaggg gctcaggttc aagagtaagg cttctgcccc agggcatggt    7020
atctactgct gtcgtgggac acaccggggtt tctgctgccg gctggaggtt ggctgtgcat   7080
gtgggtgcct cctgaggagg aggatgctgt agtgagttgg ctggcatggg tggggccgca    7140
tgtcctggca gtcactgcta tctatacaag tatttggcca ataaggcaag tcctgcccag    7200
gggcccacct taccctaagg aacaaggctg gagctgctgt cctgggccag aaaagacttc    7260
taaaagggtg ttctatttat actatactat agataggtgg ttggctggag ttgtggggct    7320
ctggaggcca tgcaatgggc agaagagctg tgggagggag ggaggggctc caggtcagag    7380
ccttgggagt gaaaatagct gggttctaag gatgaggttg gtagggggact tgaaacccct   7440 gtaaggtttg ttagaagtct gtttaattgt gtccatccat tggaacacat gtattttcat    7500
ttgtcacttt gtatatggta gcaaggtaag tctactctgc agactttagg tttaattcta    7560
gatagagaaa tgggttgtgt gtgaaatttt acctgctaaa ttgcatcctg agccctggag    7620
ggcagcagtg cttgtctgtt ggaacatcct tgttgcacaa caaagttctg tcaagcctga    7680
gaccggtcaa aacaggagaa gaaaattgca tggaactgat aggttgtggt catgaaattt    7740
ttccatggat tagccacaca cttttgggaa ggtgactttt aaagtcagtg gattaagttg    7800
cccttcctgg gtcagtgaag ctgccctgct gagcactttt gagggcatag agaacacaca    7860
tctatcacta tattttagca gggtaattct gaaggacacg gctgatgtca cagtgagctt    7920
tatagggtgc atagagataa atgtgtcatt ttcaaagact acttaattaa cagttttatt    7980
aataaaggac acgctgggca gacagaagtg tagtaagatg ctgtctcaga agagtagggc    8040
agtaacgtga tacaggctat catccaaggt ggagcagcga gggtcagtga gatagcttgg    8100
aaacacacac aggagcttgc ttctgatggc tccagtgctt ctgtccccag aacctgagtg    8160
gtaggagggg agagcacagt tgtggtcctc tgatccctgc aaggtgccca ccaggtaccc    8220
cctaaaacta aatagtgaaa tttgtgtatt gggggaataa agtacttcaa gggatccagt    8280
aaagggtcac ttttaccact gggttttttt atttatatct tctccactgt atatctgttt    8340
taatgtagtt aacagcaact ttttgccttg ttattaaggt cgttaccaca aagagcttag    8400
tcatattcag ctttcacctt aatccttgta gctcttcagg gcaaagcata ctccactctg    8460
agcgatcttt ccaagtgagg ccaccaagcc acactgagtc aacaaaacag caatatgcca    8520
tcagaagccc agacccagag aaccaaaggt atgacctgat cactgggcct cactcaggca    8580
gggatttgcg agggcacact cgtgtctcag atgggaagaa cggcctggtg gctggctttt    8640
tcagtagttt tcagacactg tcctggtgtc tgtcccgctc acttgtccca tctcggacac    8700
agcaaggcct ttgtgtctca ttggcttggt gtaccatctg tactgtccct tagcggccac    8760
ttatcctaag cctggctggg agccgtgagt ttgccagttg tgtttgtttc ggccatgagt    8820
agaccaagga cctggctgcc tagggacttc tcacatttgg ggagagggaa aaccaggcag    8880
aattgatctt ggcagagacc cggagctcat ttaacaaaca aggtgctggg aggcaaggag    8940
ctaagactct ggagaagttg acatcttggt gtctgatgtg tcttgtagag ttaggaatga    9000
```

```
acaatgttgg ccactggttt cttccttcct ttaaaggttc tcaattctgc aaagaatgta    9060
gtggttgcac ccctgtaatc ccagcaccca agagctggaa catgagactg tcatcagttc    9120
aagaccagcc tgtgctacat atgataactt tgtcttaaag tttttcatat ctgcatttga    9180
agacttacag gtgtctggta cttggtcact agtgggtggc tgaagtctca ggttgcagag    9240
acagacttag gtacatactc tccaggcgtc cagaaaagcc agagttccgg gaagagtggg    9300
ggtcctcagc tgaggagaca ggggagagca aggatatgga gatactgtgg agcacaggct    9360
gaagacttta tgttcaggag tttgagagga gccttgtggc ctgaaaactc agatgagaaa    9420
gaatgtcagc ttcattcaag tctcagatag tctgcgagct atagcccaga gctctcccga    9480
gagttctgtc ctctaatcag ctgactatcc agctcagtga gcacttagtt gtaatgaagt    9540
aaaagcaaag gtcaggacag ctgttggaat tgtgacctgg gtggttaatt acctggaaca    9600
gatgttcaga ctactgggtg ctatacctat cagacagaga aagaggctcc aaatagccag    9660
acctcgggct ggggaagcta ggtctaatgt cagcccttgg aaagattaaa gatggtaact    9720
tcaaggtcag cctaggttgc acagtggatt tcaggccagt gtagagtagc tgctgtgatt    9780
ccatctccta ggttacagaa gactccttgg tgaggttata atgactttgg ggccatttca    9840
atgcccttgt gcaaaatttg cttttgtatgt cttgtaggtg gtactgtgtt tttgtttttg    9900
cttttgttta ttttttgcta aagaattatg gacttttgct tcctgcccag aagaactgtt    9960
ttgttccctg taatttggac cttactcttg tgtctgataa aagctaaaga atacatttag   10020
atagacctgg gactttggga gtaaaagaaa ggctttggga cagggtttct cttgtttgca   10080
ggaccacttt aggtttgggt gaatgagaga gtgagaccat gctgagtgcc taccaaagcc   10140
aatactggag attggacatc atgataggct tcccaagatg tttgtgtgct gacatactag   10200
ttagaacatg cgctggggg tgtttcttac tgtaactttg gaggtttcct tgtgtgggga    10260
aagtgatgtt ctttctaggg ttgatgagaa agctcttaag acaaggtgac agcccatgtg   10320
agaagcctgc ttaaactggc tcccagggtg tgtgcagtgg gtagggagtt actcttgttc   10380
accaaggtct ttgctgtttg ccaatagtca caagagccct ttgcccaatt tgagtagcac   10440
ccacataacc agcacgtgcc aggcttttat gctgcttgtg cacaaagcaa tcttattggg   10500
ttaatgtgta agcaggagac agcttcctat gccaagtgcc tcattaagca gtgcctaatc   10560
taattgcact cttcaaatct ccgggaccca ggacttcagg aaccatgccg aagccacaca   10620
gtgaagcagg gactgccttc attcagaccc agcagctcca tgcagccatg gctgacacct   10680
tcctggaaca catgtgccgc ctggacattg actctgcccc catcacggcc cgcaacactg   10740
gcatcatttg taccattggt gagtgtggcc ctccttcctc taaatggagg cttctacctg   10800
atttgaaagg catagtaacc attgcagagc tagcctaggt tctgagtgag gcacggtcca   10860
catttctagg ggagtagagg tcttgggaat tggccatcaa gaagaattag tgtgcttttt   10920
ctgtagttgg tgaggttcag gggtggtctt tttcatgtgc tgtcaccaac agcattcggt   10980
agacagacat cttgaaggca gagaaaactg ttgccctcca cttttctggc tgaatgaggc   11040
cctgcagaat ttgtagagaa tgttagtgtt cccacataat taagaaagtg actagtacaa   11100 tagtctttc tgtactttgg aaagaccttt ctcttaattt gtgaaggtaa ttaaaagcaa    11160
aggatgaaga gttgtttaaa tgttgagcaa atttcagaca ttttcctacc tgagtcatga   11220 tttttcttcct gtggatctaa atgtttcttg atagggcctg cttcccgatc tgtggagatg   11280
ctgaaggaga tgattaagtc tggaatgaat gtggctcggc tgaatttctc tcatggaacc   11340
catgaggtga gcgtcaacga gatccaggag actcagcgat tccttaacag tcgtactgca   11400
```

```
ggcaggtgtg agtccagggg tcccagtgaa cggaacattg ccgtttctct cttctaactt   11460
cactggaata gaaacctggc ctgctttgtc acccaccgac cagggttagc cctaccgtca   11520
acctttatga aagaaggcac gtaagggttt agctggaaac cctaggccat cagatgtctt   11580
ggcccccatg cttcagggtt tttacagtgg ttcctgtgtg tgaaccaaaa ggttctgagc   11640
agatggatag ctggagtcat tttaagatct accttttaaa tacttctctc tcccctccc    11700 tccctctcga cagggtttct ctgtatagcc ctggctgtcc tggaactcac tttgtagacc   11760
aggctggcct cgaattcaga aatctacctg cctctgcctc ccgagtgctg ggattaaagg   11820
cttgtgccac caccgcccag cttttaaat actttctaac ttgactgtgg atttcctact    11880
ggtattggtg aaggagggaa ggagactcct ctctgcctct tggtttctgt gtcctattta   11940
gagtaaaagc attaaccctg tgctgttttg ccctctgacc tttggaagtt gtttggacta   12000
aaaatagatg gagaagaatg gtccaagaag tgaaccccag aacatgagaa tcttcataga   12060
ttccctaacc catattccat aaatagcttg gaggctagtg cccaaatgtc atggaacctg   12120
agatagttcc tcaggcacct aagcaatatt tgacacattc ttgctgggtg tggtggtaca   12180
agattgtggt tttgaggcca gaatggggac tatcctcagt aacatagtaa gatcttattg   12240
caaaccagga gaggtcctta ttttccaaac tctggctttc cacaggagct cccaggaaga   12300
aggtgagcct agttcagaga cagaactagg gccacttgcc atggtccttg cgagtagtgt   12360
gtttagtcag gcaaaaatag atttggaggt gctgaccttt agggctcttg agtccagtaa   12420
aataacacca tgcagcaggt ctaagagggc aggggacagt gagactgtcc agaccactgg   12480
gcaggccagc tctgccttga tttcagacta aggcattaga gattggctgt actttgaacc   12540
tttttatatc acaatataaa gcttcacaag tcagggctct tattccatgt gcaccttcag   12600
tgaggctctg ggtgatggtg gtgctggtct tggtgattcc ctggagaccg tggaaaccaa   12660
gctccttccc tctgacagga acatcagcca cctagctgca cctgatcttg acagctttgg   12720
ctgtgtctct aattcccatc tcttgctttt cacatattca agatgtgtca ttcttgctga   12780
acaggcagta ctgtactccc acactggctt ttaaacagcc taaatttaga gcctctacaa   12840
ggatagcact gatggctgcc agtcttcccc atttggttac atgccagaaa aaccacagct   12900
gtgataatgg atagcacgac ccagctccca gcagtgttac catgcagaga aggctaattc   12960
accaccagat actccaatca caatgcagct ttatatatac gaagctgaag agtgtttatt   13020
atgctcgtga atgtgctgag gtgtgtaact cagtgtgtac agccataatt cttcagtgga   13080
aattaaggga gaaatccaaa cttctagagg atctctaaag caaatgaagg cagtcggtag   13140
tcaatatttt gggatatctg gagctgggtt accgggtggt ggtcagcctt tgggcagctt   13200
cggtccttgt ggatgaatgg tggttccagc tctgccctaa caaacaggct tgcaggtgtt   13260
ttgctgtgct cagtggttca aggaccagac tcataaagtg ctgaattgaa tggtccattg   13320
tcaccagtgt cacaaggata tgcactggca acaaactatt ttgctatctt ggctctgagt   13380
cccagatagg aaagggaaaa ggtttgggga aactttatta caagtgaaga aagcaatggc   13440
ggttgcaccg gggcaggctc ctggtcggag gaagtggtta tgaaagcagg gtctgcgtga   13500
ctagagctgt ttagctcggc cattgctcac taagtcaaca gctttgagtt tgaattgcag   13560
ttgggatcga tagtgaaaac agatagaggc tgccagggca gaaatcttca aacacaaatc   13620
ctgggtcttt gcttgtcctg attagcatcc cttggtgagt cctagggaca ctgggacaac   13680
agaagggtcc cacaggatgg gtttatagtc ttcccttaa ttgattttgg tggcagtatt    13740
```

```
ctggaactgt atgagagttg gagttgatgc tgttgtgtag agggaagaat ggatattgct    13800
aaggttagga gatgggtgaa ggtcaggagt cagacatact tttttttttt tatttgctaa    13860
ttgatcatct ttagctccag ggtggggatt ggaaactgga cagggacacc tcacctgcca    13920
atctgccttt ctttctccag taccatgcag agaccatcaa gaatgtccgt gaagccacag    13980
aaagctttgc atctgatccc attctctacc gtcctgttgc ggtggctctg gatacaaagg    14040
gacctgagat ccggactgga ctcatcaagg gcgtgagtat ctagaatagc ctggtagggg    14100
gtcacacttt tgctatgtaa ataacctatt tagtctcact ctgggaaacg gtattttgt     14160 ttgttttatt tcttcctcaa tatacaaatt caggctttat agaaaggtga gaggtttctt    14220
tggactttga gccagagttg agcgccccca tcaggggcat tggcttcttc agttcacact    14280
cccatttcct gctttaatcc atagagcggc accgctgagg tggagctgaa gaagggagcc    14340
actctgaaga tcaccctgga caacgcttac atggagaagt gtgacgagaa catcctgtgg    14400
ctggactaca agaacatctg caaggtggtg gaggtgggca gcaagatcta cgtggacgat    14460
gggctcatct cactgcaggt gaaggagaaa ggtatgtctg gtacacagtc cgtggccaat    14520
gccaactcca atcccagag ctctggcaag cacagacctc gaatgtatga agatctgggt     14580
ttaatctcca gaggatcaaa agtctaaggt tattgttggt ctgcgtccct gacctgtctg    14640
aaatactgtc tcagaaaaaa ggcagatggg gctggagaga tggctcagta ctgactgatc    14700
ttccgaagat cctgagttca atatcccag taaccacatg gttgctcaca accatctata     14760
atggttgtga tgccctcttc tggtgtctaa agagagctac agcgtgtata aaaggtcttt    14820
gggccggagc aagtggggga tcctaaattc aattcccagt agccacatga tggctcacaa    14880
accatctcta cagatacagt gtacagataa aacacattaa gtaaataaat aaataaataa    14940
ataaatataa aagtctttg ggccggagca agtgggggat cctaaattca attcccagta     15000
gccacatgat ggctcacaaa ccatctctac agatacagtg tacagataaa atacattaag    15060
taagtaaata aataaataaa taaataaata ataaattttt tttaaaaaag aaagggcaa     15120 ataacccaca aaggtccagg tacctttagt cctccgtcct agcgttcggg aatcaggaag    15180
gtggagatgt ctcggtgcag catatgttag actactatta tatgccttag aatgagagtt    15240
aaagttactt attctaaata ctttgtgaca gtttgagagg gtttcctata gctagccttg    15300
aactcttgat tcttctgttt ccacctccca aatgctcaca ttaagaatat acaccaccag    15360
ctgggcatgg tggcgcacgc ctttagtccc agtactcggg aggcagagac aggcagattt    15420
ctgagttcga ggccagcctg gtctacaaag tgagttacag gacagccagg gctatacaga    15480
gaaaccctgt ctcgaaaacc aaaaagaat gtacaccacc tcgtgtggct atttatttgt     15540
ttattcatta atttgaggca aggtttccct ttgtagccct gcctgacttg gaattaactg    15600
tgtgtgtaga ccaggctggt cttgaactca aaggtctgtt tgcatttgcc tcttgtgcta    15660
ccatacctaa aactcaaatt ttcttagcag tttgtaagta agtatttata ggtgagaaaa    15720
ctgacttggc tttcctgaag tgttttgttt ggtttggttt ttgttttgtg tgtgttggag    15780
tcttaattat ggctttagag tcctcctccc tctgcttctt gtaaattgag gtggtcttct    15840
gtgatccctt tcacacaggc gctgacttcc tggtgacgga ggtggagaat ggtggctcct    15900
tgggcagcaa gaagggcgtg aacctgccgg gcgctgctgt ggatctcccc gctgtgtcgg    15960
aaaaggacat ccaggacctg aagtttgggg tggagcagga tgtggacatg gtgtttgcat    16020 cttttcatccg caaggcagcc gacgtgcatg aagtcaggaa ggtgctggga gagaagggca    16080
agaacatcaa gatcatcagc aaaatcgaga accatgaagg cgtccgcagg tgagtcctga    16140
```

```
gacccttcca ttgcccagcc cttgagaggg gtgtggccat ggtgtgtcct ggatacctgc   16200
tcagcaaaat acagcctgct gggattggtc caggcggaca tctgaatcag cattagggag   16260
gccaagtatt tttagtcatc attttgggac ccggctggat actcaagggc ctcagatgtc   16320
catgctaaag cttgaagcct tagaaatctt ctggtctgat aatggtgctg atgaggagtg   16380
gcccattcag cttcccatag agaagcatga tgcctacgta aatggaaatt aattaaggtg   16440
gcattcataa ggatgagtgg tttattgaca aatgttcata cttggctttc tccctactgc   16500
ttcccctaga actgcttctg tgggttacag tgggcttggc tctgtgtcct ttgtactggg   16560
caactgggag tctctttcta tcttgataag ccataggtgc tgatggcctt ggtatttggg   16620
gctggggagt gggtcagctc aaagggcagc agtcagtgcc cttagctaaa tgatgatcca   16680
ctttgtagaa gatccactgg cctcattctg tctttgaagt gtcgattagg gaagtacaaa   16740
acggggtggg gggtgagatg cagaccaaaa cctccctgaa atatttatta tggtgtttaa   16800
gaagtccagc cagtaaaatt gttgtgctgt gagtattatc atactgtgct gtggatgccc   16860
cctcgcctgt gtgcccctgg gtgtgacctt tgaaagcatc tctgtcggga tcccaggtac   16920
tttggttgtg cttcctgtcc tctattatct ttctcttctt taccaggttt gatgagatct   16980
tggaggccag tgatgggatc atggtggctc gtggtgacct gggcattgag attcctgcag   17040
agaaggtctt cctggctcag aagatgatga tcgggcgatg caaccgagct gggaagcctg   17100
tcatctgtgc cacacaggca tgtgctattt cattccttct gcattctcca cctaggagac   17160
ctggccttgt cctgtccttt gggcacacat agctgtgatc tgtgcacctg cacaatctta   17220
agggaattat cttggcaatt atcactgaag atggcctagg atctcattta gtgatggtct   17280
tttaccgaga gcccttgtct gtccctcct agatgctgga gagcatgatc aagaagccac   17340
gccccacccg tgctgaaggc agtgatgtgg ccaatgcagt cctggatgga gcagactgca   17400
tcatgctgtc tggagaaaca gccaaggggg actaccctct ggaggctgtt cgcatgcagc   17460
acctggtaag tcctccaagc ctaccaccaa ggcctctgca tcacccagtc ttttacctcc   17520
ctccgaccac ggccagaaga gtgaggtgtg tggagcatgc tctgcttctt gattttcacg   17580
ttgtgctctc gctgcctgcg ccccaccacg ttgtcctgct ctggcgatta ccttttccat   17640
tacgtaggcc acatctggct aaaatattaa agtcctagga cttagtcaag ggataccttc   17700
ctccctcctg aacacccaga cggcggggcg gcctctattc taaaggagcc aagagtgtgt   17760
attcttggct gttcgcctgg tttggcttct aatttgatct cttgatggtc ccatgagcag   17820
atgcttctct gcactgcagg ctgtagccat actaagctgc tttgagctgg ccttgcatgg   17880
tgcctgtcac atgggacgtc tcttgctatg ccaaacccaa tgtagggcta gaaatagctc   17940
tgggcgtggg gaatgggtgc tgaatttagc aggttctgga ctgagatta taaagacttt   18000 ctctgggcaa atctatgctc ttttgacta agtcttctgg tttcagtaag atagggtctg   18060
gaggtccagc attcagagcc tgaggcagga agatagcttg aggctaggct gggctagaat   18120
aaggcattat cttacagaaa caacagactt ccagctgacc tgactcctgc tgactgtgat   18180
gggtgaggac ccagaacttc ctgagcagag cagttagcta gggcgccagt taggaccttt   18240
ccttgcctca tgaaagcatt gttggctaac tttcttggag cttttctatt ccttttcgg    18300 ccagcaaaga accactgttc ttttgtgtc tccagttcc aataagcccc caaactgaaa    18360
gaaaaaaaag cccccttcag gattagacat cttaccttgc ttcatttgtg tacagctgtt   18420
aagtagattc catgatctac ccatggttta tctgaattgt agctgtagcc agatgtgtgc   18480
```

```
ctatattgaa acagaccagc cgttttgtag aagcttgaac tcagcttgtc tcagctggtc    18540
acctcctgat ctgattggta ttgggagctg atcttcacag cttctcagta gctagcatgc    18600
agacattcct tctccagcag tctgtgtgcc ttcctgatct acaccaaacc cccttctttt    18660
ctagtcacct gcttagttgt cttatcacct cagagtggtc aggaacaaga ccaggtagtc    18720
taaaccatgc agtcacatac atggatttat ctttgtatag ctctgggtga cttatatgac    18780
cgcaagacct tgcccaaggt ggcatttgat gagattaatt ataattaatt agtcataaca    18840
ttaaacaatt tactgccata atgaaatgtt agataaccct ctgggctcat tgatgtaatc    18900
tttgcattct cattttcttt ttaaagggaa tcacatgtga tagtgtgttt gagcacagat    18960
ttgctatcct catagggcca gccagctgtc tgtttgcacc ctgctgtagc aggtgtgggc    19020
agagtaggag ttagttctca tgtcctgccc tctctcatgc cctgcccttt cctatgaaca    19080
gacaccttag aacctcgagg ctgggattgc atggccctgc tcagaagatg agtcacagag    19140
tccgggttag actgtggctg ccccttcagg gggtgcaagc ttctctctca tcagttaaca    19200
ctcaggatag cttctcccct tcatctgttc gctgcctcct cctctgtcta actgatatag    19260
ttcatgacct gtaattaaga gctagacatc ccagctatgg tcgtttcctg ttcatgtcct    19320
ttgggctgca tgcattccat ttatttgtaa ctaaaagaat actttccact tgcaaatctg    19380
ctaatactac caataaatgt gagttattgg ttttacatct tctctatact aaaatacttg    19440
ggattgcact ctctaaaact tagattttca ttctaatgcc tggtttact tgaacagata    19500
gtctatatat aacacatttg ctgttttgta acagttttaa ttgctaagtt ttaattggtg    19560
tcttaaggca tgcatgcttt ctcaggcatc tgcctcttca cacggctgtc cactgtgttc    19620
aagtgagcca gagttggcca ctgttctgtt tagaactggc gcaccatgta actttggctc    19680
ttttgacctt tgacccagc tttcagagct gcccagatgt ttctattata accaggtgc    19740
aaggactcgc tcttgtatgt aggctaagct agatgtcttg taaccacaca gccgtgtgtg    19800
gaggggaggc ctagttcttc ctgtaagctg tgtcatgagg cagtgtggtc aagtggaagt    19860
gtggttggct ccaccttggc atctttccat gccaaggtcc tagggcctaa caatatgtcc    19920
ctgtcttagc ttcaatcaaa aacaaaagaa attgatggtg cctgcctgtt atcctagcac    19980
ttgggaggct gaggcaaaga aaatagtgat ttttgaggat aactgtggca agttcaaggc    20040
tgataggggc tatggtaaga tcccatctca aacacatggg ggtgagtccc atctcataaa    20100
cacatgggga tggggttttt tttaagaaac aaaggggaaa gtcccaaaag gataatatct    20160
ttctagaacg gaaggaactt tccttgtatt tgaacagtaa ggggaaaagg agcagcccaa    20220
aatcccacgc aaccattcca ggagcatatg ggctttgacc accctgcctc tgcatctgcc    20280
tctgcatgaa gaaagatta aacctaaacc taagggtgcc ttccttcctc tctgatgtag    20340
ttccctgtct ttccatgtgt tgtctctctt gtttttgcct ttatccctct tccttatccc    20400
tcctacccta aaccttacag atagctcggg aggctgaggc agccatgttc caccgtctgc    20460
tgtttgaaga gcttgtgcga gcctccagtc actccacaga cctcatggag gccatggcca    20520
tgggcagcgt ggaggcctct tataagtgtt tagcagcagc tttgatagtt ctcacggagt    20580
ctggcaggta gggccctaag ggcaggtatc attataggat aaccagcttc tcgcgcaact    20640
aggtccgcta tgtgcctgag cctaggcaca gcctctctcc ttcaggaaga cagccaaggt    20700
caccataggg caggaccaaa ggattcccct gggcacagtg gaagtcacag cacctggtgc    20760
aggatggttc ctgtggagtt tctaatcttg ctcagttcag aacatggagt ggctcacctt    20820
ctcctggcca ttttgtgcc cagggacatg ttccttccca gttgtctgtg actcctttcc    20880
```

```
tccctctcca tttgtgacaa agctctgaca aagccctgtc cccgtcctc gtccctctgg   20940 acggatgttg ctcccctaga ttgcccgaga ggcagaggct gccatctacc acttgcagct   21000
attcgaggaa ctccgccgcc tggcgcccat taccagcgac cccacagaag ctgccgccgt   21060
gggtgccgtg gaggcctcct tcaagtgctg cagtggggcc attatcgtgc tcaccaagtc   21120
tggcaggtag gaggcggcag tggctccctg gggatgccca cgctcagttg acacctctcc   21180
ttgaggatgc aagagtgag tggctctggg ccagtttaag gcccctggct gccactagag   21240
gattccaggc agcactcaca gatagaccaa accaactggc tggctccagt gcacgttcaa   21300
agcctgcctc acagagagct ggaacaaaca cccagtttca ccgtgattag tactgtgggg   21360
ccttttgaca gaacactgcg tggcagctgg gcatggcgga gcatgcctct aatctcagca   21420
cttgggccaa agaggtaggc gaatgtctgg atttgtagcc tgtctagtct acaaagtgag   21480
ttccatccag gacagagccc tactcacaaa atagctcagc tggtaaagtt gcttgctaca   21540
caagcttgac ccatatttgg tccccagaaa ccatggagga cggagaaggc tggccctggg   21600
tatgcgcaag ggtacacact tggaggggtc ttggtggata aaggatttgc acaatcatga   21660
ctatctgaat ttgaatctgg caccttaaag gttttttatt attactttt attttttaa    21720 agtgcacaca gaggtcacca ggaaaggtgg tctggccttt aggagcactg tcagttcttt   21780
cagaggccca acacctgcct atatatggca gctcacaact gtctgactcc agtcctgggg   21840
aaatctaatg catgtggtca gaatacccag gcagctgtag tgaatgtacg gtggagggag   21900
agagtgaggt gcccagtgtc tatctatcta tatagcacaa tagatagata aaaataccc    21960 aagtgtggtg gtgtgtgcct gtagccccag tgctcatggt gcagaggaag aaagagcaag   22020
ttgtatcaca gcctagctac agaaagccaa acacatgtaa aatcagtgtg gaggactagg   22080
cactggtctg tctccctaag gcagtgttca tgaactaagt agcagaaagc tacttaggcc   22140
tgggctgagg atggtggcct ctgtgtaagc ttggccatga atgttggtat gtagctggaa   22200
gccagggatg atggggtact gagaaatggg gacactaaaa ctatcatttt tagtcctgga   22260 gtttgaaag ctctaaaata caaggtctat gctaattctg gggtttctct gaagagttcc    22320
tggttccagc agctacctcc ttccttcaaa gcctatgtat gcaggctagc atgaagctct   22380
gctgtggaat tcctcagtcc cccgtgccta gctaattgag taatctgata gagatagaca   22440
ctatcatttg ttacaggttg agaatagggg ttccctacat tcccagggga tcttgaatgg   22500
ccagatattc ctcttaccac acctgatcac cacccagatt tctttttctt tcttttttt    22560 ttaaatttat ttatttatat gagtacacgt acttcagaca taccagaaga ggacattggt   22620
atcggatccc attacagatg gttgctggga tcccatgtgg ttgctgggaa ttgaactcag   22680
gccctctgga agagcaatca gtgctcttaa ctgctgagct atctctccag ccccagatt    22740 tcttttctt tctttttttt tttaaagatt gatttattat tatatctaag tacactgtag    22800
ctgtctgcag atgcaccaga agagggtgtc agatttcttt atggatagtt gtgagccacc   22860
atgtggttgc cgggacctga actcaggacc ttctgaagag cagtcagtgc tcccaaccac   22920
tgagctatct ctccagccct accacccaga tttctaaaac catagaaatt ctgaggtttc   22980
ttttaacatt agctgctagg actcccatag gagaacagta tagtgttatg gtgaacattg   23040
ttggcttcca gggcctggta actctgctgc tgttctttgc agaagaagtc aggagctagg   23100
cacatggtac ttggattgta aaagttgctg cagctacag gagtgggttc tgctgagatt    23160
gggccaaagc tgcctcactg ccagatggaa gggttcattt gtgggaagaa ttctaccagc   23220
```

```
catgctccta taggactgcc catactgaga gcaggataat catcttagaa aagacaggac    23280
aggtctgagg ggcaggccag accttgaaac agttgtcagt gggcaaagcc tgtggtccag    23340
agttgaatta gagggtatta cttttggctt aggcttactg aaagggtctt atgacatgtt    23400
taacggtcag tctttccaac ctgtttccat ctcaggagtg ctcaccaagt ggccaggtac    23460
cgccctcggg ctcctatcat tgccgtgact cgaaatcccc agactgctcg ccaggcccat    23520
ctgtaccgtg gcatcttccc tgtgctgtgt aaggatgccg tgctgaatgc ctgggctgag    23580
gatgtcgacc ttcgtgtaaa cttggccatg gatgttggta tgtagctgga aacaagggaa    23640
tgatgaagtg ctaataaatg gggaccctaa aactaccact tcctgaagtc atgggctggg    23700
cctatctgtt ttatcaccca gttgtaagat tagctggagc tactgtcctg agcagggtgg    23760
ggttagaggg tggggaacac aagcttttgt ggccttattc ctatatagag acaaggaggc    23820
agctgaccct gactctctag agtataaact gaatggtgtc caaaggtctc tgcattctga    23880
gttcagcctc agcccttgtt taggctagga ggcttgcacc atcttgtggt gagaagaagt    23940
aactgtcaac ctgctcccct acccagacga ggattattag ggcagttatc tgcacctgcc    24000
ttgttggatt tgtgtctggg ttgggaaaag tgccactttg tgtgatcaat taggactgtg    24060
gggctttgca gttttcctca agtgtatacc tctactcacc aacctccttt tccccccagg    24120
caaggcccga ggcttcttca agaagggaga tgtggtcatt tgtgctgaccg ggtggcgccc    24180 tggctctgga ttcaccaaca ccatgcgtgt agtgcctgta ccttgatggc cctctggagc    24240
ccctcttcta gccctgtcc cttcccctcc cctatccttt ccattaggcc agcaacgctt    24300
gtagtgctca ctctgggcca tagtgtggcg ctggtgggct gggacaccag ggaaaattaa    24360
tgcctctaaa acatgcaata gagaccagct attattcagg gccctacctg agccaggggt    24420
ggaggaggaa tgcaggactg gaaaccctga ctttatcaca gaagggcggc agcatctctg    24480
ggctttgctt ctgtagaaag ttgtcagaat tcccagccct agcctggagt caggagacag    24540
caaaagagta ggggctgagg gtgtgggggcc caggtcccca gtgtagatga cgacttctgg    24600
ccctggccct gacctgcttt cccaacagct ttggcctccc cacttcttgt gcactccact    24660
tctgtcactg cagacactcc actctccacc ttgtattctg cagagtctcc aggcctgttg    24720
ctatagtgcc cacctgaatg tcaataaaca gcagctgaag cacctgtgtt gtgttttgtt    24780
ttgttttttt ccggggggttg gtagtggtgg tcgagccctg ccctttgagc aattgagaat    24840
gacaacagcc aggaggcctg gccttgggtg ctatggatcc accagataac cttcaagcac    24900
gggaccactg gagacgccgg agactgaata ctttgggagt atataagttg cctcctgcac    24960
caaagtgcgg ctgtgtatcg ggaagctgat ccgttctatt tcagggcaaa tactagaaaa    25020
gtctgggaca ggttcagcta gcacctgaaa tggtcgaata gtgggctgat ccctgtggta    25080
gaggcctgtt gagggcgctg taggatgagt ccctgattgg atacttcaca aaaccctcag    25140
cctccataac agttaagcac aaagggtctc ttgttttcct gttgccctca ggaataaggt    25200
acatagaaac aaggtgggac ccttgtccct ggcaactccc aacagccacc tagtcagagg    25260
ctaaggcctc tgaaattgag atgttgcagc accaagagct caggttaggt aaggaggttg    25320
gaaggcggag tagaatgaag agccctgagg gaacattttg atatgaagtc ccataattga    25380
ggacccaggc cctggtttcc tcgacctcac aattttgaag acctacctgc agctgggacc    25440
catcagggcg gtctgggagc ggggaaggct ccaccaattg agccaggctc attctgcgcg    25500
agcggccaat aggcgtgtgg gggcgggcct ttccgggggt gggcggtccc cggagggcac    25560
tgggtctggc gcacggcctc gggctcccgg agaaggcgct gcgatgaccg ccctgagccg    25620
```

```
tagcgagcct gtcgaggcgg gcaggtaagg gaggcgtccc ggggctccag gtccaggagg    25680
ctgcgacgaa gggcagggcg actctgggaa tgccgcgcct aggcgccttc tgcctccgg     25740 ctgggcactt ccaaccgcag aaatttaggc ttggaccctg cgcctccgcc cggctgtgag    25800
gtgtgcgagt ctggtgcgat gtatccgatg tgtcttggtg gcttcaggcg agcggaaggc    25860
acgctccctt ctggaaatca cctcgtgtcg gccaccctcg cggtccattc atttgtgttt    25920
cattcatttc tcgccataac gaccccccag tcccggttgt ctccacacac agcctggcgc    25980
ttccctgtgg gcctctgcaa a                                              26001
```

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
tgtctggaga aacagccaag g                                              21

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
caagctcttc aaacagcaga cg                                             22

<210> SEQ ID NO 66
<211> LENGTH: 22
<212> TYPE: DNA
<213> ORGANISM: Artificial Sequence
<220> FEATURE:
<223> OTHER INFORMATION: Probe

<400> SEQUENCE: 66
agcacctgat agctcgggag gc                                             22

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
aagatgccac ggtacagatg g                                              21

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
cagacctcat ggaggccatg                                                20

<210> SEQ ID NO 69
<211> LENGTH: 21
<212> TYPE: DNA

```
<213> ORGANISM: Artificial Sequence
<220> FEATURE:
<223> OTHER INFORMATION: Probe

<400> SEQUENCE: 69
tggcaggagt gctccaccaag t                                              21

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
ggagttcctc gaatagctgc aag                                             23

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
agtcctggat ggagcagact                                                 20

<210> SEQ ID NO 72
<211> LENGTH: 20
<212> TYPE: DNA
<213> ORGANISM: Artificial Sequence
<220> FEATURE:
<223> OTHER INFORMATION: Probe

<400> SEQUENCE: 72
gctgttcgca tgcagcacct                                                 20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
gcgagcagtc tggggatttc                                                 20

<210> SEQ ID NO 74
<211> LENGTH: 17
<212> TYPE: DNA
<213> ORGANISM: Artificial Sequence
<220> FEATURE:
<223> OTHER INFORMATION: Primer

<400> SEQUENCE: 74
accccacaga agctgcc                                                    17

<210> SEQ ID NO 75
<211> LENGTH: 22
<212> TYPE: DNA
<213> ORGANISM: Artificial Sequence
<220> FEATURE:
<223> OTHER INFORMATION: Probe

<400> SEQUENCE: 75
accaagtctg gcaggagtgc tc                                              22
```

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 76
gttcctcgaa tagctgca                                                 18

<210> SEQ ID NO 77
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 77
agttcctcga atagctgc                                                 18

<210> SEQ ID NO 78
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 78
ggagttcctc gaatagct                                                 18

<210> SEQ ID NO 79
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 79
tgagcacgat aatggccc                                                 18

<210> SEQ ID NO 80
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 80
ggtgagcacg ataatggc                                                 18

<210> SEQ ID NO 81
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 81
ccagacttgg tgagcacg                                                 18

<210> SEQ ID NO 82
<211> LENGTH: 16
<212> TYPE: DNA
<213> ORGANISM: Artificial Sequence
<220> FEATURE:

<223> OTHER INFORMATION: Synthetic oligonucleotide

<400> SEQUENCE: 82
caagtggtag atggca                                                          16

<210> SEQ ID NO 83
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 83
ccaggcggcg gagttc                                                          16

<210> SEQ ID NO 84
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 84
cggcggcagc ttctgt                                                          16

<210> SEQ ID NO 85
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 85
ggcacccacg gcggca                                                          16

<210> SEQ ID NO 86
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 86
acttggtgag cacgat                                                          16

<210> SEQ ID NO 87
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 87
ggcggagttc ctcgaata                                                        18

<210> SEQ ID NO 88
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 88
cacggcggca gcttctgt                                                        18

```
<210> SEQ ID NO 89
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 89
cacccacggc ggcagctt                                                 18

<210> SEQ ID NO 90
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 90
ttggtgagca cgataatg                                                 18

<210> SEQ ID NO 91
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 91
tgccagactt ggtgagca                                                 18

<210> SEQ ID NO 92
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 92
ggtgagcacg ataatg                                                   16

<210> SEQ ID NO 93
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 93
ttggtgagca cgataatg                                                 18

<210> SEQ ID NO 94
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 94
agacttggtg agcacgat                                                 18

<210> SEQ ID NO 95
<211> LENGTH: 35
<212> TYPE: DNA
<213> ORGANISM: Artificial sequence
<220> FEATURE:
<223> OTHER INFORMATION: Synthetic oligonucleotide
```

```
<400> SEQUENCE: 95
ccaccgcaag ctgtttgaag aacttgtgcg agcct                              35

<210> SEQ ID NO 96
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 96
ccacttgcaa ttatttgagg aactccgccg cctgg                              35

<210> SEQ ID NO 97
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 97
cucgucugua ggaacaccgc cagggag                                       27

<210> SEQ ID NO 98
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 98
actccttgag gcggc                                                    15

<210> SEQ ID NO 99
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 99
aauuauuuga ggaacuccgc cgccugg                                       27
```

ANTISENSE COMPOUNDS AND USES THEREOF

STATEMENT REGARDING FEDERALLY SPONSORED RESEARCH

This invention was made with government support under grant CA013106 awarded by the National Institutes of Health. The government has certain rights in the invention.

SEQUENCE LISTING

The present application is being filed along with a Sequence Listing in electronic format. The Sequence Listing is provided as a file entitled BIOL0206USC1SEQ.txt, created Oct. 2, 2018, which is 88 Kb in size. The information in the electronic format of the sequence listing is incorporated herein by reference in its entirety.

BACKGROUND

The pyruvate kinase M (PK-M) gene has 12 exons. Exon 9 and exon 10 are alternatively spliced in a mutually exclusive fashion to give rise to the M1 and M2 isoforms of the PK-M gene. Inclusion of exon 9 and exclusion of exon 10 yields the PK-M1 isoform. Exclusion of exon 9 and inclusion of exon 10 yields the PK-M2 isoform. Exons 9 and 10 each encode a 56 amino acid segment that confers distinctive properties to the respective PK-M1 and PK-M2 isoforms. The PK-M2 isoform is expressed in a broad range of cancer cells, whereas PK-M1 is predominantly expressed in terminally differentiated tissues.

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See for example U.S. Pat. No. 7,399,845 and published International Patent Application No. WO 2008/049085, which are hereby incorporated by reference herein in their entirety.

SUMMARY

In certain embodiments, the present invention provides compounds comprising oligonucleotides. In certain embodiments, such oligonucleotides are complementary to a pyruvate kinase M (PK-M) transcript. In certain such embodiments, oligonucleotides are complementary to a target region of the PK-M transcript comprising exon 10. In certain such embodiments, oligonucleotides are complementary to a target region of the PK-M transcript comprising an intron adjacent to exon 10. In certain such embodiments, oligonucleotides are complementary to a target region of the PK-M transcript comprising an intron adjacent to exon 10 and downstream of exon 10. In certain such embodiments, oligonucleotides are complementary to a target region of the PK-M transcript comprising an intron adjacent to exon 10 and upstream of exon 10. In certain embodiments, the PK-M transcript comprises an exonic splice enhancer for exon 10. In certain embodiments, oligonucleotides inhibit inclusion of exon 10. In certain embodiments, oligonucleotides promote skipping of exon 10. In certain embodiments, oligonucleotides promote selection of exon 9. In certain embodiments, oligonucleotides promote skipping of exon 10 and promote inclusion of exon 9. In certain such embodiments, PK-M mRNA with exon 9 mRNA is increased. In certain such embodiments, PK-M mRNA with exon 10 mRNA is decreased. In certain embodiments, the PK-M2 isoform of the PK-M protein is decreased. In certain embodiments, the PK-M1 isoform of the PK-M protein is decreased.

In certain embodiments, including, but not limited to any of the above numbered embodiments, the PK-M transcript is in a human. In certain embodiments, including, but not limited to any of the above numbered embodiments, the PK-M transcript is in a mouse.

The present disclosure provides the following non-limiting numbered embodiments:

Embodiment 1

A compound comprising a modified oligonucleotide consisting of 8 to 30 linked nucleosides and having a nucleobase sequence comprising a complementary region, wherein the complementary region comprises at least 8 contiguous nucleobases and is complementary to an equal-length portion within a target region of a PK-M transcript.

Embodiment 2

The compound of embodiment 1, wherein the target region of the PK-M transcript comprises exon 10 of the PK-M transcript.

Embodiment 3

The compound of embodiment for 2, wherein the complementary region of the modified oligonucleotide is 100% complementary to the target region.

Embodiment 4

The compound of any of embodiments 1 to 3, wherein the complementary region of the modified oligonucleotide comprises at least 10 contiguous nucleobases.

Embodiment 5

The compound of any of embodiments 1 to 3, wherein the complementary region of the modified oligonucleotide comprises at least 15 contiguous nucleobases.

Embodiment 6

The compound of any of embodiments 1 to 3, wherein the complementary region of the modified oligonucleotide comprises at least 20 contiguous nucleobases.

Embodiment 7

The compound of any of embodiments 1-6, wherein the nucleobase sequence of the oligonucleotide is at least 80% complementary to the target region, as measured over the entire length of the oligonucleotide.

Embodiment 8

The compound of any of embodiments 1-6, wherein the nucleobase sequence of the oligonucleotide is at least 90% complementary to an equal-length region of the PK-M transcript, as measured over the entire length of the oligonucleotide.

Embodiment 9

The compound of any of embodiments 1-6, wherein the nucleobase sequence of the oligonucleotide is 100% complementary to an equal-length region of the PK-M transcript, as measured over the entire length of the oligonucleotide.

Embodiment 10

The compound of any of embodiments 1-9, wherein the target region is within exon 10 of the PK-M transcript.

Embodiment 11

The compound of any of embodiments 1-10, wherein the target region is within nucleobase 29153 and nucleobase 29281 of SEQ ID NO.: 1.

Embodiment 12

The compound of any of embodiments 1-10, wherein the target region is within nucleobase 29158 and nucleobase 29262 of SEQ ID NO.: 1.

Embodiment 13

The compound of any of embodiments 1-10, wherein the target region is within nucleobase 29164 and nucleobase 29188 of SEQ ID NO.: 1.

Embodiment 14

The compound of any of embodiments 1-10, wherein the target region is within nucleobase 29261 and nucleobase 29279 of SEQ ID NO.: 1.

Embodiment 15

The compound of any of embodiments 1-10, wherein the target region is within nucleobase 29168 and nucleobase 29183 of SEQ ID NO.: 1.

Embodiment 16

The compound of any of embodiments 1-15, wherein the antisense oligonucleotide comprises any one of SEQ ID NOs: 4 to 36.

Embodiment 17

The compound of any of embodiments 1-16, wherein the modified oligonucleotide comprises at least one modified nucleoside.

Embodiment 18

The compound of embodiment 17, wherein at least one modified nucleoside comprises a modified sugar moiety.

Embodiment 19

The compound of embodiment 18, wherein at least one modified sugar moiety is a 2'-substituted sugar moiety.

Embodiment 20

The compound of embodiment 19, wherein the 2'-substitutent of at least one 2'-substituted sugar moiety is selected from among: 2'-OMe, 2'-F, and 2'-MOE.

Embodiment 21

The compound of any of embodiments 17-20, wherein the 2'-substituent of at least one 2'-substituted sugar moiety is a 2'-MOE.

Embodiment 22

The compound of any of embodiments 1-18, wherein at least one modified sugar moiety is a bicyclic sugar moiety.

Embodiment 23

The compound of embodiment 22, wherein at least one bicyclic sugar moiety is LNA or cEt.

Embodiment 24

The compound of any of embodiments 18-23, wherein at least one sugar moiety is a sugar surrogate.

Embodiment 25

The compound of embodiment 24, wherein at least one sugar surrogate is a morpholino.

Embodiment 26

The compound of embodiment 24, wherein at least one sugar surrogate is a modified morpholino.

Embodiment 27

The compound of any of embodiment 1-26, wherein the modified oligonucleotide comprises at least 5 modified nucleosides, each independently comprising a modified sugar moiety.

Embodiment 28

The compound of embodiment 27, wherein the modified oligonucleotide comprises at least 10 modified nucleosides, each independently comprising a modified sugar moiety.

Embodiment 29

The compound of embodiment 27, wherein the modified oligonucleotide comprises at least 15 modified nucleosides, each independently comprising a modified sugar moiety.

Embodiment 30

The compound of embodiment 27, wherein each nucleoside of the modified oligonucleotide is a modified nucleoside, each independently comprising a modified sugar moiety

Embodiment 31

The compound of any of embodiments 1-30, wherein the modified oligonucleotide comprises at least two modified nucleosides comprising modified sugar moieties that are the same as one another.

Embodiment 32

The compound of any of embodiments 1-31, wherein the modified oligonucleotide comprises at least two modified nucleosides comprising modified sugar moieties that are different from one another.

Embodiment 33

The compound of any of embodiments 1-32, wherein the modified oligonucleotide comprises a modified region of at least 5 contiguous modified nucleosides.

Embodiment 34

The compound of embodiment 33, wherein the modified oligonucleotide comprises a modified region of at least 10 contiguous modified nucleosides.

Embodiment 35

The compound of embodiment 33, wherein the modified oligonucleotide comprises a modified region of at least 15 contiguous modified nucleosides.

Embodiment 36

The compound of embodiment 33, wherein the modified oligonucleotide comprises a modified region of at least 20 contiguous modified nucleosides.

Embodiment 37

The compound of any of embodiments 32-36, wherein each modified nucleoside of the modified region has a modified sugar moiety independently selected from among: 2'-F, 2'-OMe, 2'-MOE, cEt, LNA, morpholino, and modified morpholino.

Embodiment 38

The compound of any of embodiments 33-37, wherein the modified nucleosides of the modified region each comprise the same modification as one another.

Embodiment 39

The compound of embodiment 38, wherein the modified nucleosides of the modified region each comprise the same 2'-substituted sugar moiety.

Embodiment 40

The compound of embodiment 38, wherein the 2'-substituted sugar moiety of the modified nucleosides of the region of modified nucleosides is selected from 2'-F, 2'-OMe, and 2'-MOE.

Embodiment 41

The compound of embodiment 39, wherein the 2'-substituted sugar moiety of the modified nucleosides of the region of modified nucleosides is 2'-MOE.

Embodiment 42

The compound of embodiment 38, wherein the modified nucleosides of the region of modified nucleosides each comprise the same bicyclic sugar moiety.

Embodiment 43

The compound of embodiment 42, wherein the bicyclic sugar moiety of the modified nucleosides of the region of modified nucleosides is selected from LNA and cEt.

Embodiment 44

The compound of embodiment 38, wherein the modified nucleosides of the region of modified nucleosides each comprises a sugar surrogate.

Embodiment 45

The compound of embodiment 44, wherein the sugar surrogate of the modified nucleosides of the region of modified nucleosides is a morpholino.

Embodiment 46

The compound of embodiment 44, wherein the sugar surrogate of the modified nucleosides of the region of modified nucleosides is a modified morpholino.

Embodiment 47

The compound of any of embodiments 1-46, wherein the modified nucleotide comprises no more than 4 contiguous naturally occurring nucleosides.

Embodiment 48

The compound of any of embodiments 1-46, wherein each nucleoside of the modified oligonucleotide is a modified nucleoside.

Embodiment 49

The compound of embodiment 48 wherein each modified nucleoside comprises a modified sugar moiety.

Embodiment 50

The compound of embodiment 49, wherein the modified nucleosides of the modified oligonucleotide comprise the same modification as one another.

Embodiment 51

The compound of embodiment 50, wherein the modified nucleosides of the modified oligonucleotide each comprise the same 2'-substituted sugar moiety.

Embodiment 52

The compound of embodiment 51, wherein the 2'-substituted sugar moiety of the modified oligonucleotide is selected from 2'-F, 2'-OMe, and 2'-MOE.

Embodiment 53

The compound of embodiment 52, wherein the 2'-substituted sugar moiety of the modified oligonucleotide is 2'-MOE.

Embodiment 54

The compound of embodiment 50, wherein the modified nucleosides of the modified oligonucleotide each comprise the same bicyclic sugar moiety.

Embodiment 55

The compound of embodiment 54, wherein the bicyclic sugar moiety of the modified oligonucleotide is selected from LNA and cEt.

Embodiment 56

The compound of embodiment 50, wherein the modified nucleosides of the modified oligonucleotide each comprises a sugar surrogate.

Embodiment 57

The compound of embodiment 56, wherein the sugar surrogate of the modified oligonucleotide is a morpholino.

Embodiment 58

The compound of embodiment 56, wherein the sugar surrogate of the modified oligonucleotide is a modified morpholino.

Embodiment 59

The compound of any of embodiments 1-58, wherein the modified oligonucleotide comprises at least one modified internucleoside linkage.

Embodiment 60

The compound of embodiment 59, wherein each internucleoside linkage is a modified internucleoside linkage.

Embodiment 61

The compound of embodiment 59 or 60, comprising at least one phosphorothioate internucleoside linkage.

Embodiment 62

The compound of embodiment 60, wherein each internucleoside linkage is a modified internucleoside linkage and wherein each internucleoside linkage comprises the same modification.

Embodiment 63

The compound of embodiment 62, wherein each internucleoside linkage is a phosphorothioate internucleoside linkage.

Embodiment 64

The compound of any of embodiments 1-63 comprising at least one conjugate.

Embodiment 65

The compound of any of embodiments 1-64 consisting of the modified oligonucleotide.

Embodiment 66

The compound of any of embodiments 1-65, wherein the compound modulates splicing of the PK-M transcript.

Embodiment 67

The compound of any of embodiments 1-66, having a nucleobase sequence comprising any of the sequences as set forth in SEQ ID NOs. 4 to 36.

Embodiment 68

The compound of any of embodiments 1-66, having a nucleobase sequence comprising any of the sequences as set forth in SEQ ID NOs. 4 to 17.

Embodiment 69

The compound of any of embodiments 1-66, having a nucleobase sequence comprising any of the sequences as set forth in SEQ ID NOs. 18 to 28.

Embodiment 70

The compound of any of embodiments 1-66, having a nucleobase sequence comprising any of the sequences as set forth in SEQ ID NOs. 29 to 36.

Embodiment 71

The compound of any of embodiments 1-66, having a nucleobase sequence comprising SEQ ID NO. 32.

Embodiment 72

The compound of any of embodiments 1-66, having a nucleobase sequence comprising SEQ ID NO. 7.

Embodiment 73

The compound of any of embodiments 1-66, having a nucleobase sequence comprising SEQ ID NO. 24.

Embodiment 74

A pharmaceutical composition comprising a compound according to any of embodiments 1-73 and a pharmaceutically acceptable carrier or diluent.

Embodiment 75

The pharmaceutical composition of embodiment 74, wherein the pharmaceutically acceptable carrier or diluent is sterile saline.

Embodiment 76

A method of modulating splicing of a PK-M transcript in a cell comprising contacting the cell with a compound according to any of embodiments 1-75.

Embodiment 77

The method of embodiment 76, wherein the cell is in vitro.

Embodiment 78

The method of embodiment 76, wherein the cell is in an animal.

Embodiment 79

The method of any of embodiments 76-78, wherein inclusion of exon 9 is increased.

Embodiment 80

The method of any of embodiments 76-78, wherein exclusion of exon 10 is increased.

Embodiment 81

The method of any of embodiments 76-78, wherein inclusion of exon 10 is decreased.

Embodiment 82

The method of any of embodiments 76-78, wherein PK-M1 mRNA expression is increased.

Embodiment 83

The method of any of embodiments 76-78, wherein PK-M2 mRNA expression is decreased.

Embodiment 84

A method of modulating the expression of PK-M in a cell, comprising contacting the cell with a compound according to any of embodiments 1-75.

Embodiment 85

The method of embodiment 84, wherein PK-M1 expression is increased.

Embodiment 86

The method of embodiments 84 or 85, wherein PK-M2 expression is decreased.

Embodiment 87

The method of embodiment 84, wherein the cell is in vitro.

Embodiment 88

The method of embodiment 84, wherein the cell is in an animal.

Embodiment 89

A method of inducing apoptosis in a cell, comprising contacting the cell with a compound according to any of embodiments 1-75.

Embodiment 90

The method of embodiment 89, wherein the cell is in vitro.

Embodiment 91

The method of embodiment 89, wherein the cell is in an animal.

Embodiment 92

A method comprising administering the compound according to any of embodiments 1-67 or the pharmaceutical composition of embodiments 74 or 75 to an animal.

Embodiment 93

The method of embodiment 92, wherein the administration is intracerebroventricular.

Embodiment 94

The method of embodiment 92, wherein the administration is into the central nervous system.

Embodiment 95

The method of any of embodiments 92-94, wherein the animal has one or more symptoms associated with cancer.

Embodiment 96

The method embodiment 95, wherein the cancer is glioblastoma.

Embodiment 97

The method of embodiment 96, wherein the administration results in amelioration of at least one symptom of cancer.

Embodiment 98

The method of any of embodiments 91-97, wherein the animal is a mouse.

Embodiment 99

The method of any of embodiments 91-97, wherein the animal is a human.

Embodiment 100

A method of preventing or retarding the growth of a cancerous tumor, comprising administering the compound according to any of embodiments 1-73 or the pharmaceutical composition of embodiments 74 or 75 to an animal in need thereof.

Embodiment 101

The method of embodiment 100, wherein the animal is a mouse.

Embodiment 102

The method of embodiment 100, wherein the animal is a human.

Embodiment 103

The method of embodiment 100 to 102, wherein the cancerous tumor comprises glioblastoma.

Embodiment 104

Use of the compound according to any of embodiments 1-73 or the pharmaceutical composition of embodiments 74 or 75 for the preparation of a medicament for use in the treatment of cancer.

Embodiment 105

Use of the compound according to any of embodiments 1-73 or the pharmaceutical composition of embodiments 74 or 75 for the preparation of a medicament for use in the amelioration of one or more symptoms cancer.

Embodiment 106

The use of embodiment 104 or 105, wherein the cancer is glioblastoma.

BRIEF DESCRIPTION OF THE FIGURES

FIG. 2a: Scheme of method used to duplicate the exon 10 10W region into exon 9 in a minigene. Minigene mutant names are indicated below. The indicated exon 9 nucleotides at the top were mutated to the corresponding exon 10 sequences on the right. The ASOs that target 10W and flanking regions are indicated below.

FIG. 2b: Mutant minigenes analyzed by transient transfection into HEK-293 cells, followed by radioactive RT-PCR and restriction digest, as in FIG. 1. Constructs from FIG. 2a are labeled at the top. The labeled bands are indicated in lower case on the left and right: uncut M1 fragment (a, 481 nucleotide); uncut M2 fragment (b, 481 nucleotides); PstI-cleaved M2 5' fragment (b2, 268 nucleotides); PstI-cleaved M2 3' fragment (b3, 213 nucleotides); a spliced mRNA that skips both exons 9 and 10 (d, 314 nucleotides); an exon 9-exon 10 doubly-included mRNA expressed from the 10B minigene (lanes 5 and 6) is indicated on the left (f, 648 nucleotides). This band is sensitive to PstI (f1, 435 nucleotides).

DETAILED DESCRIPTION

Figure 1A:
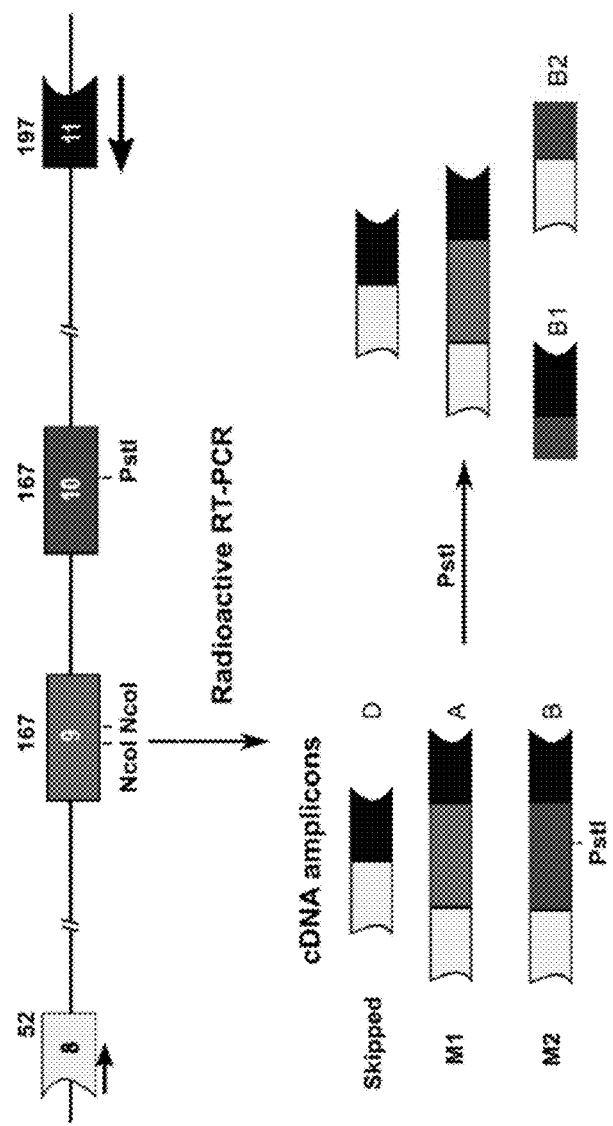
FIG. 1a: Diagram of the PK-M genomic region. This region comprises introns 8, 9, and 10 (represented by the lines) and portions of exon 8, intact exons 9 and 10, and portions of exon 11 (represented by boxes). Numbers above the boxes show the length in nucleotides. cDNA amplicons generated after radioactive RT-PCR are shown below and labeled accordingly. Three spliced species were observed: the shorter double-skipped species, comprising only exons 8 and 11 (D, 271 nucleotides); M1, including exon 9 (A, 398 nucleotides); and M2, including exon 10 (B, 398 nucleotides).

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "PK-M transcript" means a transcript transcribed from a PK-M gene. In certain embodiments, a PK-M transcript comprises SEQ ID NO: 1: the complement of GENBANK Accession No. NT_010194.16 truncated from nucleotides 43281289 to 43314403.

As used herein, "PK-M gene" means a gene that encodes a pyruvate kinase M protein and any pyruvate kinase M protein isoforms. In certain embodiments, pyruvate kinase M protein isoforms include pyruvate kinase M1 and pyruvate kinase M2. In certain embodiments, a pyruvate kinase M gene is represented by GENBANK Accession No. NT_010194.16 truncated from nucleotides 43281289 to 43314403, or a variant thereof. In certain embodiments, a pyruvate kinase M gene is at least 95% identical to GENBANK Accession No. NT_010194.16 truncated from nucleotides 43281289 to 43314403. In certain embodiments, a pyruvate kinase M gene is at least 90% identical to GENBANK Accession No. NT_010194.16 truncated from nucleotides 43281289 to 43314403.

As used herein, "PK-M1" means a pyruvate kinase M transcript that includes exon 9 but does not include exon 10.

As used herein, "PK-M1 isoform" means a pyruvate kinase M protein isoform that includes amino acids encoded from exon 9 but does not include amino acids encoded from exon 10.

As used herein, "PK-M2" means a pyruvate kinase M transcript that includes exon 10 but does not include exon 9.

As used herein, "PK-M2 isoform" means a pyruvate kinase M protein isoform that includes amino acids encoded from exon 10 but does not include amino acids encoded from exon 9.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$ —O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

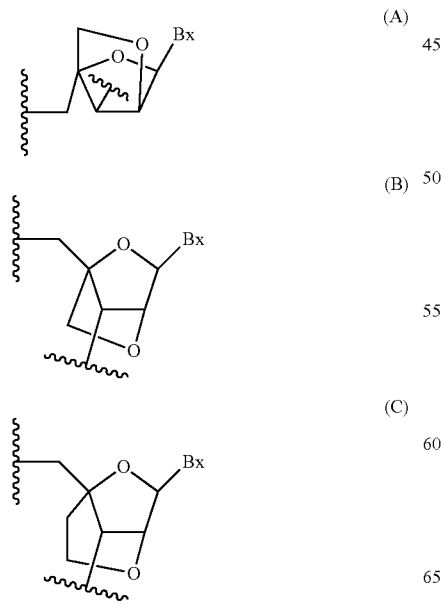

(A)

(B)

(C)

-continued

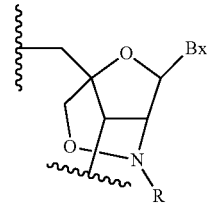

(D)

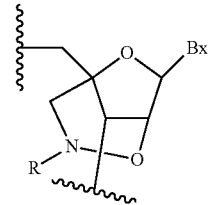

(E)

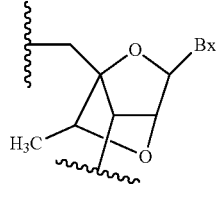

(F)

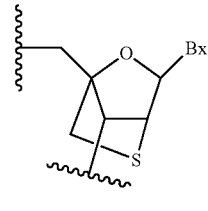

(G)

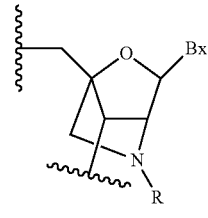

(H)

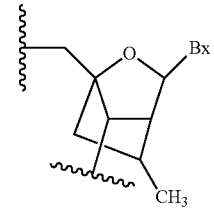

(I)

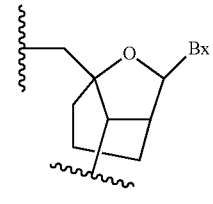

(J)

wherein Bx is a nucleobase moiety and R is, independently, H, a protecting group, or C$_1$-C$_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

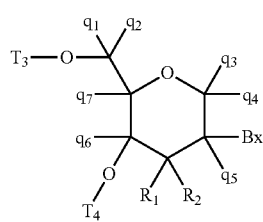

VII wherein independently for each of said at least one tetrahydropyran nucleoside analog of Formula VII:

Bx is a nucleobase moiety;

T$_3$ and T$_4$ are each, independently, an internucleoside linking group linking the tetrahydropyran nucleoside analog to the antisense compound or one of T$_3$ and T$_4$ is an internucleoside linking group linking the tetrahydropyran nucleoside analog to the antisense compound and the other of T$_3$ and T$_4$ is H, a hydroxyl protecting group, a linked conjugate group, or a 5' or 3'-terminal group;

q$_1$, q$_2$, q$_3$, q$_4$, q$_5$, q$_6$ and q$_7$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl; and each of R$_1$ and R$_2$ is independently selected from among: hydrogen, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X) NJ$_1$J$_2$, and CN, wherein X is O, S or NJ$_1$, and each J$_1$, J$_2$, and J$_3$ is, independently, H or C$_1$-C$_6$ alkyl.

In certain embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VII are provided wherein one of R$_1$ and R$_2$ is F. In certain embodiments, R$_1$ is fluoro and R$_2$ is H, R$_1$ is methoxy and R$_2$ is H, and R$_1$ is methoxyethoxy and R$_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

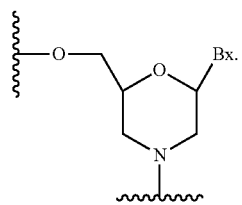

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C (O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Pathways and Mechanisms Associated with Cancer

Many cancer cells preferentially use the glycolytic pathway with lactate generation to produce energy, even under normal oxygen conditions. This metabolic feature of cancer is termed the Warburg effect. In certain embodiments, PK-M2 mediates the Warburg effect. In certain embodiments, expression of PK-M2 is crucial for tumor cell growth and proliferation.

In certain embodiments, reducing expression of PK-M2 inhibits cancer growth. In certain embodiments, reducing expression of PK-M2 induces apoptosis in a cell. In certain embodiments, the cell is a cancer cell. In certain embodiments, the cell is a tumor cell. In certain imbodiments, the cell is a glioblastoma cell.

In certain embodiments, increasing inclusion of exon 9 of a PK-M transcript inhibits cancer growth. In certain embodiments, increasing exclusion of exon 10 of a PK-M transcript inhibits cancer growth. In certain embodiments, increasing inclusion of exon 9 of a PK-M transcript induces apoptosis in a cell. In certain embodiments, increasing exclusion of exon 10 of a PK-M transcript induces apoptosis in a cell. In certain embodiments, the cell is a cancer cell. In certain embodiments, the cell is a tumor cell. In certain imbodiments, the cell is a glioblastoma cell. In certain embodiments, the downregulation of PK-M2 leads to apoptosis in certain cancer cells. In certain embodiments, the downregulation of PK-M2 leads to apoptosis in certain glioblastoma cell lines.

In certain embodiments, PK-M2 also functions as a co-activator of HIF-1 and/or β-catenin. In certain embodiments, reducing expression of PK-M2, as opposed to inhibiting its kinase function, interferes with anti-apoptotic and pro-proliferative functions associated with cancer or tumor cells. In certain embodiments, one or more antisense compounds may be used to target a PK-M2.

In certain embodiments, the administration of a modified oligonucleotide causes a switch in the alternative splicing of the PK-M transcript. In certain embodiments, the administration of a modified oligonucleotide causes increased inclusion of exon 9 mRNA of the PK-M transcript. In certain embodiments, the administration of a modified oligonucleotide causes an increase in the exclusion of exon 10 mRNA of the PK-M transcript. In certain embodiments, the administration of a modified oligonucleotide reduces expression of PK-M2 in a cell. In certain embodiments, the administration of a modified oligonucleotide reduces expression of PK-M2 in a cell and inhibits cancer growth. In certain embodiments, the administration of a modified oligonucleotide reduces expression of PK-M2 and induces apoptosis in a cell. In certain embodiments, the cell is a cancer cell. In certain embodiments, the cell is a tumor cell. In certain embodiments, the cell is a glioblastoma cell.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is a PK-M transcript. In certain embodiments, the target RNA is a PK-M pre-mRNA.

In certain embodiments, an antisense compound is complementary to a region of PK-M pre-mRNA. In certain embodiments, an antisense compound is complementary within a region of PK-M pre-mRNA comprising an exon encoding PK-M2. In certain embodiments, an antisense compound is complementary to a region of PK-M pre-mRNA comprising an intron-exon splice junction. In certain embodiments, an antisense compound is complementary to a region of PK-M pre-mRNA comprising the intron-exon splice junction adjacent to exon 10. In certain embodiments, an antisense compound is complementary within a region of PK-M pre-mRNA consisting of exon 10. In certain embodiments, an antisense compound is complementary within a region of PK-M pre-mRNA comprising an exonic splicing silencer within an exon 10. In certain embodiments, an antisense compound is complementary within a region of PK-M pre-mRNA comprising an exonic splicing enhancer within exon 10. In certain embodiments, an antisense compound is complementary within a region of PK-M pre-mRNA comprising an exonic splicing silencer within an exon 9. In certain embodiments, an antisense compound is complementary within a region of PK-M pre-mRNA comprising an exonic splicing enhancer within exon 9.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of a PK-M transcript. In certain embodiments, the target region is within nucleobase 29153 and nucleobase 29281 of SEQ ID NO.: 1. In certain embodiments, the target region is within nucleobase 29158 and nucleobase 29262 of SEQ ID NO.: 1. In certain embodiments, the target region is within nucleobase 29164 and nucleobase 29188 of SEQ ID NO.: 1. In certain embodiments, the target region is within nucleobase 29261 and nucleobase 29279 of SEQ ID NO.: 1. In certain embodiments, the target region is within nucleobase 29168 and nucleobase 29183 of SEQ ID NO.: 1.

In certain embodiments, an antisense oligonucleotide modulates splicing of a pre-mRNA. In certain embodiments, an antisense oligonucleotide modulates splicing a PK-M pre-mRNA. In certain embodiments, an antisense oligonucleotide increases the amount of PK-M mRNA. In certain embodiments, an antisense oligonucleotide increases the inclusion of exon 9 in PK-M mRNA. In certain embodiments, an antisense oligonucleotide decreases the inclusion of exon 10 in PK-M mRNA. In certain embodiments, an antisense oligonucleotide increases the amount of PK-M1 mRNA. In certain embodiments, an antisense oligonucleotide decreases the amount of PK-M2 mRNA.

In certain embodiments it is desirable to alter the splicing of PK-M pre-mRNA to include exon 9 and exclude exon 10. By altering the splicing of PK-M pre-mRNA to include exon 9 and exclude exon 10, expression of PK-M1 will increase and expression of PK-M2 will decrease. In certain embodiments it is desirable to alter the splicing of PK-M pre-mRNA to decrease expression of PK-M2.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one cancer cell. In certain embodiments, such administration results in apoptosis of at least cancer cell. In certain embodiments, a pharmaceutical composition is administered to an animal having at least one symptom associated with cancer. In certain embodiments, such administration results in amelioration of at least one symptom. In certain embodiments, administration of a pharmaceutical composition to an animal results in a decrease of PK-M2 mRNA in a cell of the animal. In certain embodiments, such administration results in an increase in PK-M1 mRNA. In certain embodiments, such administration results in a decrease in PK-M2 protein and an increase PK-M1 protein. In certain embodiments, a PK-M1 protein is preferred over a PK-M2 protein. In certain embodiments, the administration of certain antisense oligonucleotides delays the onset of cancer. In certain embodiments, the administration of certain antisense oligonucleotides slows the proliferation of cancer cells. In certain embodiments, the administration of certain antisense oligonucleotides slows the proliferation of tumor cells. In certain embodiments, the administration of certain antisense oligonucleotides prevents the growth of cancer. In certain embodiments, the administration of certain antisense oligonucleotides prevents the formation of tumors. In certain embodiments, the administration of certain antisense oligonucleotides causes tumor mass to decrease. In certain embodiments, the administration of certain antisense oligonucleotides rescues cellular phenotype.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Screening in HEK-293 Cells to Identify Antisense Oligonucleotides that Promote the Expression of the Pyruvate Kinase M1 Isoform via Alternative Splicing Alternative splicing of the Pyruvate kinase M (PK-M) gene involves a choice between mutually exclusive exons 9 and 10. An antisense oligonucleotide (ASO) screen was carried out to identify potent ASOs that switch the splicing of endogenous PK-M transcripts to include exon 9, thereby promoting PK-M1 isoform expression and down-regulating PK-M2 isoform expression. A diagram of the PK-M genomic region is presented in FIG. 1a.

The ASOs were designed as uniform oligonucleotides, 15 nucleotides in length, with 2'-O-methoxyethyl ribose sugar residues and a phosphorothioate backbone. All the cytosine nucleobases are 5-methylcytosines. The ASOs target exon 10 of the complement of GENBANK Accession No. NT_010194.16 truncated from nucleotides 43281289 to 43314403 (designated herein as SEQ ID NO: 1), and cover the 167-nucleotide region of exon 10 in 5-nucleotide steps, as presented in Table 1.

To examine the effects of antisense oligonucleotide treatment of the cells on endogenous PK-M transcripts, HEK-293 cells were transfected with each ASO at a final concentration of 30 nM. HEK-293 cells were obtained from ATCC and grown at a density of 2×10$^6$ cells in 6-cm dishes in DMEM supplemented with 10% (v/v) FBS, penicillin, and streptomycin, at 37° C. and 5% CO$_2$. Transfections were performed using an ASO:LipofectAMINE2000® ratio of 20 pmoles:1 µL.

Splicing of the PK-M transcripts by radioactive RT-PCR was analyzed 48 hrs after transfection. Two micrograms of total RNA was extracted from the cells using Trizol reagent (Life Technologies, Carlsbad, Calif.). Contaminating DNA was removed with DNase I (Promega). Reverse transcription was carried out using ImPromp-II reverse transcriptase (Promega). Semiquantitative PCR using Amplitaq polymerase (Applied Biosystems) was performed by including [α-$^{32}$P]-dCTP in the reactions. The human-specific primer sets used to amplify endogenous transcripts anneal to PK-M exons 8 and 11, and their sequences are: hPKMF: 5'-AGAAACAGCCAAAGGGGACT-3' (designated herein as SEQ ID NO: 2) and hPKMR: 5'-CATT-CATGGCAAAGTTCACC-3' (designated herein as SEQ ID NO: 3). The primers are represented by arrows at the top portion of FIG. 1a. After 27 amplification cycles for endogenous transcripts, the reactions were divided into two aliquots for digestion with PstI (New England Biolabs) or no digestion. Pst1 digestion was carried out to distinguish between M1 and M2; only M2 has a PstI site, resulting in two cleavage products, B1 (213 nucleotides) and B2 (185 nucleotides) which are the 3' and 5' ends of M2 respectively, as shown at the bottom portion of FIG. 1a.

The products were analyzed on a 5% native polyacrylamide gel, visualized by autoradiography, and quantified on a Typhoon 9410 phosphorimager (GE Healthcare) using Multi Gauge software Version 2.3. The results are presented in FIG. 1b, and Table 1. The % M1 mRNA in endogenous transcripts was calculated using the GC-content-normalized intensities of the top undigested band (M1; depicted as A in the figure), the bottom two digested bands (M2; depicted as B1 and B2 in the figure) in the PstI-digest lanes, and the double-skipped species (D), if detectable. Each product was quantified as a percentage of the total of M1, M2, and double-skipped species. % M1 and % M2 are presented in the Table. The first row of Table 1 denotes the numbers from the untreated control set of cells.

Some of the ASOs strongly increased the proportion of PK-M1 mRNA, with a concurrent increase in the amount of double-skipped mRNA, and a decrease in PK-M2 mRNA. The results indicate that these ASOs target functional enhancer splice elements (ESEs) in exon 10.

The two most potent ASOs were ISIS 461456 and ISIS 461472. ISIS 461472 targets the previously characterized exon 10 SRSF3 motif (Wang, Z. et al., J. Mol. Cell Biol. 4: 79-87, 2012), whereas ISIS 461456 targets a non-overlapping 15-nucleotide region in the middle of exon 10.

TABLE 1

RT-PCR screening of ASOs targeting exon 10 in HEK-293 cells

| Isis No | Target Start Site | Target Stop Site | Sequence | % M1 | % M2 | SEQ ID NO |
|---|---|---|---|---|---|---|
| n/a | n/a | n/a | n/a | 2 | 98 | n/a |
| 461453 | 29153 | 29167 | AATAATTGCAAGTGG | 29 | 69 | 4 |
| 461454 | 29158 | 29172 | CCTCAAATAATTGCA | 26 | 73 | 5 |
| 461455 | 29163 | 29177 | GAGTTCCTCAAATAA | 27 | 70 | 6 |
| 461456 | 29168 | 29182 | CGGCGGAGTTCCTCA | 33 | 64 | 7 |
| 461457 | 29173 | 29187 | CCAGGCGGCGGAGTT | 25 | 69 | 8 |
| 461458 | 29178 | 29192 | GGGCGCCAGGCGGCG | 21 | 72 | 9 |
| 461459 | 29183 | 29197 | GTAATGGGCGCCAGG | 17 | 81 | 10 |
| 461460 | 29188 | 29202 | CGCTGGTAATGGGCG | 23 | 70 | 11 |
| 461469 | 29248 | 29262 | CCCCACTGCAGCACT | 13 | 82 | 12 |
| 461470 | 29253 | 29267 | TATGGCCCCACTGCA | 9 | 90 | 13 |
| 461471 | 29258 | 29272 | ACGATTATGGCCCCA | 6 | 94 | 14 |
| 461472 | 29263 | 29277 | TGAGGACGATTATGG | 23 | 74 | 15 |
| 461473 | 29268 | 29282 | CTTGGTGAGGACGAT | 4 | 95 | 16 |
| 461474 | 29273 | 29287 | CCAGACTTGGTGAGG | 12 | 88 | 17 |

Example 2: ASO Microwalk Centered on the 10W ESE Region

An ASO microwalk was performed to find the most potent ASOs that target the exon 10 regions defined by ISIS 461456 and ISIS 461472.

Overlapping 15-nucleotide ASOs were designed in 1-nucleotide steps. The ASOs were designed as uniform oligonucleotides, 15 nucleotides in length, with 2'-O-methoxyethyl ribose sugar residues and a phosphorothioate backbone. All the cytosine nucleobases are 5-methylcytosines. The ASOs target exon 10 of SEQ ID NO: 1.

To examine the effects of antisense oligonucleotide treatment of the cells on endogenous PK-M transcripts, HEK-293 cells were transfected with each ASO at a final concentration of 60 nM. Cell culture, transfection and RNA analysis was conducted in a similar manner to that described in Example 1. The results of the microwalks are presented in FIG. 1c and Tables 2 and 3. The % M1 mRNA in endogenous transcripts was calculated using the GC-content-normalized intensities of the top undigested band (M1; depicted as A in the figure), the bottom two digested bands (M2; depicted as B1 and B2 in the figure) in the Pst1-digest lanes, and the double-skipped species (D), if detectable. Each product was quantified as a percentage of the total of M1, M2, and double-skipped species. % M1 and % M2 are presented in the Tables below. All standard deviations are ≤4% (n=3).

The results indicate that ISIS 549197 was the most potent in increasing endogenous PK-M1 mRNA and decreasing PK-M2 mRNA levels. The results also indicate that ISIS 555158 optimally abrogated the SRSF3-dependent ESE in exon 10.

TABLE 2

ASO microwalk around ISIS 461456 in HEK-293 cells

| ISIS No | Target Start Site | Target Stop Site | Sequence | % M1 | % M2 | SEQ ID NO |
|---|---|---|---|---|---|---|
| n/a | n/a | n/a | n/a | 2 | 98 | n/a |
| 549191 | 29161 | 29175 | GTTCCTCAAATAATT | 11 | 89 | 18 |
| 549192 | 29162 | 29176 | AGTTCCTCAAATAAT | 17 | 83 | 19 |
| 549193 | 29164 | 29178 | GGAGTTCCTCAAATA | 28 | 69 | 20 |
| 549194 | 29165 | 29179 | CGGAGTTCCTCAAAT | 29 | 69 | 21 |
| 549195 | 29166 | 29180 | GCGGAGTTCCTCAAA | 4 | 95 | 22 |
| 549196 | 29167 | 29181 | GGCGGAGTTCCTCAA | 39 | 57 | 23 |
| 549197 | 29169 | 29183 | GCGGCGGAGTTCCTC | 41 | 39 | 24 |
| 549198 | 29170 | 29184 | GGCGGCGGAGTTCCT | 38 | 51 | 25 |
| 549199 | 29171 | 29185 | AGGCGGCGGAGTTCC | 38 | 53 | 26 |
| 549200 | 29172 | 29186 | CAGGCGGCGGAGTTC | 25 | 69 | 27 |
| 549201 | 29174 | 29188 | GCCAGGCGGCGGAGT | 25 | 67 | 28 |

TABLE 3

ASO microwalk around ISIS 461472 in HEK-293 cells

| ISIS No | Target Start Site | Target Stop Site | Sequence | % M1 | % M2 | SEQ ID NO |
|---|---|---|---|---|---|---|
| 555155 | 29259 | 29273 | GACGATTATGGCCCC | 13 | 88 | 29 |
| 555156 | 29260 | 29274 | GGACGATTATGGCCC | 16 | 84 | 30 |
| 555157 | 29261 | 29275 | AGGACGATTATGGCC | 26 | 61 | 31 |
| 555158 | 29262 | 29276 | GAGGACGATTATGGC | 29 | 60 | 32 |
| 555159 | 29264 | 29278 | GTGAGGACGATTATG | 25 | 70 | 33 |
| 555160 | 29265 | 29279 | GGTGAGGACGATTAT | 26 | 68 | 34 |
| 555161 | 29266 | 29280 | TGGTGAGGACGATTA | 18 | 79 | 35 |
| 555162 | 29267 | 29281 | TTGGTGAGGACGATT | 14 | 83 | 36 |

Example 3: Characterization of the Activation Region of PK-M Exon 10

The target region of ISIS 461456 and ISIS 549197, the most potent ASOs, was characterized in detail.

To map the enhancer elements present in the target region of ISIS 461456, the high sequence identity between exons 9 and 10 was taken advantage of. The PK-M2 minigene was constructed by amplifying a 6.4 kb PK-M exon 8-11 fragment from human genomic DNA (Promega), using Phusion High-Fidelity DNA polymerase and primers PKMinigeneF (5'-GGGGAAGATATCAATTCCCCATTCTGTCTTCC-CATGT-3'; designated SEQ ID NO: 37) and PKMinigeneR (5'-GGGGAACTCGAGCTAGACATT-CATGGCAAAGTTCACC-3'; designated SEQ ID NO: 38). The product was then digested and cloned between the BamHI and XhoI sites of pcDNA3.1+(Invitrogen). For exon-duplication and intron-deletion constructs, the upstream KpnI site 1552 nt downstream of exon 8 was removed by a 1-nt deletion, and an EcoRV restriction site was generated 90 nt upstream of exon 9 by a 2-nt insertion to create a modified wild-type minigene. To generate the 10W, 10B7 and 10F7 constructs, modified exon 9 fragments were generated by annealing the following oligonucleotides: 10W F (5'-CCCTAAACCTTACAGATAGCTCGT-GAGGCTGAGGCAGCCATGTTC-CACCGCAAGCTGTTTGAGG AACTCCGCCGAGCCT-CAAGTCACTCCACAGACCTCATGGAAGCCAT-3'; designated SEQ ID NO: 39), 10F7F (5'-CCCTAAACCT-TACAGATAGCTCGTGAGGCTGAGGCAGCCATGTTC-CACCGCAAGCTGTTTGAGG AACTTGTGCGAGCCT-CAAGTCACTCCACAGACCTCATGGAAGCCAT-3'; designated SEQ ID NO: 40), 10B7F (5'-CCCTAAACCT-TACAGATAGCTCGTGAGGCTGAGGCAGCCATGTTC-CACCGCAAGCTGTTTGAAG AACTCCGCCGAGCCT-CAAGTCACTCCACAGACCTCATGGAAGCCAT-3'; designated SEQ ID NO: 41) with Exon 9Rev oligo (5'-CCCTTAGGGCCCTACCTGCCAGACTCCGTCAGAAC-TATCAAAGCTGCTGCTAAACACTTATAAG AAGCCTCCACGCTGCCCATGGCCATGGCTTCCAT-GAGGTCTG-3'; designated SEQ ID NO: 42) and amplifying using Ex10ADupF (5'-TTCCCCATTCTGTCTTCC-CATGTGTTGTGTCTCGTTTTTTTCCTCCTCCTTCCC TCTTCCTTGCCCC CTCTTCCCCTAAACCTTACAG-3'; designated SEQ ID NO: 43) and Ex10ADupR (5'-AGTGT-TACCTGCCCTTAGGGCCCTAC-3'; designated SEQ ID NO: 44). The 106-nt oligonucleotide carries mutations that duplicate specific stretches of exon 10 over the corresponding region of exon 9. Another fragment was amplified from the wild-type minigene using the following primer pairs: Ex10BF: 5'-GTAGGGCCCTAAGGGCAGGTAACAC-3' (designated SEQ ID NO: 45) and RKpnI: 5'-GGG-GAAGGTACCACTGAGCAGGGCATT-3' (designated SEQ ID NO: 46). Both fragments were then gel-purified, subjected to a second overlap-extension (OE) PCR using the end primers FEcoRV (5'-GGGGAAGATATCAATTCCC-CATTCTGTCTTCCCATGT-3'; designated SEQ ID NO: 47) and RKpnI (5'-GGGGAGGTACCACTGAGCAGGG-CATT-3'; designated SEQ ID NO: 48).

Figure 1B:
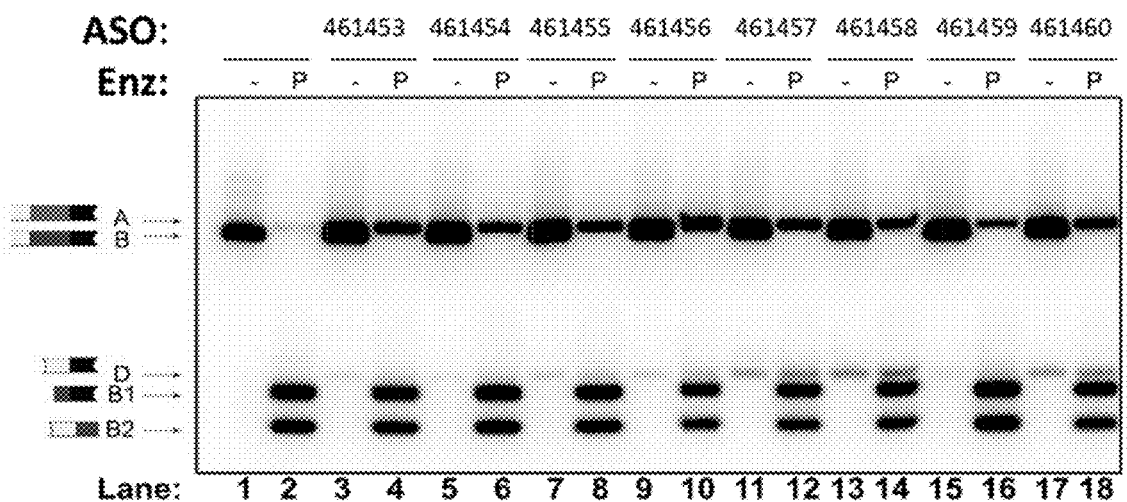
FIG. 1b: Initial ASO walks. ASOs were transfected at 30 nM in HEK-293 cells. Radioactive RT-PCR and restriction digest of endogenous PK-M transcripts are shown. The transfected ASO is indicated at the top. cDNA amplicons and fragments are indicated on the left. Lane numbers are indicated at the bottom.
Figure 1B:
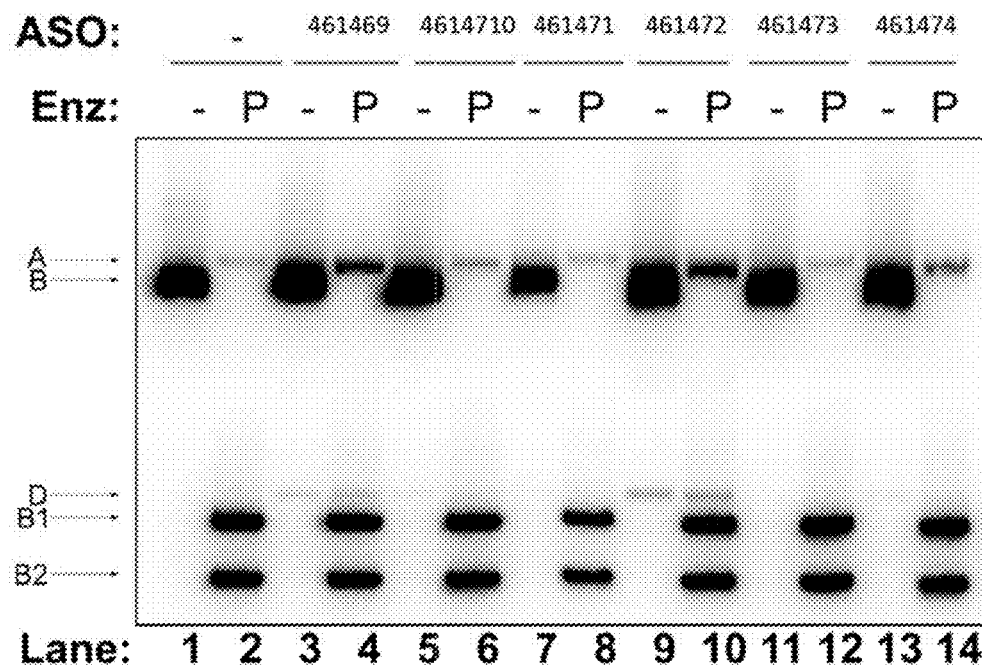
Figure 1C:
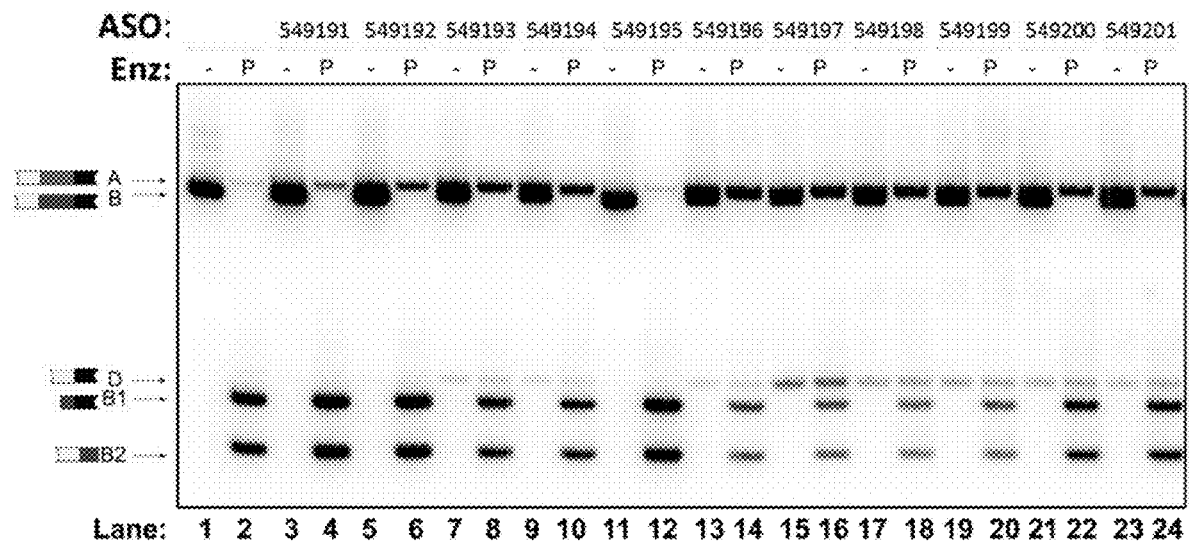
FIG. 1c: ASO microwalks. ASOs were transfected at 60 nM in HEK-293 cells. Radioactive RT-PCR and restriction digest of endogenous PK-M transcripts are shown. The transfected ASO is indicated at the top. cDNA amplicons and fragments are indicated on the left. Lane numbers are indicated at the bottom.
Figure 1C:
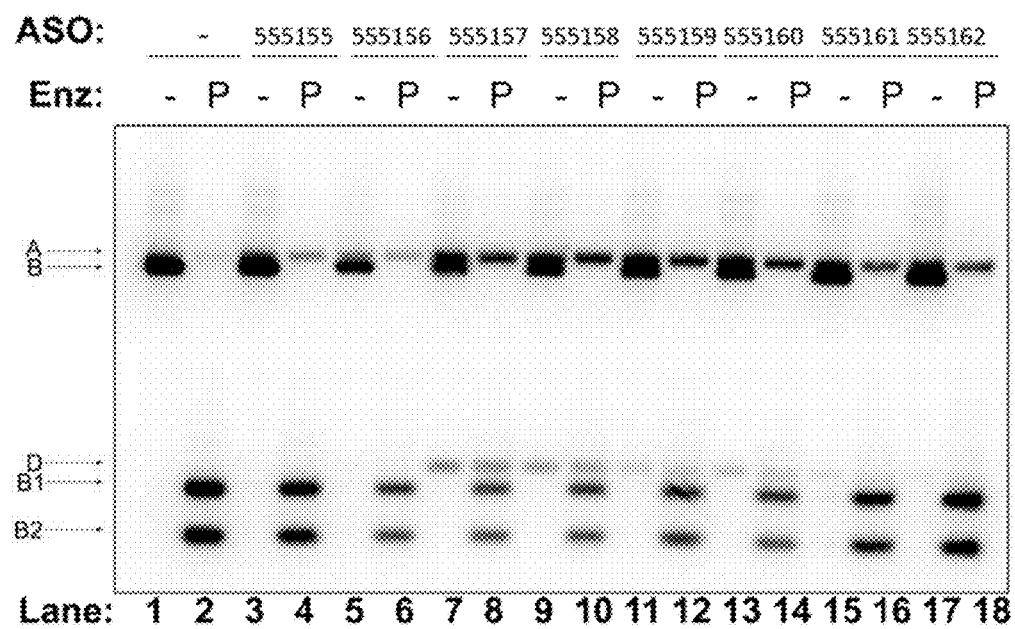

As shown in FIG. 2a, the minigene comprises the same genomic region as indicated in FIG. 1a. The 10W minigene duplicates the entire exon 10 10W region into exon 9; the 10F minigene duplicates the first eight nucleotides of ISIS 549197; and the 10B minigene duplicates the last seven nucleotides of ISIS 549197. Due to the low baseline PK-M1 inclusion from the wild-type minigene, any strong ESEs comprised by the candidate regions was expected to lead to an increase in PK-M1 mRNAs expressed from the minigene.

The results are presented in FIG. 2b and Table 4. Standard deviations are 0.2%, 0.3%, and 2.6% for 10G, 10F, and 10B, respectively (n=3). The data indicate that duplication of the B7 region (10B), but not the F7 (10F) and 10W region, lead to increased exon 9 inclusion. This result suggests that the 8-nucleotide B7 motif is a bona fide exon 10 ESE.

TABLE 4

Analysis of minigenes 10W, 10F and 10B

| Minigene | % M1 |
|---|---|
| 10W | 2 |
| 10F | <1 |
| 10B | 29 |

Example 4: Characterization of the Mechanism of Action of the ASOs

To characterize the mechanism of action of ISIS 461456 and ISIS 549197 on the inclusion of exon 9 and skipping of exon 10, these ASOs were co-transfected with the PK-M wild-type or duplicated exon 10 minigenes. The wild-type minigene comprises the flanking exons 8 and 11, and the complete genomic region between both exons, whereas the duplication construct has exon 10 replaced completely with exon 9.

Figure 2C:
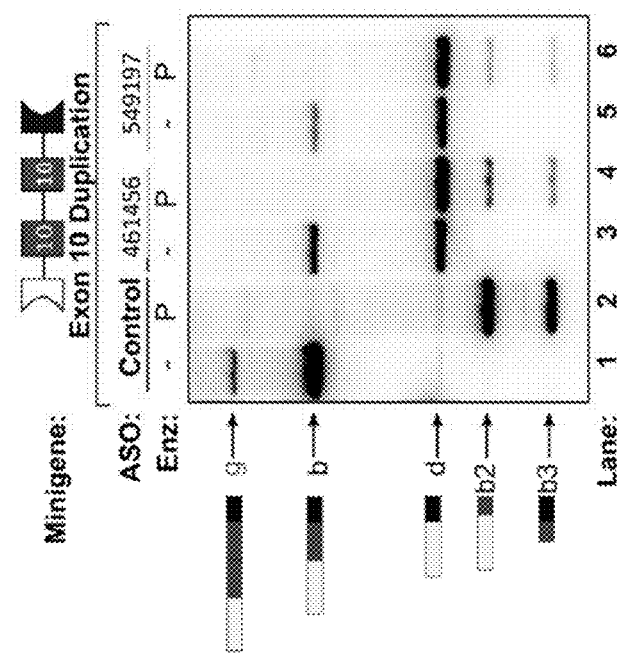
FIG. 2c: Wild-type minigene transcript level changes as a result of ASO co-transfection in HEK-293 cells. Labeled bands are indicated in lower case on the left.

HEK-293 cells were cultured, as described above. Five μg of minigene plasmid per 10-cm dish or one μg per 6-cm dish was transiently transfected using LipofectAMINE2000® (Life Technologies, Carlsbad, Calif.). ASOs were transfected, as described above, at a final concentration of 60 nM. A control ASO (5'-TCATTTGCTTCATACAGG-3', designated as SEQ ID NO: 49) was also used. The results are presented in FIGS. 2c and d, as well as in Table 5. Standard deviations for FIG. 2c are 0.6%, 4.2% and 2.9% for control, ISIS 461456 and ISIS 549197, respectively (n=3). Standard deviations for FIG. 2d are 0.8%, 0.9%, and 2.6% for control, ISIS 461456 and ISIS 549197, respectively (n=3).

As expected, both ISIS 461456 and ISIS 549197 switched the splicing of the minigene transcript by simultaneously increasing the amount of the M1 mRNA and decreasing the amount of the M2 mRNA expressed from the wild-type minigene (FIG. 2c and Table 5). However, ISIS 461456 increased exon 9 inclusion to a greater extent than ISIS 549197, although the latter decreased exon 10 inclusion to a greater extent, resulting in higher levels of double-skipped (Skp) transcripts.

Figure 2D:
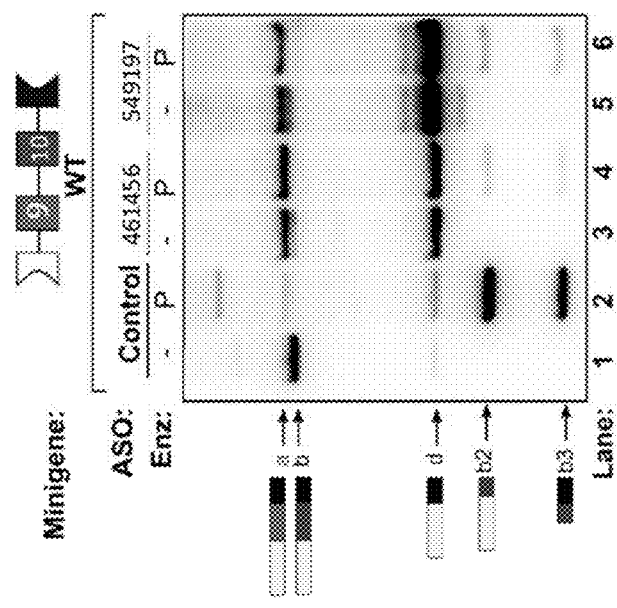
FIG. 2d: Exon 10 duplication minigene transcript level changes as a result of ASO co-transfection in HEK-293 cells. Labeled bands are indicated in lower case on the left.

Co-transfection of ISIS 461456 or ISIS 549197 with the exon 10 duplication minigene interfered with the inclusion of exon 10, leading to a large increase in double skipped species (FIG. 2d and Table 5). ISIS 461456 was especially potent, nearly converting all the mRNA to the Skp isoform.

These results suggest that both ISIS 461456 and ISIS 549197 interfere with the activation of exon 10.

TABLE 5

Minigene transcript level as a result of ASO co-transfection in HEK-293 cells

| Minigene | ASO treatment | % M1 | % Skp | % M2 |
|---|---|---|---|---|
| Wild-type | Control | 1 | 6 | 93 |
| | ISIS 461456 | 26 | 63 | 11 |
| | ISIS 5491597 | 8 | 85 | 7 |
| Exon 10 duplication | Control | n/a | 1 | 99 |
| | ISIS 461456 | n/a | 60 | 40 |
| | ISIS 5491597 | n/a | 82 | 18 |

Figure 2E:
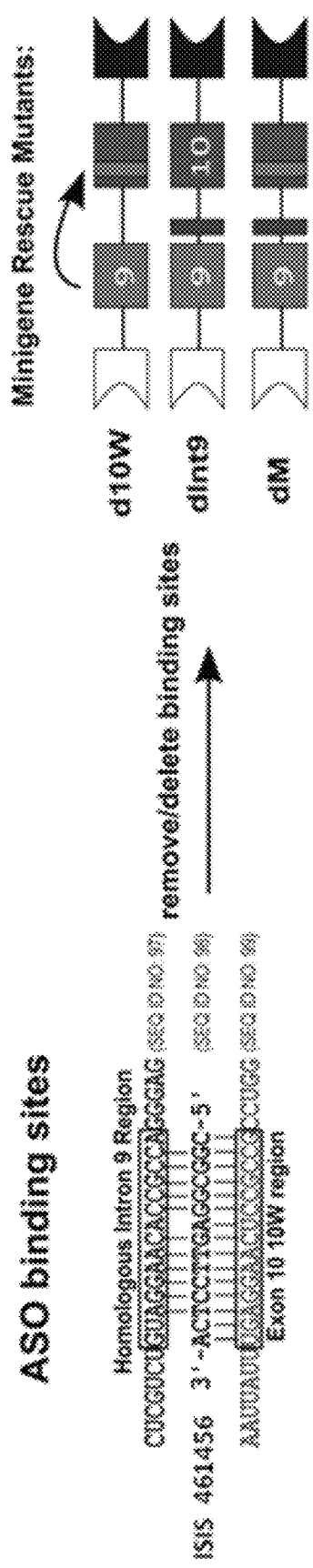
FIG. 2e: Alignment of the sequences of ISIS 461456, the complementary region in exon 10, and a homologous region in intron 9 is shown. Vertical lines show sequence identity. A diagram of the minigene mutants is shown on the right.

Alignment of the 10W region with the PK-M exons 8-11 genomic region revealed a highly homologous region in intron 9 (FIG. 2e). To weigh the relative contributions of the exon 10 and intron 9 complementary regions for the effect of ISIS 461456 and ISIS 549197 on PK-M splicing, minigene mutation were made that eliminated the presumptive target sites in exon 10, intron 9, or both. The effect of the ASOs on splicing of the mutant minigene transcripts was then determined.

Three mutants were generated (FIG. 2e). The exon 10 10W region was mutated by duplicating the corresponding exon 9 region and termed the d10W construct. To generate the d10W minigene construct, a modified exon 10 fragment was constructed by annealing d10W F (5'-ATGTTGCTCCCCTAGATTGCCCGT-GAGGCAGAGGCTGCCATCTACCACTTGCAATTAT-TTGAAGA
ACTTGTGCGCCTGGCGCCCATTACCAGCGACCC-CACAGAAGCCAC-3'; designated SEQ ID NO: 50) with Exon 10 Rev (5'-CGCTGCCGCCTCCTACCTGCCA-GACTTGGTGAGGACGATTATGGCCC-CACTGCAGCACTTGAAG GAGGCCTCCACGGCACC-CACGGCGGTGGCTTCTGTGGGGTCGCT-3'; designated SEQ ID NO: 51) and amplifying using Ex9ADupF (5'-TGGACGGATGTTGCTCCCCTAG-3'; designated SEQ ID NO: 52) and Ex9ADupR (5'-GGTAC-CACTGAGCAGGGCATTCCAGG-GAGCCGCTGCCGCCTCCTAC-3'; designated SEQ ID NO: 53). The 108-nt oligonucleotide carries mutations that duplicate specific stretches of exon 9 over the corresponding region in exon 10. Another fragment was amplified from the wild-type minigene using the following primer pairs: FEcoRV and Ex9BR (5'-GTAGGGCCCTAAGGGCAGGTAACAC-3'; designated SEQ ID NO: 54). Both fragments were then gel-purified and subjected to a second OE PCR reaction using the FEcoRV and RKpnI primers.

A 15-nucleotide deletion was introduced in intron 9 that removed the homologous target region and this was termed the dInt9 construct. To generate the dInt9 mutant, two fragments were generated from the wild-type minigene construct, using the following primer pairs: FEcoRV and PKMdelB12R (5' TGCCCTGCCATGACCTCCCA-GACGAGAAGAGGCTCTGTGCCCAG-3'; designated SEQ ID NO: 55) and PKMdelB125 (5'-ACAGAGCCTCTTCTCGTCTGGGAGGT-CATGGCAGGGCAG-3'; designated SEQ ID NO: 56).

To generate the dM double mutant, the same two fragments were generated from the d10W minigene. Both fragments were then gel-purified and subjected to a second OE PCR using FEcoRV and RKpnI. All generated fragments were then cloned between the EcoRV and KpnI sites of the modified wild-type minigene plasmid.

There was a slight decrease in baseline minigene PK-M2 mRNA expressed from the d10W minigenes (FIG. 2f and Table 6), suggesting that the duplicated exon 9 region contains weak repressor elements. This was not the case for the dInt9 construct, suggesting that this region alone does not have a major effect in dictating M1/M2 ratios.

Figure 2F:
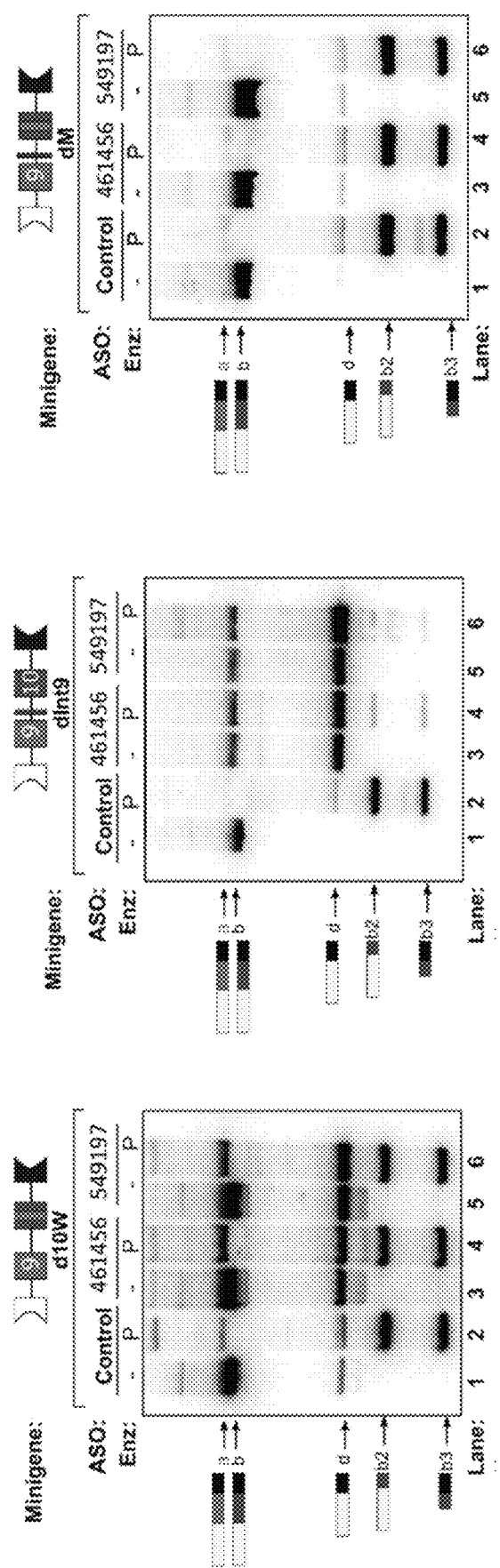
FIG. 2f: Minigene transcript level changes as a result of ASO co-transfection in HEK-293 cells. Labeled bands are indicated on the left: uncut M1 fragment (a, 481 nucleotide); uncut M2 fragment (b, 481 nucleotides); PstI-cleaved M2 5' fragment (b2, 268 nucleotides); PstI-cleaved M2 3' fragment (b3, 213 nucleotides); a spliced mRNA that skips both exons 9 and 10 (d, 314 nucleotides).

The loss of the 10W binding site largely abrogated the exon 9 inclusion and exon 10 skipping promoted by ISIS 461456 and ISIS 549197 (FIG. 2f and Table 6). In contrast, removal of the intron 9 homologous region did not block the effect of ISIS 461456 and ISIS 549197 on splicing. However, when both binding sites were removed, the effect of ISIS 461456 and ISIS 549197 was completely abrogated. The results indicate that ISIS 461456 and ISIS 549197 largely mediate exon 9 inclusion through the 10W complementary region in exon 10.

TABLE 6

Mutant minigene transcript level as a result of ASO co-transfection in HEK-293 cells

| Minigene | ASO treatment | % M1 | % Skp | % M2 |
|---|---|---|---|---|
| D10W | Control | 5 | 9 | 86 |
|  | ISIS 461456 | 11 | 20 | 68 |
|  | ISIS 5491597 | 10 | 34 | 56 |
| dInt9 | Control | 1 | 7 | 92 |
|  | ISIS 461456 | 19 | 74 | 7 |
|  | ISIS 5491597 | 12 | 80 | 9 |
| dM | Control | 2 | 5 | 93 |
|  | ISIS 461456 | 1 | 6 | 93 |
|  | ISIS 5491597 | 1 | 5 | 94 |

Example 5: Antisense Inhibition of PK-M in Glioblastoma Cells

A characteristic splicing switch from PK-M1 to PK-M2 occurs during gliomagenesis (Clower, C. V. et al., Proc. Natl. Acad. Sci. USA 107: 1894-1899, 2010; Bluemlein, K. et al., Oncotarget. 2: 393-400, 2011). Glioblastoma cells also have a higher basal level of PK-M1 mRNA, which is expected to facilitate the ASO-mediated PK-M splicing switch (Clower, C. V. et al., Proc. Natl. Acad. Sci. USA 107: 1894-1899, 2010).

To compare the effect of ASOs targeting the 10W region versus those targeting the SRSF3 region, side-by-side ASO transfections at final concentrations of 30 nM, 60 nM, and 90 nM in the glioblastoma cell lines A172 and U87-MG were conducted. ISIS 555158 was the ASO targeting the SRSF3 region that was chosen and was transfected at final concentrations of 60 or 90 nM. The control oligonucleotide was transfected at a final concentration of 90 nM. The experiment was run in triplicates.

Figure 3A:
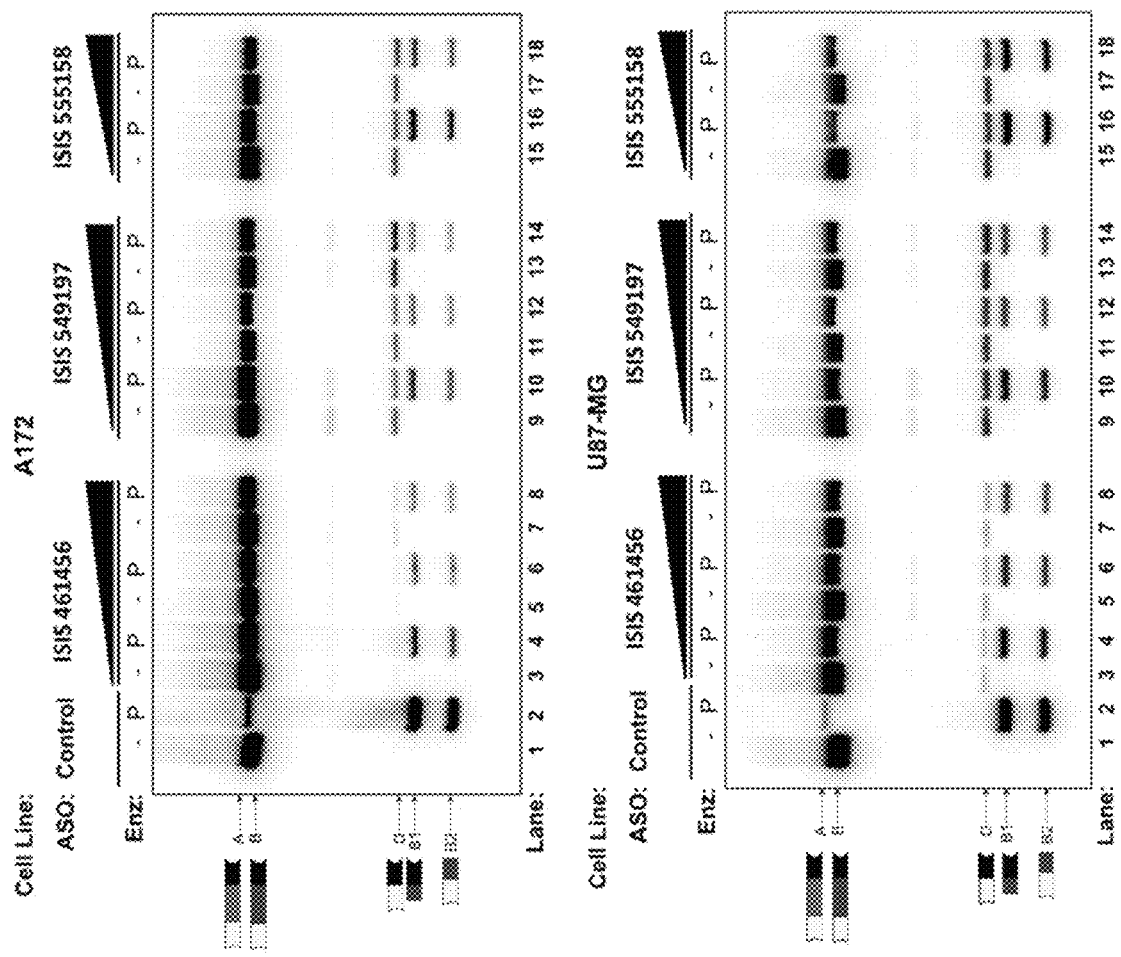
FIG. 3a: Effect of ISIS 549197, ISIS 461456, and ISIS 555158 on endogenous PK-M mRNAs in A172 and U87-MG glioblastoma cells.

U87-MG and A172 cells were obtained from ATCC and grown in DMEM supplemented with 10% (v/v) FBS, penicillin, and streptomycin, at 37° C. and 5% $CO_2$. ASO transfections were conducted as described above. Radioactive RT-PCR and restriction digest of endogenous PK-M transcripts were performed 36 hrs after transfection. The results are presented in FIG. 3a, as well as in Tables 7 and 8. All standard deviations are ≤4% (n=3)

As expected, there was a dose-dependent increase in exon 9 inclusion and exon 10 skipping in these cell lines, with ISIS 461456 and ISIS 549197 performing better than ISIS 555158. Consistent with the minigene experiments, treatment with ISIS 461456 resulted in greater increase in PK-M1 mRNA levels than treatment with other ASOs, whereas treatment with ISIS 549197 resulted in more double-skipped mRNA and a larger decrease in PK-M2 mRNA levels than treatment with other ASOs.

TABLE 7

Effect of ASO treatment on PK-M mRNA levels in A172 glioblastoma cells

| Treatment | Dose (nM) | % M1 | % Skp | % M2 |
|---|---|---|---|---|
| Control | 90 | 15 | — | 85 |
| ISIS 461456 | 30 | 52 | — | 48 |
|  | 60 | 63 | — | 37 |
|  | 90 | 73 | — | 27 |
| ISIS 549197 | 30 | 49 | 8 | 42 |
|  | 60 | 49 | 12 | 38 |
|  | 90 | 56 | 23 | 21 |

TABLE 7-continued

Effect of ASO treatment on PK-M mRNA levels in A172 glioblastoma cells

| Treatment | Dose (nM) | % M1 | % Skp | % M2 |
|---|---|---|---|---|
| ISIS 555158 | 60 | 39 | 10 | 51 |
|  | 90 | 44 | 15 | 41 |

TABLE 8

Effect of ASO treatment on PK-M mRNA levels in U87-MG glioblastoma cells

| Treatment | Dose (nM) | % M1 | % Skp | % M2 |
|---|---|---|---|---|
| Control | 90 | 4 | — | 96 |
| ISIS 461456 | 30 | 43 | 2 | 55 |
|  | 60 | 50 | 3 | 46 |
|  | 90 | 54 | 5 | 41 |
| ISIS 549197 | 30 | 36 | 12 | 52 |
|  | 60 | 38 | 17 | 44 |
|  | 90 | 45 | 22 | 33 |
| ISIS 555158 | 60 | 24 | 11 | 65 |
|  | 90 | 29 | 14 | 57 |

Figure 3B:
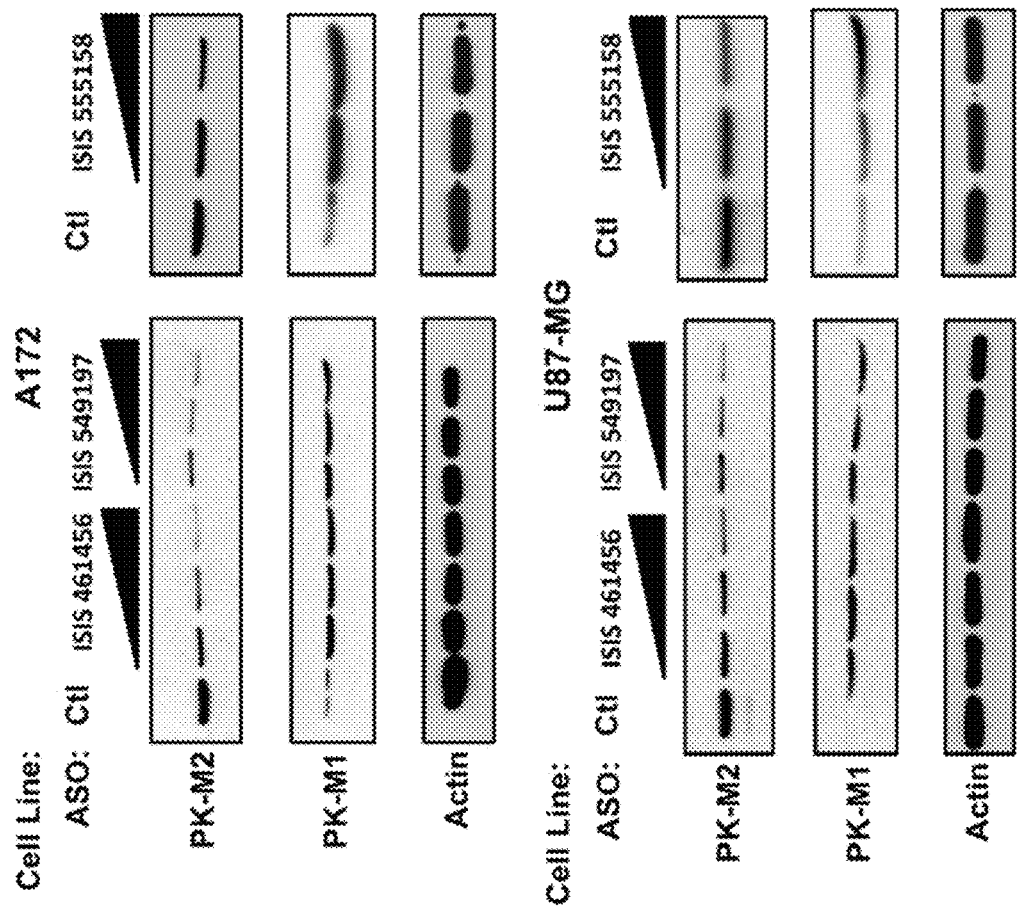
FIG. 3b: Immunoblot analysis of PK-M protein isoform levels in A172 and U87-MG glioblastoma cells transfected with ISIS 549197, ISIS 461456, or ISIS 555158. Antibodies used are indicated on the left.

To estimate the amount of PK-M1 and PK-M2 proteins in the cell lysates, isoform-specific antibodies were used. Cells were lysed in SDS, and total protein concentration was measured by the Bradford assay. Total protein of 5-30 µg was separated by SDS-PAGE and transferred onto nitrocellulose. This was followed by blocking with 5% (w/v) milk in Tris-buffered saline with Tween-20, probing with antibodies and visualization by enhanced chemiluminescence (Roche). The primary antibodies used were β-actin (Genscript mAb, 1:10,000); PK-M2 (Cell Signaling Technology, rAb, 1:2,000); and PK-M1 (ProteinTech, rAb, 1:1,000). Secondary antibodies were goat anti-mouse or anti-rabbit HRP conjugates (Bio-Rad, 1:20,000). The results are presented in FIG. 3b. A representative blot from one of three independent experiments is shown.

As expected, PK-M1 and PK-M2 protein isoform levels closely mirrored their mRNA levels. There was detectable PK-M1 protein after transfection of each of the three ASOs, but ISIS 549197 resulted in the greatest decrease in PK-M2 levels.

Figure 3C:
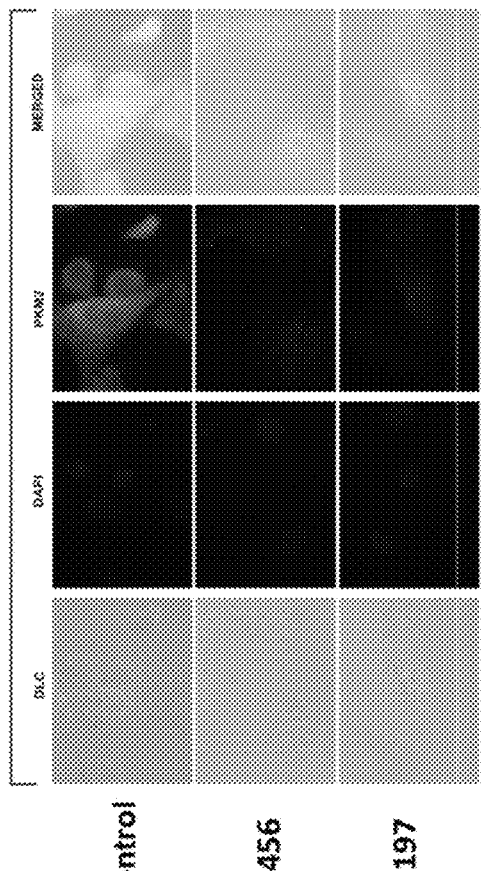
FIG. 3c: Immunofluroescence staining of glioblastoma cells with antibodies directed against PK-M2. Cell lines were stained with PK-M2 antibody and the DNA-binding fluorescent stain, DAPI.
Figure 3C:
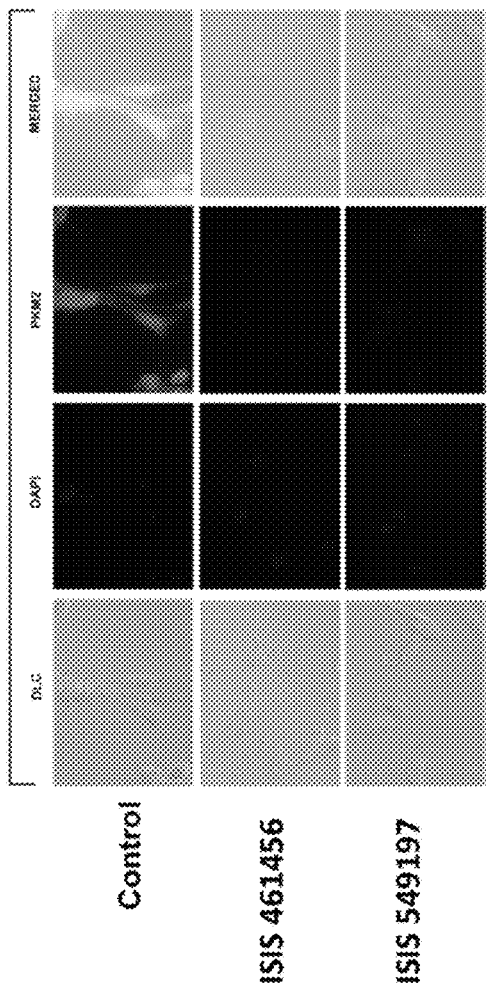

The data was also confirmed by immunofluorescence technique. Cells were first transfected with ASOs as described above and then plated on 4-well culture slides (BD Biosciences) 24-hrs post transfection. At 36 hrs post-transfection, the cells were washed with PBS and fixed with 3.7% formaldehyde in PBS for 20 min. Cells were then permeabilized in 0.1% Triton X-100 in PBS for 10 min after washing in PBS, and then blocked for 20 min in blocking buffer (1% goat serum in PBS). The cells were then incubated overnight with rabbit monoclonal anti-PK-M2 antibody (Cell Signaling Technology). After washing 3 times with PBS, the cells were then incubated for 1 hr in blocking buffer containing Alexa Fluor 594-conjugated goat anti-rabbit secondary antibody (Molecular Probes/Invitrogen). Cells were analyzed using a Zeiss Axiopian.Z1 upright fluorescent microscope. Downregulation of PK-M2 protein was also observed when either ISIS 461456 or ISIS 549197, but not the control ASO, was transfected into A172 or U87-MG cells (FIG. 3c).

Example 6: Effect of Antisense Inhibition of PK-M on Apoptosis in Glioblastoma Cells The effect of treatment with ASOs targeting PK-M on apoptosis of the glioblastoma cells was studied.

Figure 4:
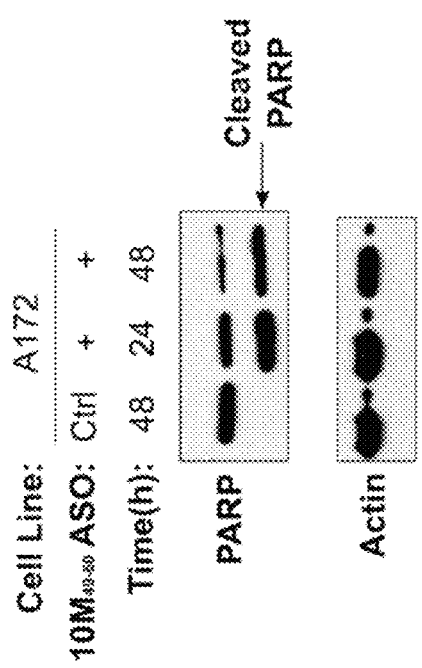
FIG. 4: Immunoblot analysis of A172 cells transfected with ISIS 549197 or control ASO. Antibodies used are indicated on the left.

Treatment with ISIS 549197 resulted in cleaved PARP as early as 24 hrs post-transfection in A172 cells, indicating that the cells were undergoing apoptosis. Cells were harvested 24 or 48 hrs after transfection, whereas the control cells were harvested after 48 hrs. The cells were lysed in SDS and total protein concentration was measured by the Bradford assay. Total protein (5-30 µg) was separated by SDS-PAGE and transferred onto nitrocellulose. The membrane was blocked with 5% (w/v) milk in Tris-buffered saline with Tween-20 and probed with PARP primary antibody (Cell Signaling Technology, rAb, 1:1,000). The bands were visualized by enhanced chemiluminescence (Roche). The results are presented in FIG. 4.

Figure 5A:
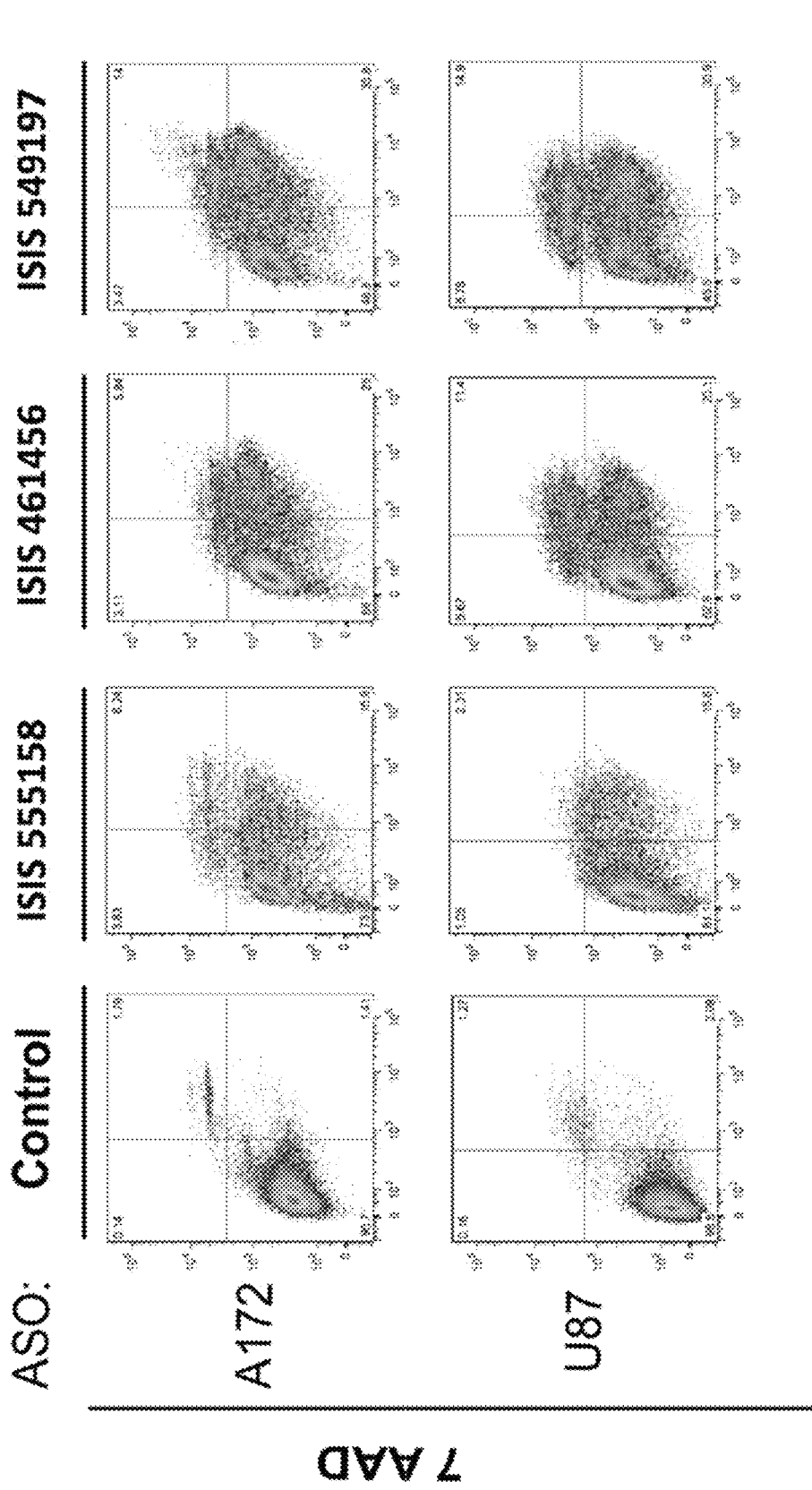
FIG. 5a: Flow cytometric analysis of A172 or U87-MG glioblastoma cells transfected with the indicated ASOs and stained with Annexin V-APC/7-AAD.

To confirm this observation, Annexin V staining assays were performed with A172 and U87-MG cells transfected with ISIS 460456, ISIS 549197, or ISIS 555158 at a final concentration of 90 nM. Cells ($1\times10^6$ in number) were collected 36 hrs after transfection, washed twice with PBS and resuspended in 1× Binding Buffer (10 mM HEPES, pH 7.4; 140 mM NaCl; 2.5 mM $CaCl_2$). The cells were then stained with 5 µl each of Annexin V-APC antibody and 7-AAD (Becton Dickinson) in the dark for 15 min, and analyzed for apoptosis for flow cytometry using an LSRII Cell Analyzer (Becton Dickinson). Both early apoptotic ($7AAD^-$/Annexin $V^+$) and late apoptotic ($7AAD^+$/Annexin $V^+$) cells were included in the quantification. The results are presented in FIG. 5a and Table 9, and are a representative of 3 biological triplicates each. Table 9 presents the percentage of Annexin V-positive cells, as indicated in the two right quadrants in each plot of the flow cytometric analysis.

TABLE 9

| Effect of ASO treatment on apoptosis in A172 glioblastoma cells | | | | |
|---|---|---|---|---|
| ASO: | Control | ISIS 555158 | ISIS 461456 | ISIS 549197 |
| A172 | 3 | 23 | 34 | 48 |
| U87-MG | 4 | 18 | 32 | 44 |

Figure 5B:
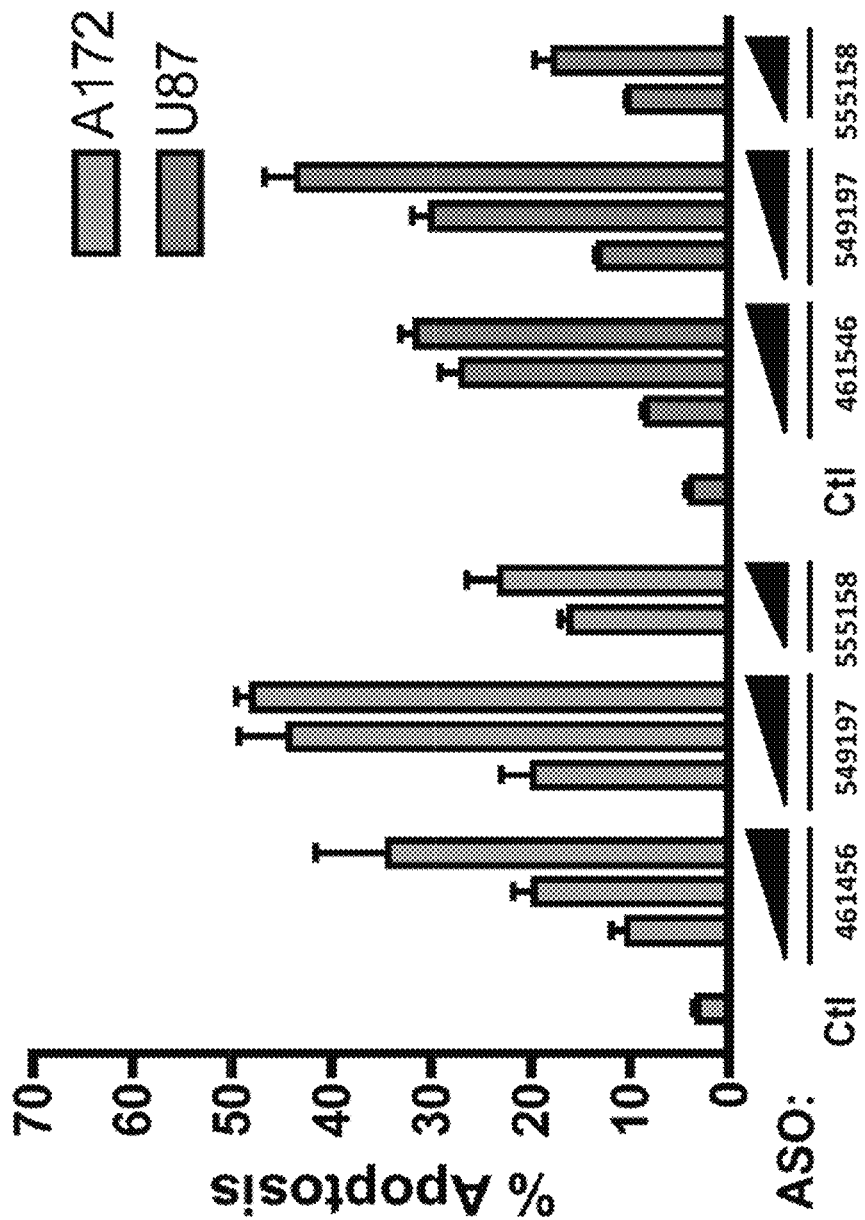
FIG. 5b: Dose-dependent apoptosis in glioblastoma cells by ASO treatment. Error bars represent s.d. (n=3).

To confirm this finding, cells were transfected with ISIS 461456 or ISIS 549197 at 30 nM, 60 nM, or 90 nM or with ISIS 555158 at 60 nM or 90 nM. The control ASO was transfected at 90 nM. The data is presented in FIG. 5b and Tables 10 and 11. The proportion of Annexin V-positive cells increased in an ASO dose-dependent manner, indicating that ASO-mediated switching of PK-M splicing induces apoptosis in these cell lines. ISIS 549197 was the most potent in inducing apoptosis among the three ASOs tested.

TABLE 10

| Effect of ASO multi-dose treatment on apoptosis in A172 glioblastoma cells | | |
|---|---|---|
| Treatment | Dose (nM) | % apoptosis |
| Control | 90 | 3 |
| ISIS 461456 | 30 | 10 |
|  | 60 | 20 |
|  | 90 | 34 |
| ISIS 549197 | 30 | 20 |
|  | 60 | 44 |
|  | 90 | 48 |
| ISIS 555158 | 60 | 16 |
|  | 90 | 23 |

TABLE 11

| Effect of ASO multi-dose treatment on apoptosis in U87-MG glioblastoma cells | | |
|---|---|---|
| Treatment | Dose (nM) | % apoptosis |
| Control | 90 | 4 |
| ISIS 461456 | 30 | 8 |
|  | 60 | 27 |
|  | 90 | 32 |
| ISIS 549197 | 30 | 13 |
|  | 60 | 30 |
|  | 90 | 44 |
| ISIS 555158 | 60 | 10 |
|  | 90 | 18 |

Example 7: Effect of Antisense Inhibition of PK-M on Apoptosis in PK-M1 Inducible Cells To investigate the mechanism of action by which treatment with ASOs elicits apoptosis in glioblastoma cells, stable cell lines that express human PK-M1 cDNA in a doxycycline-inducible manner or PK-M2 cDNA in a constitutive manner were generated.

To generate cell lines that over-express human PK-M1 isoform in a doxycycline-dependent manner, A172 cells were first infected with MSCV-rtTA-hygro virus, and selected in hygromycin for 2 weeks. Human PK-M1 cDNA was amplified from A172 cells transfected with ISIS 549197 using the following primer pair: hPKT7cDNAF (5'-GGG-GAACTCGAGATGGCTTCTAGGATGGCATC-GATGACAGGTGGCCAACAGATGGGCATGTCG AAGCCCCATAGTGAAGCCG-3'; designated SEQ ID NO: 57) and hPKT7cDNAR (5'-GGGGAAGAATTCT-CACGGCACAGGAACAACACGCATG-3'; designated SEQ ID NO: 58) with Phusion High-Fidelity DNA Polymerase (Finnzymes). The resulting amplicon containing the T7 tag was gel-purified and cloned between the EcoRI and XhoI sites of the retroviral TtiGP plasmid. A172-rTA cells were then infected with TtiGP-PKM1 virus. To make cells lines constitutively over-express human PK-M2, PK-M2 cDNA from A172 cells were amplified using the same primers and cloned between the EcoRI and XhoI sites of the retroviral PIG plasmid. A172 and U87-MG cells were then infected with the PIG-PKM2 virus. All infected cells were then selected with 100 µg/ml puromycin for 3 days. All plasmids were sequenced to confirm their identities.

Figure 6A:
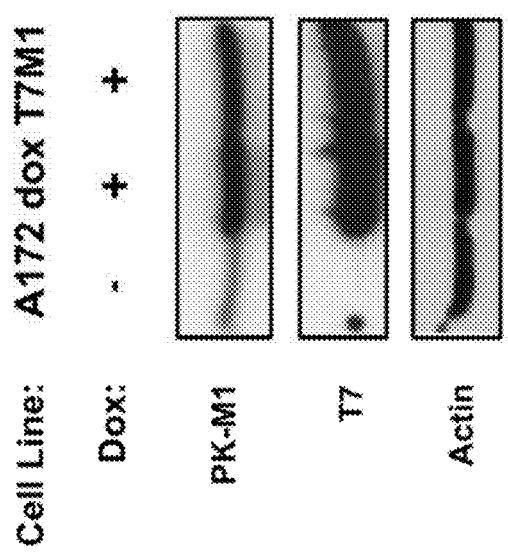
FIG. 6a: Immunoblot analysis of A172 cells stably transduced with rtTA and doxycycline-inducible human T7-tagged PK-M1 cDNA. Antibodies used are indicated on the left.
Figure 6B:
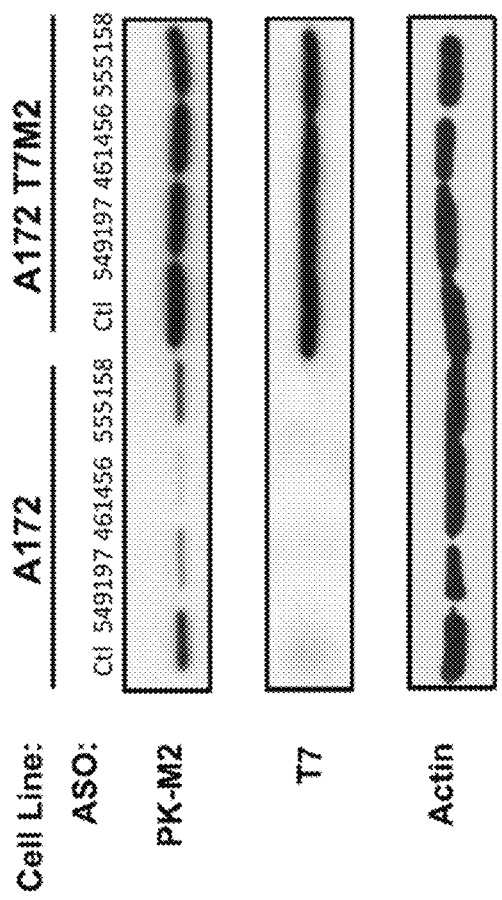
FIG. 6b: Immunoblot analysis of A172 and U87-MG cells stably transduced with T7-tagged PK-M1 cDNA. Transduced cells and parental cell lines were transfected with ASOs. Antibodies used are indicated on the left.
Figure 6B:
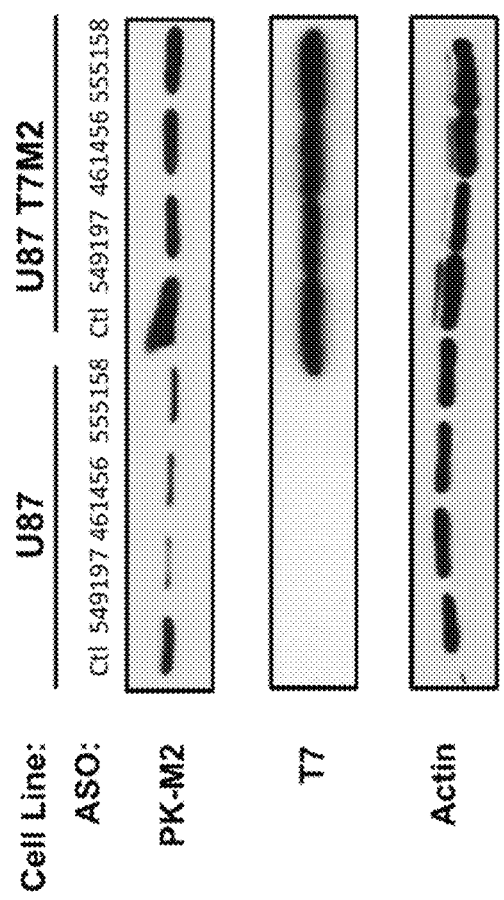

FIG. 6a presents the immunoblot analysis of A172 cells stably transduced with rtTA and doxycycline-inducible human T7-tagged PK-M1 cDNA. FIG. 6b presents the immunoblot analysis of A172 and U87 cells stably transduced with T7-tagged human PK-M2 cDNA. Cells were grown in parallel with or without doxycycline, and harvested after 72 hrs. The cells were lysed and prepared for western blotting analysis, as described in an earlier Example. The primary antibodies used were PK-M1 (ProteinTech, rAb, 1:1,000), T7 (mAb, 1:1,000), PK-M2 (Cell Signaling Technology, rAb, 1:2,000) and β-actin (Genscript mAb, 1:10,000).

Figure 6C:
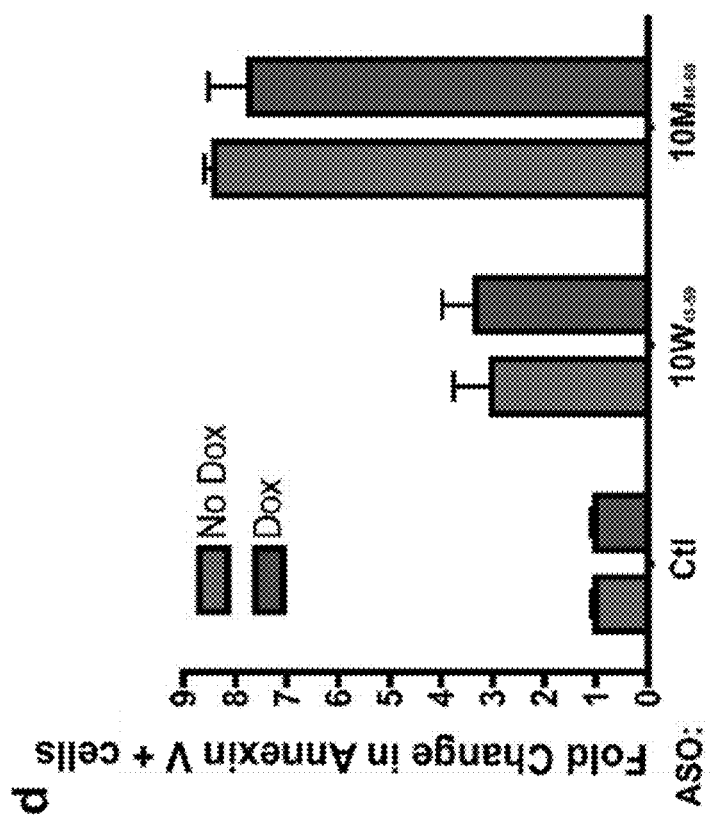
FIG. 6c: Histogram analysis of cells grown as in FIG. 6a and transfected with the indicated ASOs. Doxycycline conditions are shown on the left. Error bars represent s.d. (n=3).

To investigate the role of PK-M1 in ASO-mediated apoptosis, doxycycline was added to the PK-M1-inducible cells for three days, after which the cells were treated with ISIS 461456, ISIS 549197, or control ASO at 60 nM final concentrations. After 36 hrs, the cells were stained for Annexin V and analyzed by flow cytometry. The results are presented in FIG. 6c and Table 10. The histograms of FIG. 6c indicate the fold increase in Annexin V-positive cells, compared to the control ASO for each condition. The data indicate that there was a similar increase in the number of Annexin V-positive cells in the cells that did or did not overexpress PK-M1, suggesting that PK-M1 induction did not cause apoptosis in these cells.

Figure 6D:
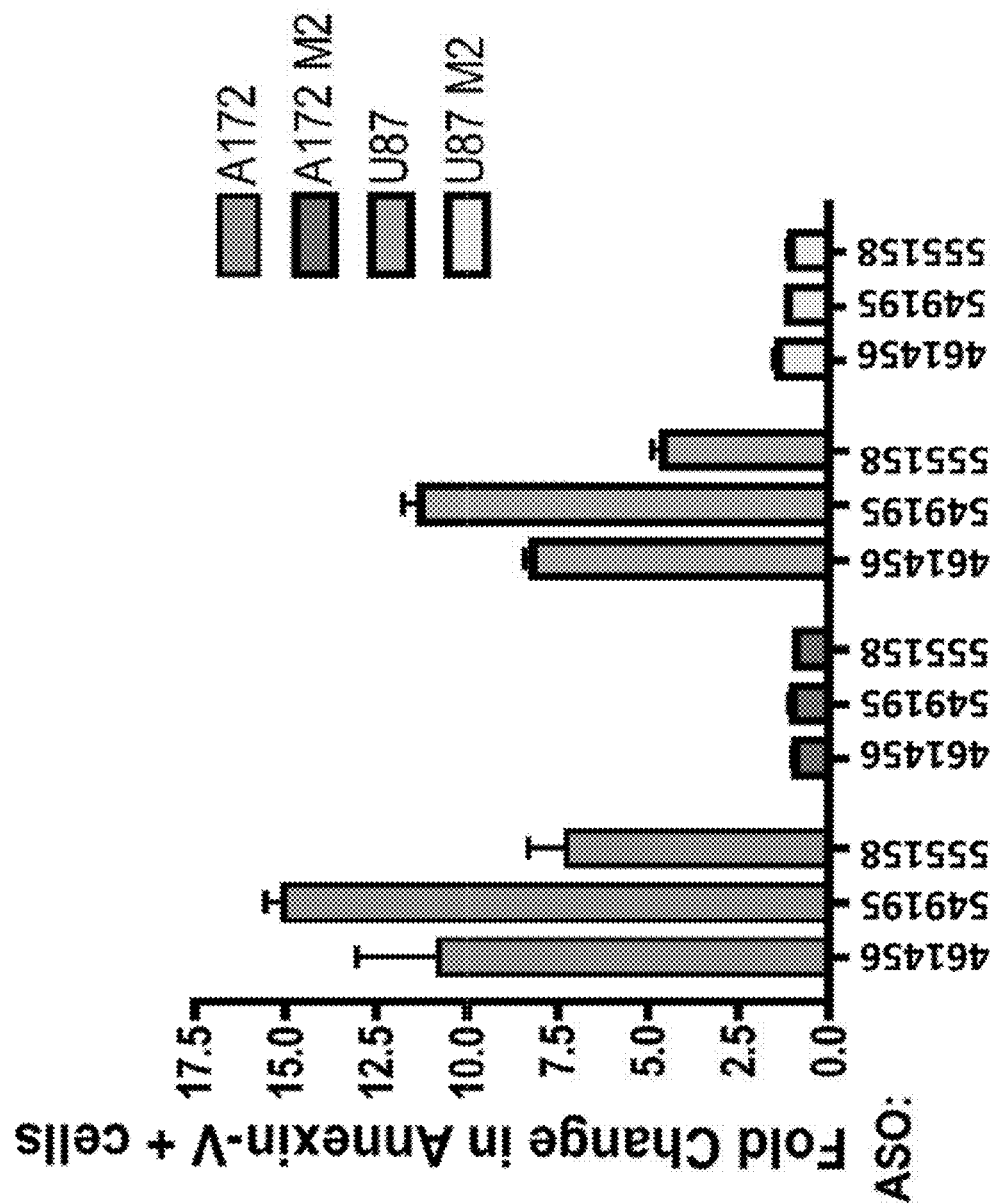
FIG. 6d: Histogram analysis of cells grown as in FIG. 6b and transfected with the indicated ASOs. Error bars represent s.d. (n=3).

To investigate the role of PK-M2 downregulation in apoptosis, U87-MG and A172 cells overexpressing PK-M2 were treated with ISIS 461456, ISIS 549197, ISIS 555158, or control ASO at a final concentration of 90 nM. The cells were analyzed by immunoblotting as well as by Annexin V flow cytometry. The results are presented in FIGS. 6b and 6d, as well as Tables 12 and 13, and indicate that overexpression of PK-M2 in both cell lines rescued the cells from the ASO-mediated apoptosis, leading to the decrease in the number of Annexin V-positive cells to baseline levels. The histogram shown in FIG. 6d indicates the fold-increase in Annexin V-positive cells, compared to control ASO for each cell line.

TABLE 12

Fold change of apoptosis compared to control ASO in PK-M1-inducible cells

| Treatment | Doxycycline | Fold-change |
|---|---|---|
| ISIS 461456 | No | 3.0 |
| | Yes | 3.3 |
| ISIS 549197 | No | 8.4 |
| | Yes | 7.5 |

TABLE 13

Fold change of apoptosis compared to control ASO in PK-M2-overexpressing cells

| Cell line | Treatment | % apoptosis |
|---|---|---|
| A172 | ISIS 555158 | 7.3 |
| | ISIS 461456 | 10.8 |
| | ISIS 549197 | 15.0 |
| 0.9A172 M2 | ISIS 555158 | 0.9 |
| | ISIS 461456 | 0.9 |
| | ISIS 549197 | 1.0 |
| U87-MG | ISIS 555158 | 4.6 |
| | ISIS 461456 | 8.2 |
| | ISIS 549197 | 11.3 |
| U87-MG M2 | ISIS 555158 | 1.0 |
| | ISIS 461456 | 1.4 |
| | ISIS 549197 | 1.1 |

Example 8: siRNA Knockdown of PK-M2 in A172 Cells

To confirm the effect on apoptosis in glioblastoma cells by antisense inhibition, siRNA knockdown of PK-M2 in A172 cells was employed.

Four siRNAs targeting exon 10 of human PKM2 were obtained from Sigma Genosys, and have sense-strand sequences 5'-CCAUAAUCGUCCGCACCAA-3' (M2si1; designated SEQ ID NO: 59), 5'-CAUCUACCAC-UUGCAAUUA-3' (M2si2; designated SEQ ID NO: 60), 5'-CCGUGGAGGCCUCCUUCAA-3' (M2si3; designated SEQ ID NO: 61) and 5'-CUUGCAAUUAUUUGAGGAA-3' (M2si4; designated SEQ ID NO: 62). A172 cells (4×10$^6$) in 6-well plates were transfected with 400 pmol of siRNA duplex using LipofectAMINE2000®. Cells were harvested 48 hr later.

Figure 7:
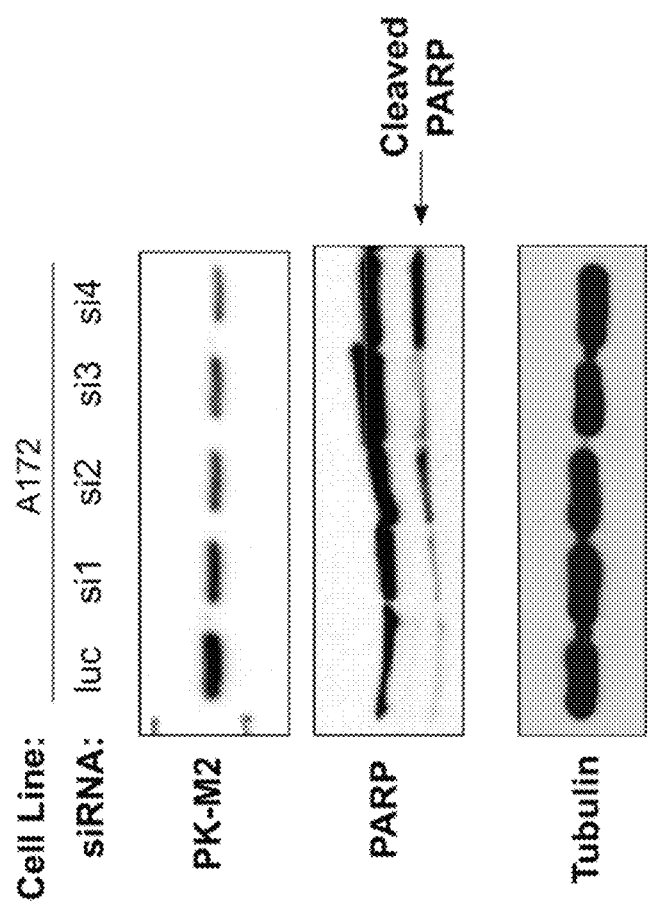
FIG. 7: Immunoblot analysis of A172 cells independently transfected with four different PK-M2 siRNAs. Antibodies used are indicated on the left.

The results are presented in FIG. 7. Knockdown of PK-M2 also led to the appearance of cleaved PARP after 48 hrs. These observations confirm that the down-regulation of PK-M2 expression, but not the induction of PK-M1 expression, leads to apoptosis in glioblastoma cell lines.

Example 9: Effect of 2'-O-Methoxyethyl Antisense Oligonucleotides on PK-M Splicing In Vivo The ASOs listed in Table 14 below were designed to target exon 10 of the mouse PK-M transcript comprising GEN-BANK Accession No. NT_039474.8 truncated from nucleotides 5923000 to 5949000 (designated herein as SEQ ID NO: 63). (Note that the human ASOs described herein target the complement of the human genomic PK-M sequence NT_010194.16 truncated from nucleotides 43281289 to 43314403, whereas the mouse ASOs target the mouse genomic sequence NT_039474.8 truncated from nucleotides 5923000 to 5949000 because the mouse sequence, SEQ ID: 63, corresponds to the non-coding strand of the mouse genomic DNA. In each case, the ASOs are complementary to the RNA transcript.) Each of the ASOs in Table 14 is also complementary to the human PK-M transcript with 0-3 mismatches. Each of the ASOs is 15 nucleotides in length, with uniform 2'-O-methoxyethyl ribose sugar residues, and uniform phosphorothioate internucleoside linkages. All the cytosine nucleobases are 5-methylcytosines.

To examine the effects of antisense oligonucleotide treatment on endogenous PK-M transcripts in vivo, C57Bl/6 wild-type (WT) mice were injected subcutaneously once per week for three weeks with one of the ASOs listed in Table 14 at 100 mg/kg or with PBS as a control. Each treatment group consisted of 4 animals. Four days after the administration of the last dose, the mice were sacrificed and tissues were collected.

PK-M1 and PK-M2 mRNA levels in each of the mice's livers were determined using real-time PCR and RIBOGREEN® RNA quantification reagent (Molecular Probes, Inc. Eugene, Oreg.) according to standard protocols. Two mouse-specific primer probe sets were used to amplify endogenous PK-M1. The first primer set anneals to PK-M exons 8 and 9 (mPKMF: 5'-TGTCTGGAGAAACAGC-CAAGG-3', designated herein as SEQ ID NO: 64; mPKMR: 5'-CAAGCTCTTCAAACAGCAGACG-3', designated herein as SEQ ID NO:65; probe sequence: 5'-AGCACCT-GATAGCTCGGGAGGC-3', designated herein as SED ID NO: 66). The second PK-M1 primer set anneals to exons 9 and 11 (mPKMF: 5'-AAGATGCCACGGTACAGATGG-3', designated herein as SEQ ID NO: 67; mPKMR 5'-CA-GACCTCATGGAGGCCATG-3', designated herein as SEQ ID NO: 68; probe sequence: 5'-TGGCAGGAGTGCTCAC-CAAGT-3', designated herein as SED ID NO: 69). Two mouse-specific primer probe sets were used to amplify endogenous PK-M2. The first PK-M2 primer set anneals to PK-M exons 8 and 10 (mPKMF: 5'-GGAGTTCCTCGAATAGCTGCAAG-3', designated herein as SEQ ID NO:70; and mPKMR: 5'-AGTCCTG-GATGGAGCAGACT-3', designated herein as SEQ ID NO:71; probe sequence: 5'-GCTGTTCG-CATGCAGCACCT-3', designated herein as SED ID NO:72). The second PK-M2 primer set anneals to exons 10 and 11 (mPKMF: 5'-GCGAGCAGTCTGGGGATTTC-3', designated herein as SEQ ID NO: 73; mPKMR: 5'-ACCC-CACAGAAGCTGCC-3', designated herein as SEQ ID NO:74; probe sequence: 5'-ACCAAGTCTGGCAG-GAGTGCTC-3', designated herein as SED ID NO:75). mRNA levels were determined relative to GAPDH prior to normalization to PBS-treated controls. The results in Table 15 are presented as the average percent of PK-M1 and PK-M2 mRNA levels for each treatment group, relative to the PK-M1 and PK-M2 mRNA levels of the PBS-treated control group, respectively, and are denoted as "% PBS". The standard error for all PK-M1 results was ≤34%, and the standard error for all PK-M2 results was ≤6%. The results for each primer probe set are listed. "ND" indicates no data because the ASO targets a portion of the amplicon, thereby preventing primer binding and amplification. All of the ASOs were well tolerated, as assessed by liver weight and ALT and AST levels.

TABLE 14

ASOs targeting mouse PK-M exon 10

| Isis No. | Mouse Target Start Site | Mouse Target Stop Site | Sequence (5' to 3') | SEQ ID NO. |
| --- | --- | --- | --- | --- |
| 606601 | 20994 | 21011 | GTTCCTCGAATAGCTGCA | 76 |
| 606602 | 20995 | 21012 | AGTTCCTCGAATAGCTGC | 77 |
| 606604 | 20997 | 21014 | GGAGTTCCTCGAATAGCT | 78 |
| 606651 | 21096 | 21113 | TGAGCACGATAATGGCCC | 79 |
| 606653 | 21098 | 21115 | GGTGAGCACGATAATGGC | 80 |
| 606661 | 21106 | 21123 | CCAGACTTGGTGAGCACG | 81 |

TABLE 15

Effect of ASOs targeting mouse PK-M exon 10 on PK-M splicing in vivo

| Isis No. | PK-M1, exons 8, 9 primer probe set (% PBS) | PK-M1, exons 9, 11 primer probe set (% PBS) | PK-M2, exons 8, 10 primer probe set (% PBS) | PK-M2, exons 10, 11 primer probe set (% PBS) |
| --- | --- | --- | --- | --- |
| n/a | 100 | 100 | 100 | 100 |
| 606601 | 260 | 250 | ND | 50 |
| 606602 | 290 | 270 | ND | 50 |
| 606604 | 210 | 200 | ND | 60 |
| 606651 | 440 | 400 | 50 | ND |
| 606653 | 270 | 270 | 50 | ND |
| 606661 | 320 | 200 | 40 | ND |

Example 10: Effect of Deoxy, MOE, and cEt Antisense Oligonucleotides on PK-M Splicing In Vivo The ASOs listed in Table 16 below were designed to target exon 10 of SEQ ID NO: 63. Each of the ASOs in Table 16 is also complementary to the human PK-M transcript with 0-3 mismatches. The ASOs are either 16 or 18 nucleotides in length, with deoxy sugar residues, 2'-MOE modified sugar residues, or cEt modified sugar residues, and uniform phosphorothioate internucleoside linkages. The Chemistry column presents the positions of the sugar residues; 'd' signifies a deoxy sugar, 'e' signifies 2'-MOE modified sugar residue, and 'k' signifies a cEt modified sugar residue. All the cytosine nucleobases are 5-methylcytosines.

To examine the effects of antisense oligonucleotide treatment on endogenous PK-M transcripts in vivo, C57Bl/6 WT mice were injected subcutaneously once per week for four weeks with one of the ASOs listed in Table 16 at 100 mg/kg or with PBS as a control. Each treatment group consisted of 4 animals. Two days after the administration of the last dose, the mice were sacrificed and tissues were collected.

PK-M1 and PK-M2 mRNA levels in each of the mice's livers were determined using real-time PCR according to standard protocols. Mouse-specific primer probe sets, described in Example 9, were used to amplify endogenous PK-M1 and PK-M2. mRNA levels were determined relative to GAPDH prior to normalization to PBS-treated controls. The results in Table 17 are presented as the average percent of PK-M1 and PK-M2 mRNA levels for each treatment group, relative to the PK-M1 and PK-M2 mRNA levels of the PBS-treated control group, respectively, and are denoted as "% PBS". "ND" indicates no data because the ASO targets a portion of the amplicon, thereby preventing primer binding and amplification. All of the ASOs were well tolerated, as assessed by liver weight and ALT and AST levels, except for ISIS 607034 which resulted in elevation in all three or those measures of tolerability.

TABLE 16

ASOs targeting mouse PK-M exon 10

| Isis No. | Mouse Target Start Site | Mouse Target Stop Site | Chemistry | Sequence (5' to 3') | SEQ ID NO. |
| --- | --- | --- | --- | --- | --- |
| 606989 | 20980 | 20995 | kddkddkddkddkddk | CAAGTGGTAGATGGCA | 82 |
| 606996 | 21008 | 21023 | kddkddkddkddkddk | CCAGGCGGCGGAGTTC | 83 |
| 607001 | 21044 | 21059 | kddkddkddkddkddk | CGGCGGCAGCTTCTGT | 84 |
| 607003 | 21052 | 21067 | kddkddkddkddkddk | GGCACCCACGGCGGCA | 85 |
| 607016 | 21104 | 21119 | kddkddkddkddkddk | ACTTGGTGAGCACGAT | 86 |
| 607034 | 21000 | 21017 | kkddkddkddkddkddkk | GGCGGAGTTCCTCGAATA | 87 |
| 607041 | 21044 | 21061 | kkddkddkddkddkddkk | CACGGCGGCAGCTTCTGT | 88 |
| 607042 | 21048 | 21065 | kkddkddkddkddkddkk | CACCCACGGCGGCAGCTT | 89 |

TABLE 16-continued

ASOs targeting mouse PK-M exon 10

| Isis No. | Mouse Target Start Site | Mouse Target Stop Site | Chemistry | Sequence (5' to 3') | SEQ ID NO. |
|---|---|---|---|---|---|
| 607055 | 21100 | 21117 | kkddkddkddkddkddkk | TTGGTGAGCACGATAATG | 90 |
| 607057 | 21108 | 21125 | kkddkddkddkddkddkk | TGCCAGACTTGGTGAGCA | 91 |
| 607095 | 21100 | 21115 | keekeekeekeekeek | GGTGAGCACGATAATG | 92 |
| 607135 | 21100 | 21117 | kkeekeekeekeekeeke | TTGGTGAGCACGATAATG | 93 |
| 607136 | 21104 | 21121 | kkeekeekeekeekeeke | AGACTTGGTGAGCACGAT | 94 |

TABLE 17

Effect of ASOs targeting mouse PK-M exon 10 on PK-M splicing in vivo

| Isis No. | PK-M1, exons 8, 9 primer probe set (% PBS) | PK-M1, exons 9, 11 primer probe set (% PBS) | PK-M2, exons 8, 10 primer probe set (% PBS) | PK-M2, exons 10, 11 primer probe set (% PBS) |
|---|---|---|---|---|
| n/a | 100 | 100 | 100 | 100 |
| 606989 | 421 | 476 | ND | 86 |
| 606996 | 326 | 315 | ND | 25 |
| 607001 | 398 | 429 | 65 | ND |
| 607003 | 365 | 353 | 69 | ND |
| 607016 | 435 | 389 | 56 | ND |
| 607034 | 525 | 626 | ND | 148 |
| 607041 | 335 | 381 | 78 | ND |
| 607042 | 240 | 306 | 92 | ND |
| 607055 | 987 | 859 | 73 | ND |
| 607057 | 327 | 126 | 34 | ND |
| 607095 | 428 | 171 | 51 | ND |
| 607135 | 475 | 39 | 54 | ND |
| 607136 | 389 | 265 | 71 | ND |

The invention claimed is:

1. A method of modulating splicing of a PK-M pre-mRNA transcript in a cell comprising contacting the cell with an antisense compound comprising a single-stranded modified oligonucleotide, wherein the single-stranded modified oligonucleotide consists of 15 to 25 linked nucleosides and has a nucleobase sequence comprising a complementary region, wherein the complementary region comprises at least 15 contiguous nucleobases and is 100% complementary to an equal-length portion of a target region of a PK-M transcript, wherein the target region of the PK-M transcript is within nucleobase 29153 and nucleobase 29281 of SEQ ID NO: 1, wherein each nucleoside of the single-stranded modified oligonucleotide comprises a modified sugar moiety, wherein the single-stranded modified oligonucleotide comprises 2'-deoxyribose unmodified sugar moieties, wherein the single-stranded modified oligonucleotide does not comprise more than 4 contiguous unmodified 2'-deoxynucleosides, and wherein inclusion of exon 9 of the PK-M transcript is increased and exclusion of exon 10 of the PK-M transcript is increased following contacting the cell with the antisense compound.

2. The method of claim 1, wherein the nucleobase sequence of the single-stranded modified oligonucleotide is 100% complementary to an equal-length portion of the target region of the PK-M transcript.

3. The method of claim 1, wherein the single-stranded modified oligonucleotide consists of 15 to 18 linked nucleosides.

4. The method of claim 1, wherein at least one modified sugar moiety is a 2'-O-methoxyethyl (2'-MOE) modified sugar moiety.

5. The method of claim 1, wherein at least one modified sugar moiety is a bicyclic modified sugar moiety.

6. The method of claim 5, wherein the at least one bicyclic modified sugar moiety is a LNA or cEt sugar moiety.

7. The method of claim 1, wherein each modified sugar moiety comprises the same modification.

8. The method of claim 1, wherein each modified sugar moiety is independently selected from a 2'-MOE modified sugar moiety and a bicyclic modified sugar moiety.

9. The method of claim 8, wherein the single-stranded modified oligonucleotide comprises a sugar motif of keekeekeekeek or kkeekeekeekeek, wherein each "k" represents a cEt bicyclic modified sugar moiety and each "e" represents a 2'-MOE modified sugar moiety.

10. The method of claim 1, wherein the single-stranded modified oligonucleotide comprises at least one modified internucleoside linkage.

11. The method of claim 10, wherein the at least one modified internucleoside linkage is a phosphorothioate internucleoside linkage.

12. The method of claim 10, wherein each internucleoside linkage of the single-stranded modified oligonucleotide is a phosphorothioate internucleoside linkage.

13. The method of claim 1, wherein the nucleobase sequence of the single-stranded modified oligonucleotide comprises a sequence as set forth in any one of SEQ ID NOs: 4 to 36.

14. The method of claim 1, wherein the amount of PK-M2 mRNA is decreased following contacting the cell with the antisense compound.

15. The method of claim 1, wherein the cell is in an animal.

16. The method of claim 15, wherein the method comprises administering the antisense compound into the central nervous system of the animal.

17. The method of claim 15, wherein the animal has one or more symptoms associated with cancer.

18. The method of claim 17, wherein the cancer is glioblastoma.

19. The method of claim 15, wherein the animal is a human.

20. A method of modulating splicing of a PK-M pre-mRNA transcript in a cell comprising contacting the cell with an antisense compound comprising a single-stranded modified oligonucleotide, wherein the single-stranded modified oligonucleotide consists of 15 to 25 linked nucleosides and has a nucleobase sequence comprising a complementary region, wherein the complementary region comprises at least 15 contiguous nucleobases and is 100% complementary to an equal-length portion of a target region of a PK-M transcript, wherein the target region of the PK-M transcript is within nucleobase 29153 and nucleobase 29281 of SEQ ID NO: 1, wherein the single-stranded modified oligonucleotide comprises a sugar motif of kddkddkddkddk or kkddkddkddkddk, each "k" represents a cEt bicyclic modified sugar moiety and each "d" represents a 2'-deoxyribose unmodified sugar moiety, wherein the single-stranded modified oligonucleotide does not comprise more than 4 contiguous unmodified 2'-deoxynucleosides, and wherein inclusion of exon 9 of the PK-M transcript is increased and exclusion of exon 10 of the PK-M transcript is increased following contacting the cell with the antisense compound.

* * * * *